(12) United States Patent
Schindhelm et al.

(10) Patent No.: US 10,426,380 B2
(45) Date of Patent: Oct. 1, 2019

(54) METHOD AND APPARATUS FOR MONITORING CARDIO-PULMONARY HEALTH

(71) Applicants: ResMed Sensor Technologies Limited, Dublin (IE); ResMed Limited, Bella Vista, New South Wales (AU)

(72) Inventors: Klaus Henry Schindhelm, Sydney (AU); Steven Paul Farrugia, Sydney (AU); Michael Waclaw Colefax, Sydney (AU); Faizan Javed, Sydney (AU); Rami Khushaba, Sydney (AU); Conor Heneghan, Dublin (IE); Philip De Chazal, Blue Mountains (AU); Alberto Zaffaroni, Dublin (IE); Niall Fox, Tullamore (IE); Patrick Celka, Saviese (CH); Emer O'Hare, Dublin (IE); Stephen James Redmond, Sydney (AU)

(73) Assignee: ResMed Sensor Technologies Limited (IE)

( * ) Notice: Subject to any disclaimer, the term of this patent is extended or adjusted under 35 U.S.C. 154(b) by 1013 days.

(21) Appl. No.: 14/403,398

(22) PCT Filed: May 30, 2013

(86) PCT No.: PCT/AU2013/000564
§ 371 (c)(1),
(2) Date: Nov. 24, 2014

(87) PCT Pub. No.: WO2013/177621
PCT Pub. Date: Dec. 5, 2013

(65) Prior Publication Data
US 2015/0164375 A1 Jun. 18, 2015

(30) Foreign Application Priority Data

May 30, 2012 (IE) ..................................... 2012/0254
Jun. 26, 2012 (AU) ................................ 2012902693
(Continued)

(51) Int. Cl.
*A61B 5/113* (2006.01)
*A61B 5/08* (2006.01)
(Continued)

(52) U.S. Cl.
CPC .............. *A61B 5/113* (2013.01); *A61B 5/08* (2013.01); *A61B 5/103* (2013.01); *A61B 5/4818* (2013.01);
(Continued)

(58) Field of Classification Search
CPC ..... A61B 5/113; A61B 5/1135; A61B 5/4803; A61B 5/4806; A61B 5/4809; A61B 5/4812; A61B 5/4815
See application file for complete search history.

(56) References Cited

U.S. PATENT DOCUMENTS

| 4,944,310 A | 7/1990 | Sullivan |
| 5,704,345 A | 1/1998 | Berthon-Jones |

(Continued)

FOREIGN PATENT DOCUMENTS

| CN | 101489478 A | 7/2009 |
| DE | 102007039004 A1 | 3/2008 |

(Continued)

OTHER PUBLICATIONS

Dai Yumino and T. Douglas Bradley "Central Sleep Apnea and Cheyne-Stokes Respiration", Proceedings of the American Thoracic Society, vol. 5, No. 2 (2008), pp. 226-236.
(Continued)

*Primary Examiner* — Meredith Weare
(74) *Attorney, Agent, or Firm* — Botos Churchill IP Law LLP

(57) ABSTRACT

Disclosed is a cardio-pulmonary health monitoring apparatus. The apparatus comprises a contactless motion sensor configured to generate one or more movement signals representing bodily movement of a patient during a monitoring session; a processor; and a memory storing program instructions configured to cause the processor to carry out a method of processing the one or more movement signals. The
(Continued)

method comprises extracting one or more sleep disordered breathing features from the one or more movement signals, and predicting whether a clinical event is likely to occur during a predetermined prediction horizon based on the one or more sleep disordered breathing features.

64 Claims, 22 Drawing Sheets

(30) Foreign Application Priority Data

| | | |
|---|---|---|
| Nov. 30, 2012 | (AU) | 2012905221 |
| Apr. 29, 2013 | (AU) | 2013901482 |

(51) Int. Cl.

| | |
|---|---|
| *A61B 5/103* | (2006.01) |
| *G08B 21/02* | (2006.01) |
| *A61B 5/00* | (2006.01) |
| A61B 5/05 | (2006.01) |
| A61B 5/087 | (2006.01) |
| A61B 5/097 | (2006.01) |
| A61B 5/11 | (2006.01) |
| G16H 50/30 | (2018.01) |

(52) U.S. Cl.
CPC .......... *A61B 5/7221* (2013.01); *A61B 5/7264* (2013.01); *A61B 5/7275* (2013.01); *A61B 5/742* (2013.01); *A61B 5/746* (2013.01); *G08B 21/02* (2013.01); *A61B 5/0507* (2013.01); *A61B 5/087* (2013.01); *A61B 5/0816* (2013.01); *A61B 5/097* (2013.01); *A61B 5/1115* (2013.01); *A61B 5/1118* (2013.01); *A61B 5/1126* (2013.01); *A61B 5/4809* (2013.01); *A61B 5/7246* (2013.01); *G16H 50/30* (2018.01)

(56) References Cited

U.S. PATENT DOCUMENTS

| | | | | |
|---|---|---|---|---|
| 5,738,102 | A * | 4/1998 | Lemelson | A61B 5/0205 128/903 |
| 6,367,475 | B1 | 4/2002 | Kofoed et al. | |
| 6,390,091 | B1 | 5/2002 | Banner et al. | |
| 6,532,957 | B2 | 3/2003 | Berthon-Jones | |
| 6,532,959 | B1 | 3/2003 | Berthon-Jones | |
| 6,600,949 | B1 | 7/2003 | Turcott | |
| 6,635,021 | B1 | 10/2003 | Sullivan et al. | |
| 6,845,773 | B2 | 1/2005 | Berthon-Jones et al. | |
| 6,895,963 | B1 | 5/2005 | Martin et al. | |
| 6,951,217 | B2 | 10/2005 | Berthon-Jones | |
| 7,551,078 | B2 | 6/2009 | Carlson et al. | |
| 7,593,952 | B2 | 9/2009 | Soll et al. | |
| 8,844,525 | B2 | 9/2014 | Schindhelm et al. | |
| 2004/0122487 | A1 | 6/2004 | Hatlestad et al. | |
| 2004/0236240 | A1* | 11/2004 | Kraus | A61B 5/0205 600/529 |
| 2005/0076615 | A1 | 4/2005 | Wallis | |
| 2007/0118054 | A1 | 5/2007 | Pinhas et al. | |
| 2007/0161913 | A1 | 7/2007 | Farrell et al. | |
| 2007/0213622 | A1* | 9/2007 | Reisfeld | A61B 5/0402 600/484 |
| 2007/0215146 | A1 | 9/2007 | Douglas et al. | |
| 2007/0293779 | A1 | 12/2007 | Bardy | |
| 2008/0000475 | A1* | 1/2008 | Hill | A61M 16/00 128/204.18 |
| 2008/0004906 | A1 | 1/2008 | Klass et al. | |
| 2008/0053440 | A1 | 3/2008 | Farrugia | |
| 2008/0177195 | A1* | 7/2008 | Armitstead | A61B 5/087 600/529 |
| 2008/0269625 | A1* | 10/2008 | Halperin | A61B 5/113 600/508 |
| 2008/0275349 | A1* | 11/2008 | Halperin | A61B 5/0205 600/484 |
| 2009/0121854 | A1* | 5/2009 | Raisanen | B60N 2/002 340/438 |
| 2009/0131803 | A1* | 5/2009 | Heneghan | A61B 5/4812 600/484 |
| 2009/0149778 | A1 | 6/2009 | Naujokat et al. | |
| 2009/0203972 | A1* | 8/2009 | Heneghan | A61B 5/0507 600/301 |
| 2009/0314290 | A1 | 12/2009 | Hickle | |
| 2010/0018530 | A1 | 1/2010 | Schindhelm et al. | |
| 2010/0022911 | A1 | 1/2010 | Wariar et al. | |
| 2010/0204550 | A1* | 8/2010 | Heneghan | G16H 50/30 600/301 |
| 2010/0258124 | A1 | 10/2010 | Madaus et al. | |
| 2010/0275921 | A1 | 11/2010 | Schindhelm et al. | |
| 2011/0178377 | A1 | 7/2011 | Heneghan et al. | |
| 2011/0179361 | A1 | 7/2011 | Cardarelli et al. | |
| 2011/0224517 | A1* | 9/2011 | Alvarez Gonzalez | A61B 5/14551 600/323 |
| 2011/0263997 | A1 | 10/2011 | Corn | |
| 2012/0116202 | A1 | 5/2012 | Bangera et al. | |
| 2012/0138533 | A1 | 6/2012 | Curtis et al. | |
| 2012/0145153 | A1 | 6/2012 | Bassin et al. | |
| 2013/0165807 | A1 | 6/2013 | Gobbi et al. | |

FOREIGN PATENT DOCUMENTS

| | | |
|---|---|---|
| JP | 2009532072 A | 9/2009 |
| JP | 2009538720 A | 11/2009 |
| NZ | 552070 A | 11/2008 |
| WO | 96/32055 A1 | 10/1996 |
| WO | 98/52467 A1 | 11/1998 |
| WO | 2004013611 A2 | 2/2004 |
| WO | 2006037184 A1 | 4/2006 |
| WO | 2006066337 A1 | 6/2006 |
| WO | 2007124126 A2 | 11/2007 |
| WO | 2007143535 A2 | 12/2007 |
| WO | 2009026582 A1 | 2/2009 |
| WO | 2007052108 A3 | 4/2009 |
| WO | 2009136337 A1 | 11/2009 |
| WO | 2011141916 A1 | 11/2011 |
| WO | 2012032402 A1 | 3/2012 |

OTHER PUBLICATIONS

International Search Report for Application No. PCT/AU2013/000564 dated Aug. 26, 2013.
Peslin et al. in "Respiratory mechanics studied by forced oscillations during artificial ventilation", Eur Rospir J, 1993, 6, 772-784.
Vasilliou et al. in "Expiratory flow limitation during mechanical ventilation detected by the forced oscillation method", Eur Rospir J, 1996, 9, 779-786.
White et al., "Role of nocturnal rostral fluid shift in the pathogenesis of obstructive and central sleep apnoea", J Physiol., Mar. 1, 2013, 591, pp. 1179-1193.
Extended European Search Report for Application No. 13796432.6 dated Jan. 21, 2016.
First Examination Report issued in corresponding AU application No. 2017200083 dated Jun. 28, 2018.
Senske, A View Inside a Respironics REMstar Pro CPAP Machine (https://www.cpap-supply.com/Articles.asp?ID=134 Last Updated Jan. 5, 2007 3:56:00 PM). (Year 2007).

* cited by examiner

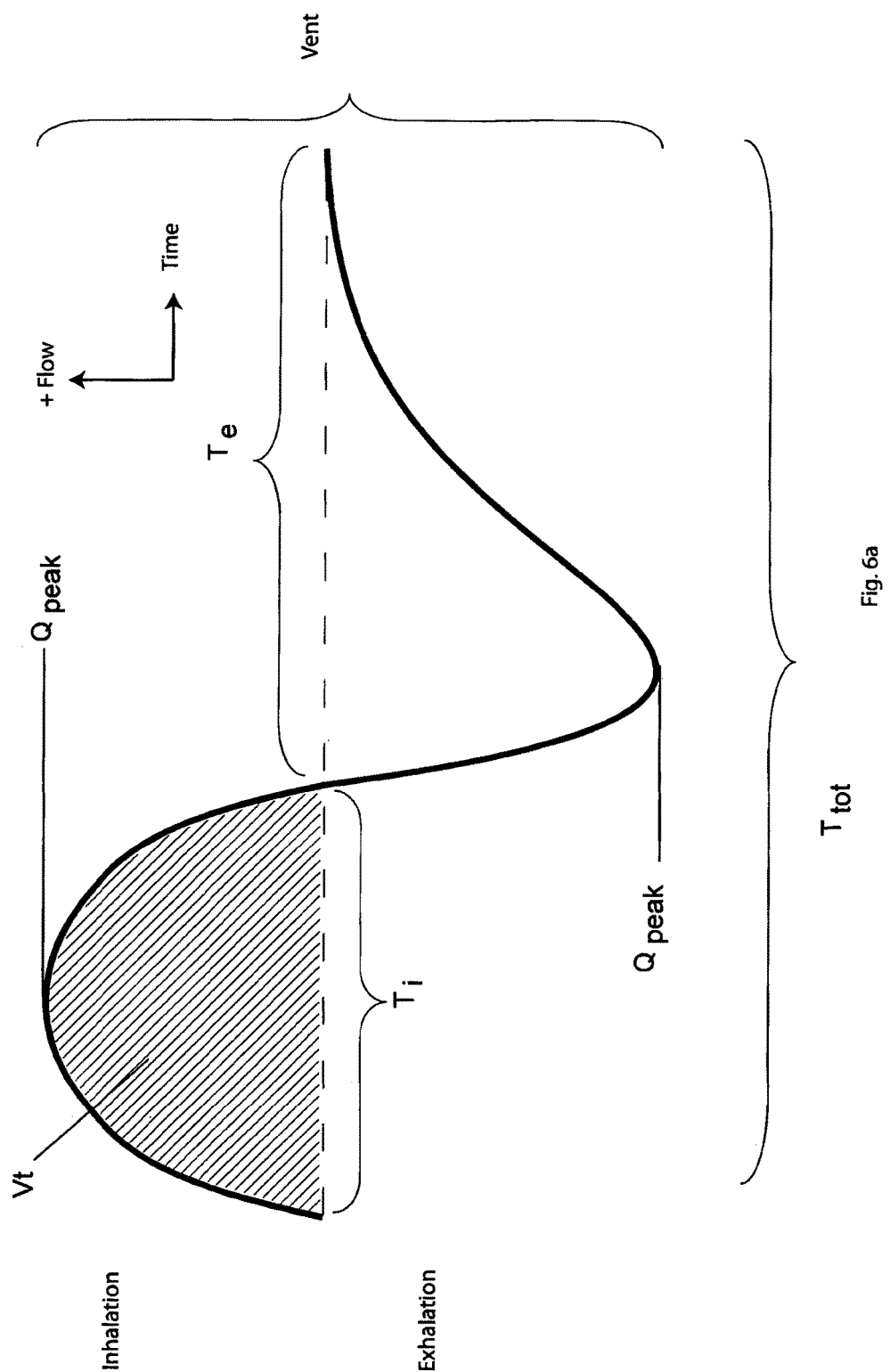

```
Detected Patterns
0=>SLEEP, 1=> WAKE
Arousals
    1    0 1 0
    2    0 1 1 0
    3    0 1 1 1 0
    4    0 1 1 1 1 0
    5    0 1 1 1 1 1 0
    6    0 1 1 1 1 1 1 0
Sleep Fragments
    7    1 1 1 1 0 1
    8    1 1 1 1 1 1 1 0 0 1
    9    1 1 1 1 1 1 1 1 1 1 0 0 0 1
   10    1 1 1 1 1 1 1 1 1 1 1 1 1 0 0 0 0 1
   11    1 1 1 1 1 1 1 1 1 1 1 1 1 1 1 1 1 0 0 0 0 0 1
   12    1 1 1 1 1 1 1 1 1 1 1 1 1 1 1 1 1 1 1 0 0 0 0 0 0 1
   13    1 1 1 1 1 1 1 1 1 1 1 1 1 1 1 1 1 1 1 1 1 1 1 0 0 0 0 0 0 0 1
   14    1 1 1 1 1 1 1 1 1 1 1 1 1 1 1 1 1 1 1 1 1 1 1 1 1 1 1 0 0 0 0 0 0 0 0 1

Replacement Patterns
    1    0 0 0
    2    0 0 0 0
    3    0 0 0 0 0
    4    0 0 0 0 0 0
    5    0 0 0 0 0 0 0
    6    0 0 0 0 0 0 0 0
    7    1 1 1 1 1 1
    8    1 1 1 1 1 1 1 1 1 1
    9    1 1 1 1 1 1 1 1 1 1 1 1 1 1
   10    1 1 1 1 1 1 1 1 1 1 1 1 1 1 1 1 1 1
   11    1 1 1 1 1 1 1 1 1 1 1 1 1 1 1 1 1 1 1 1 1 1 1
   12    1 1 1 1 1 1 1 1 1 1 1 1 1 1 1 1 1 1 1 1 1 1 1 1 1 1
   13    1 1 1 1 1 1 1 1 1 1 1 1 1 1 1 1 1 1 1 1 1 1 1 1 1 1 1 1 1 1 1
   14    1 1 1 1 1 1 1 1 1 1 1 1 1 1 1 1 1 1 1 1 1 1 1 1 1 1 1 1 1 1 1 1 1 1 1 1
```

Fig. 7g

METHOD AND APPARATUS FOR MONITORING CARDIO-PULMONARY HEALTH

CROSS-REFERENCE TO RELATED APPLICATIONS

This application claims the benefit of following applications, the disclosures of which are incorporated herein in their entirety by reference: Ireland application no. IE 2013/0254, filed 30 May 2012; Australian provisional application no. 2012902693, filed 26 Jun. 2012; Australian provisional application no. 2012905221, filed 30 Nov. 2012; and Australian provisional application no. 2013901482 filed 29 Apr. 2013.

STATEMENT REGARDING FEDERALLY SPONSORED RESEARCH OR DEVELOPMENT

Not Applicable

THE NAMES OF PARTIES TO A JOINT RESEARCH DEVELOPMENT

Not Applicable

SEQUENCE LISTING

Not Applicable

BACKGROUND OF THE INVENTION (1) Field of the Invention

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

(2) Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of cardio-pulmonary disorders exist.

Obstructive Sleep Apnea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Periodic or modulated breathing, for example Cheyne-Stokes Respiration (CSR), is a disorder of a patient's respiratory controller in which there are rhythmic alternating periods of waxing and waning ventilation (hyperpneas and apneas/hypopneas), causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Heart failure is a relatively common and severe clinical condition, characterised by the inability of the heart to keep up with the oxygen demands of the body. Management of heart failure is a significant challenge to modern healthcare systems due to its high prevalence and severity. Heart failure is a chronic condition, which is progressive in nature. The progression of heart failure is often characterized as relatively stable over long periods of time (albeit with reduced cardiovascular function) punctuated by episodes of an acute nature. In these acute episodes, the patient experiences worsening of symptoms such as dyspnea (difficulty breathing), gallop rhythms, increased jugular venous pressure, and orthopnea. This is typically accompanied by overt congestion (which is the buildup of fluid in the pulmonary cavity). This excess fluid often leads to measurable weight gain of several kilograms. In many cases, however, by the time overt congestion has occurred, there are limited options for the doctor to help restabilize the patients, and in many cases the patient requires hospitalization. In extreme cases, without timely treatment, the patient may undergo acute decompensated heart failure (ADHF).

Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat CSR, OHS, COPD, NMD and Chest Wall disorders.

PAP Device

The air at positive pressure under CPAP therapy is typically supplied to the airway of a patient by a PAP device such as a motor-driven blower. The outlet of the blower is connected via a flexible delivery conduit to a patient interface such as a mask.

Monitoring Systems

It is of interest to be able to predict potential cardiopulmonary events such as ADHF events with a view to preventing or ameliorating such events. Characteristics that have been proposed or used for the purpose of predicting cardio-pulmonary events include body weight, levels of B natriuretic peptides (BNP), nocturnal heart rate, changes in sleeping posture, and changes in respiration. Polysomnography (PSG) is a conventional system for diagnosis and prognosis of cardio-pulmonary disorders. In addition, contact sensor modalities such as masks or oronasal cannulae with capability for monitoring and analysing respiratory parameters during sleep to determine the severity of sleep disordered breathing are known. However, such systems are complicated and potentially expensive, and/or may be uncomfortable or impractical for a patient at home trying to sleep.

BRIEF SUMMARY OF THE TECHNOLOGY

The present technology is directed towards providing medical devices for use in the diagnosis and prognosis of cardio-pulmonary disorders having one or more of improved comfort, cost, efficacy, ease of use and manufacturability.

A first aspect of the present technology relates to apparatus used in the diagnosis and prognosis of a cardio-pulmonary disorder.

Another aspect of the present technology relates to methods used in the diagnosis and prognosis of a cardio-pulmonary disorder.

One form of the present technology comprises cardio-pulmonary health monitoring apparatus and methods for monitoring cardio-pulmonary health of a patient that extract features indicative of the severity of sleep disordered breathing by a patient from movement signal(s) obtained from a contactless motion sensor representing bodily movement of the patient, and uses the extracted features to predict whether a clinical event is likely to occur during a predetermined prediction horizon.

Another aspect of one form of the present technology is cardio-pulmonary health monitoring apparatus and methods that analyse sensor data related to cardio-pulmonary health, generate a query for display to a patient based on the analysis, and generate a clinical alert based on a response to the query.

Another aspect of one form of the present technology is cardio-pulmonary health monitoring apparatus and methods that analyse respiratory parameters extracted from sensor data and generate a potential relapse alert based on the analysis.

Another aspect of one form of the present technology is cardio-pulmonary health monitoring apparatus and methods that extract features indicative of the severity of sleep disordered breathing from movement signal(s) obtained from a contactless motion sensor representing bodily movement of the patient.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements, including.

Treatment Systems

Monitoring Systems

Figure 1A:
FIG. 1a shows an example system suitable for implementation with in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.
Figure 1B:

FIG. 1b shows a contactless sensor unit monitoring a sleeping patient.

Respiratory System

Figure 2A:
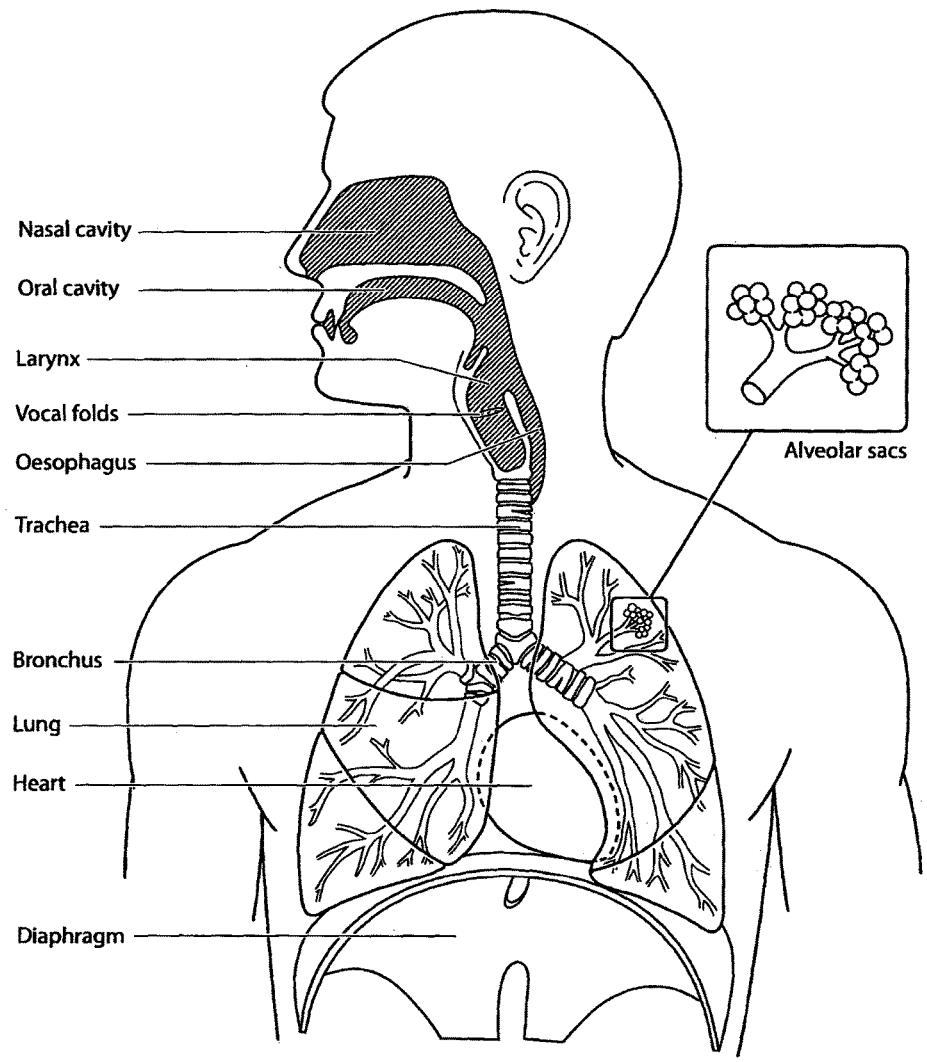

FIG. 2a shows an overview of a human respiratory system including the nasal and oral cavities, the larynx, vocal folds, oesophagus, trachea, bronchus, lung, alveolar sacs, heart and diaphragm.

Figure 2B:
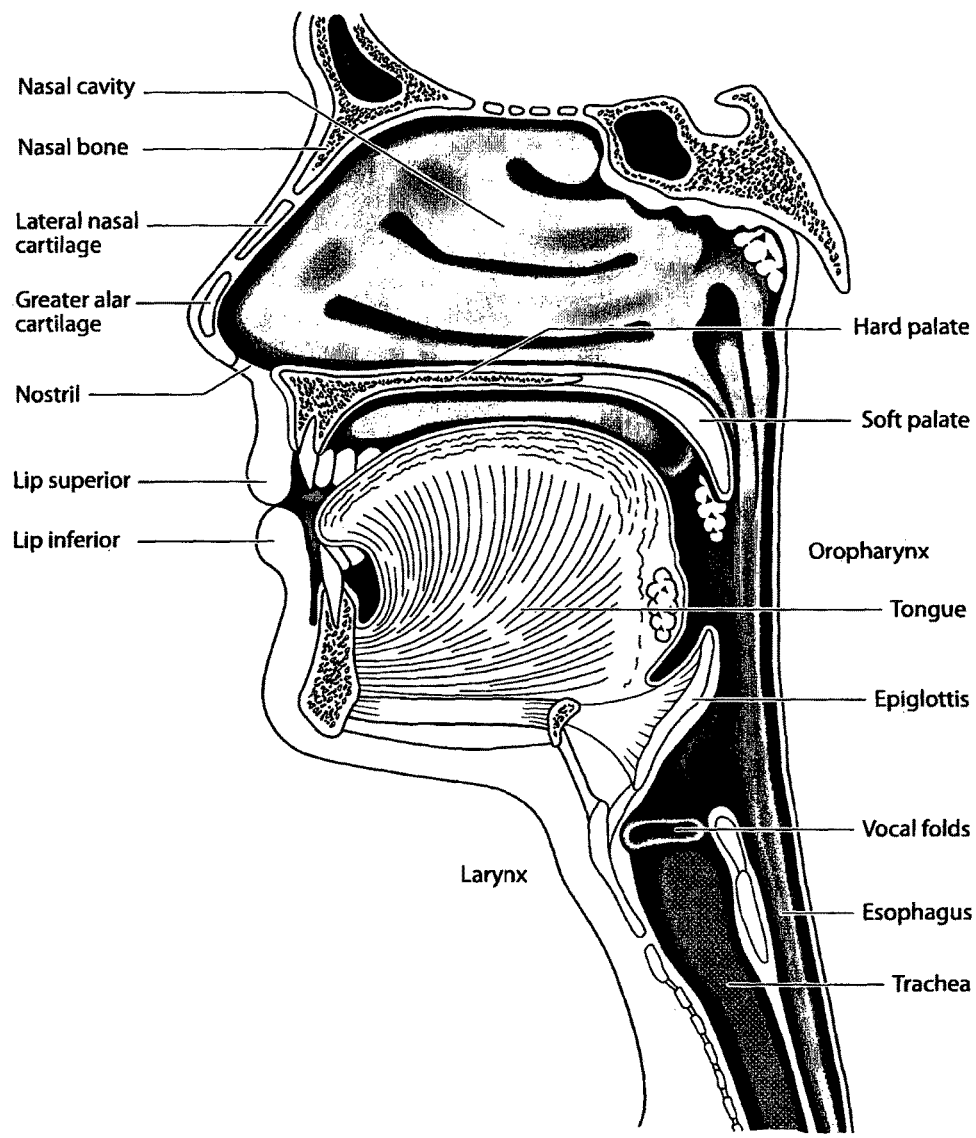

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Patient Interface

Figure 3A:
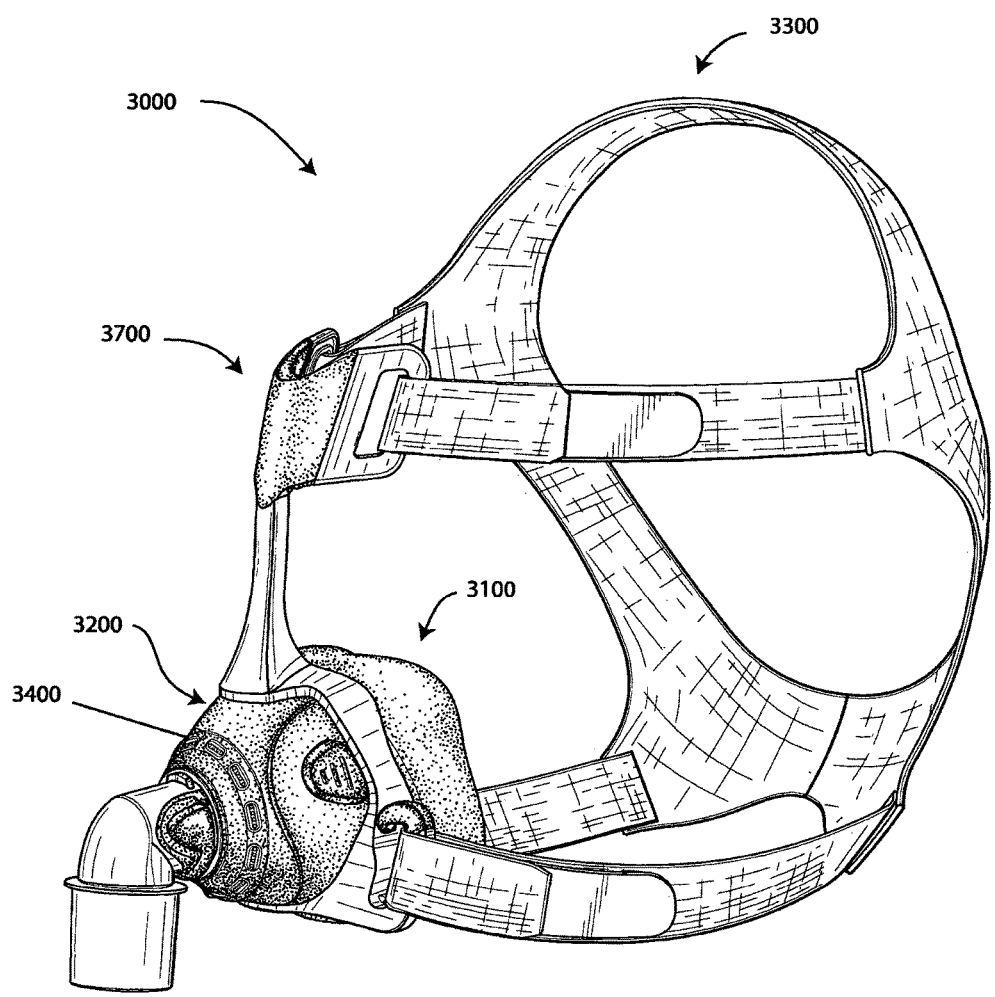

FIG. 3a shows a patient interface in accordance with one form of the present technology.

PAP Device

Figure 4A:
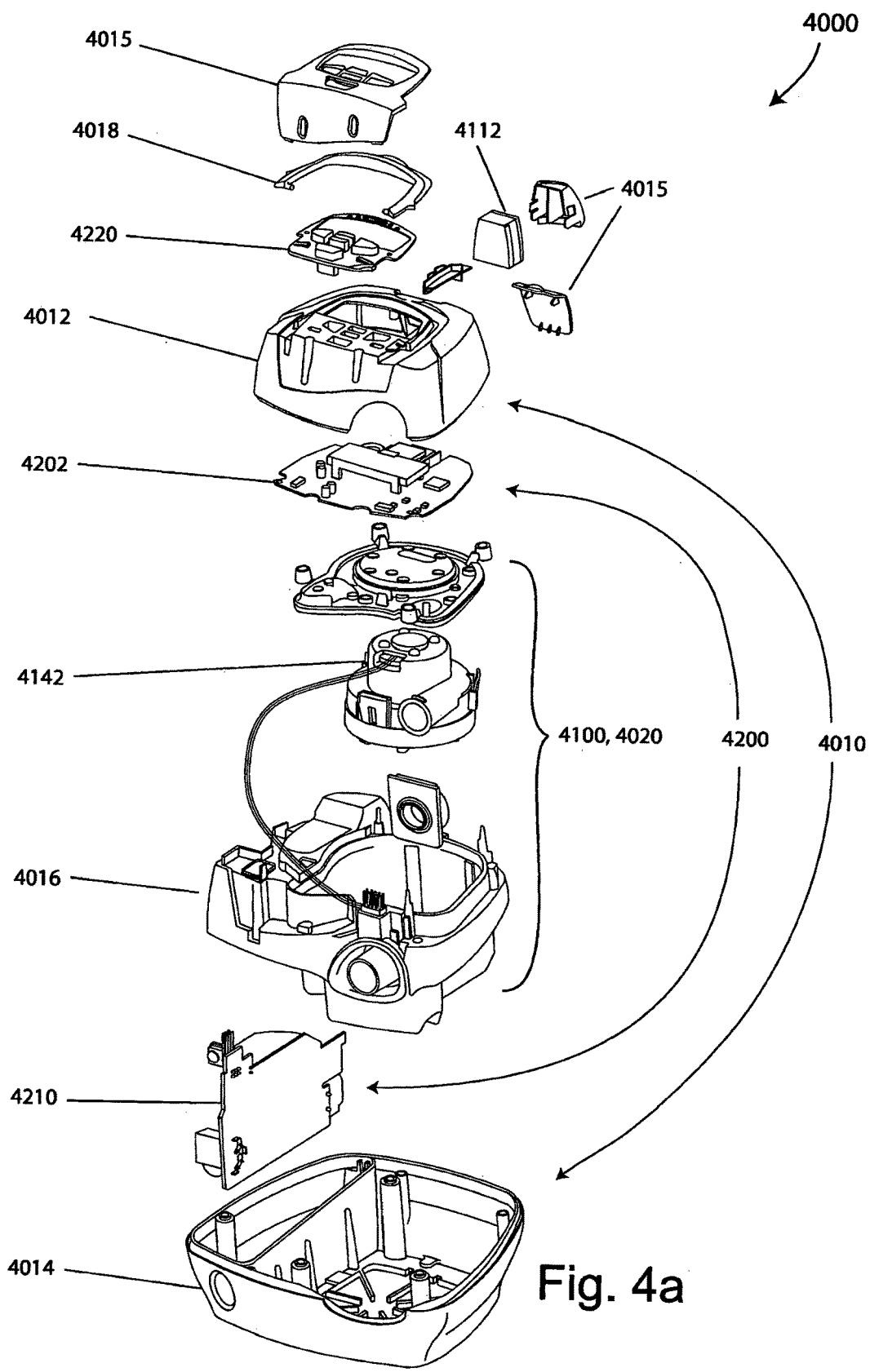

FIG. 4a shows a PAP device in accordance with one form of the present technology.

Humidifier

Figure 5A:
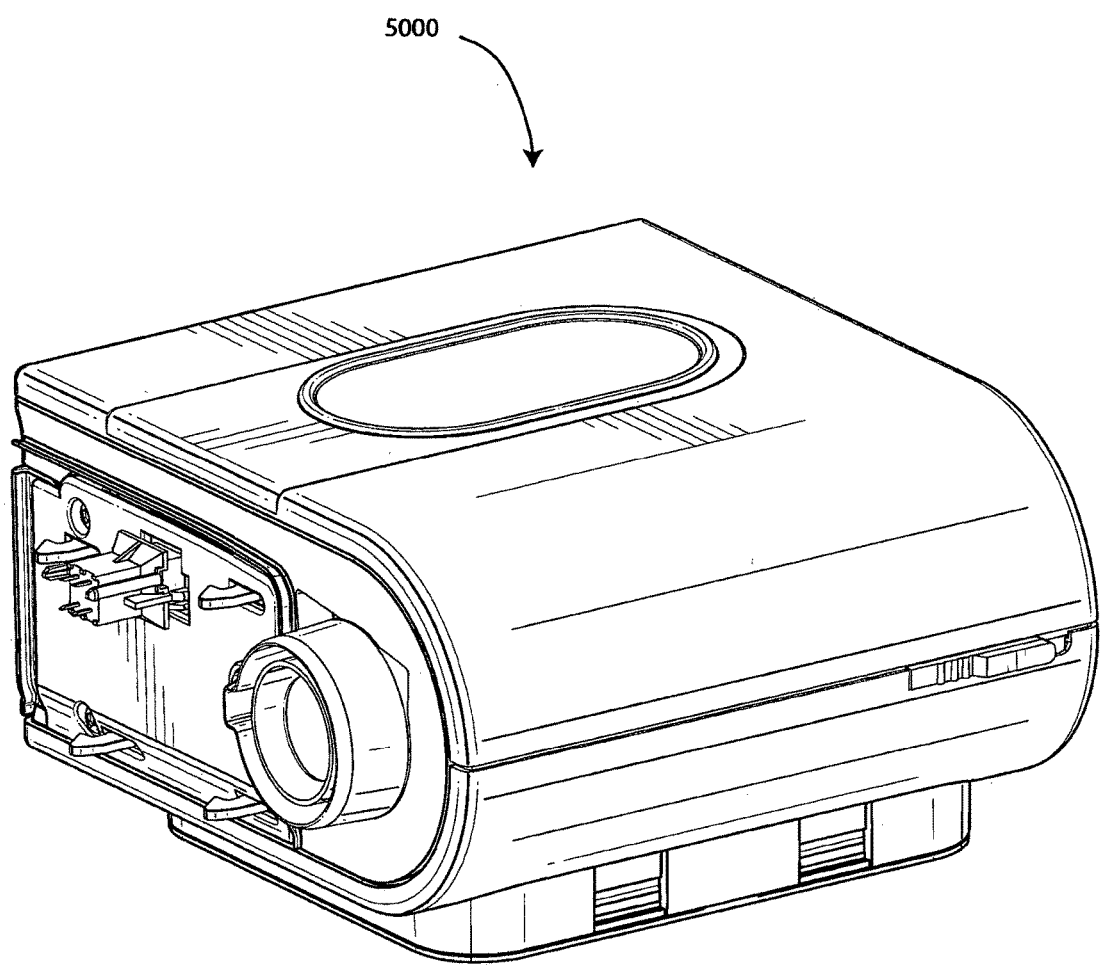

FIG. 5a shows a humidifier in accordance with one aspect of the present technology.

Breathing Waveforms

FIG. 6a shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

Figure 6B:
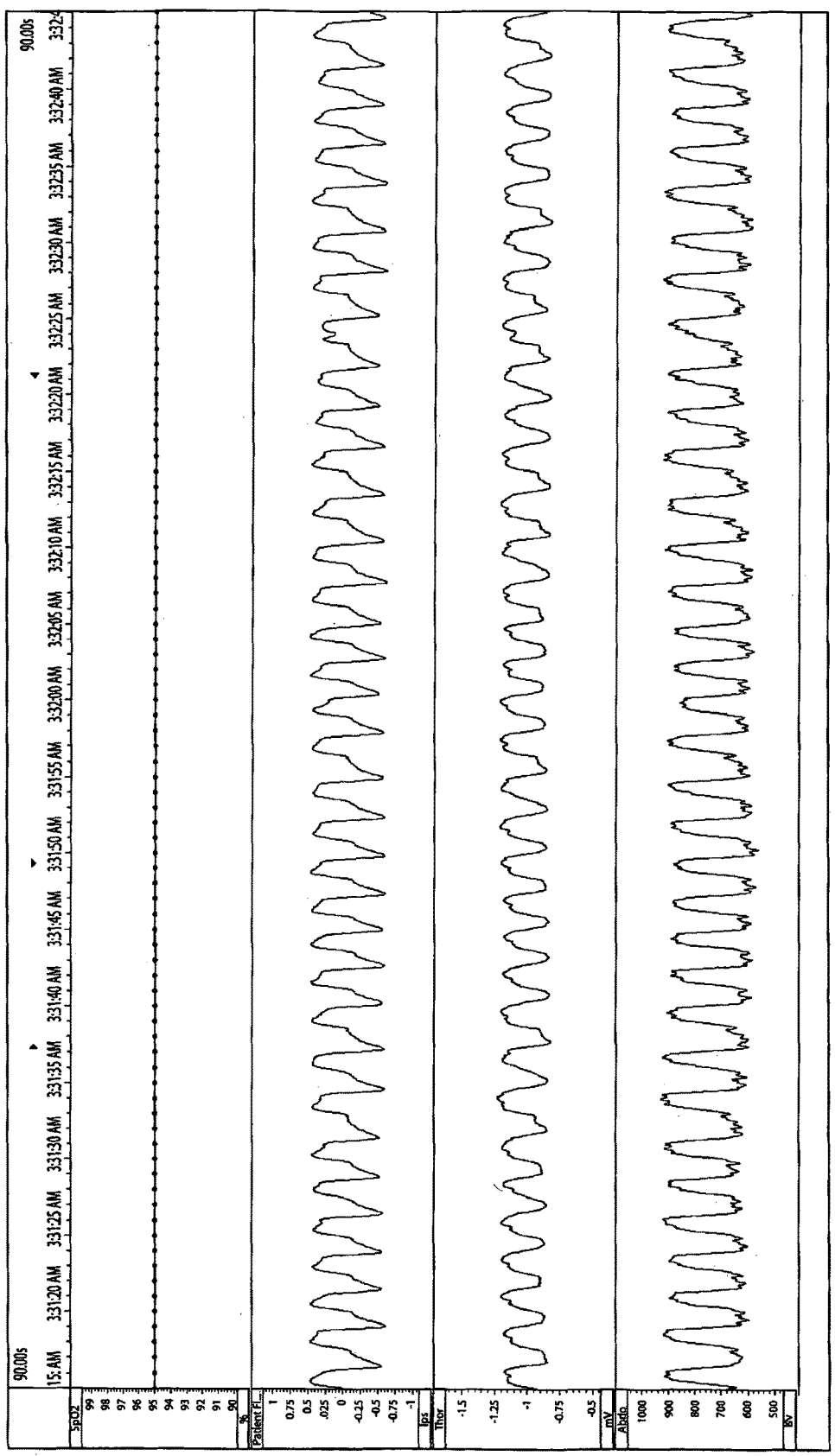

FIG. 6b shows a patient during Non-REM sleep breathing normally over a period of about ninety seconds, with about 34 breaths. This being treated with Automatic PAP, and the mask pressure was about 11 $cmH_2O$. The top channel shows oximetry (SpO2), the scale has a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

Figure 6C:
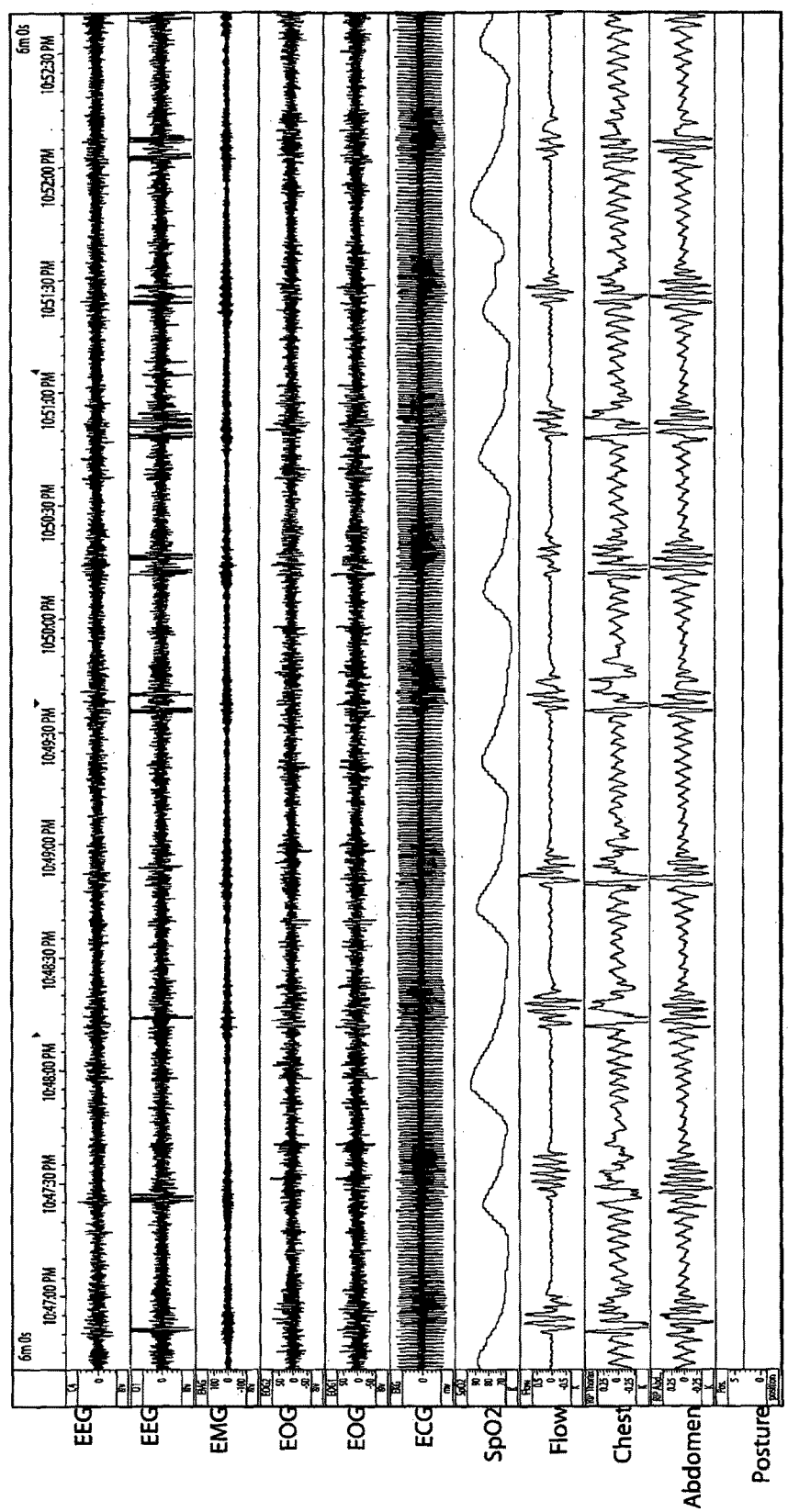

FIG. 6c shows polysomnography of a patient. There are eleven signal channels from top to bottom with a 6 minute horizontal span. The top two channels both are EEG (electoencephalogram) from different scalp locations. Periodic spikes in second represent cortical arousal and related activity. The third channel down is submental EMG (electromyogram). Increasing activity around time of arousals represent genioglossus recruitment. The fourth & fifth channels are EOG (electro-oculogram). The sixth channel is an electocardiogram. The seventh channel shows pulse oximetry (SpO2) with repetitive desaturations to below 70% from about 90%. The eighth channel is respiratory airflow using nasal cannula connected to differential pressure transducer. Repetitive apneas of 25 to 35 seconds alternating with 10 to 15 second bursts of recovery breathing coinciding with EEG arousal and increased EMG activity. The ninth shows movement of chest and tenth shows movement of abdomen. The abdomen shows a crescendo of movement over the length of the apnea leading to the arousal. Both become untidy during the arousal due to gross bodily movement during recovery hyperpnea. The apneas are therefore obstructive, and the condition is severe. The lowest channel is posture, and in this example it does not show change.

Figure 6D:
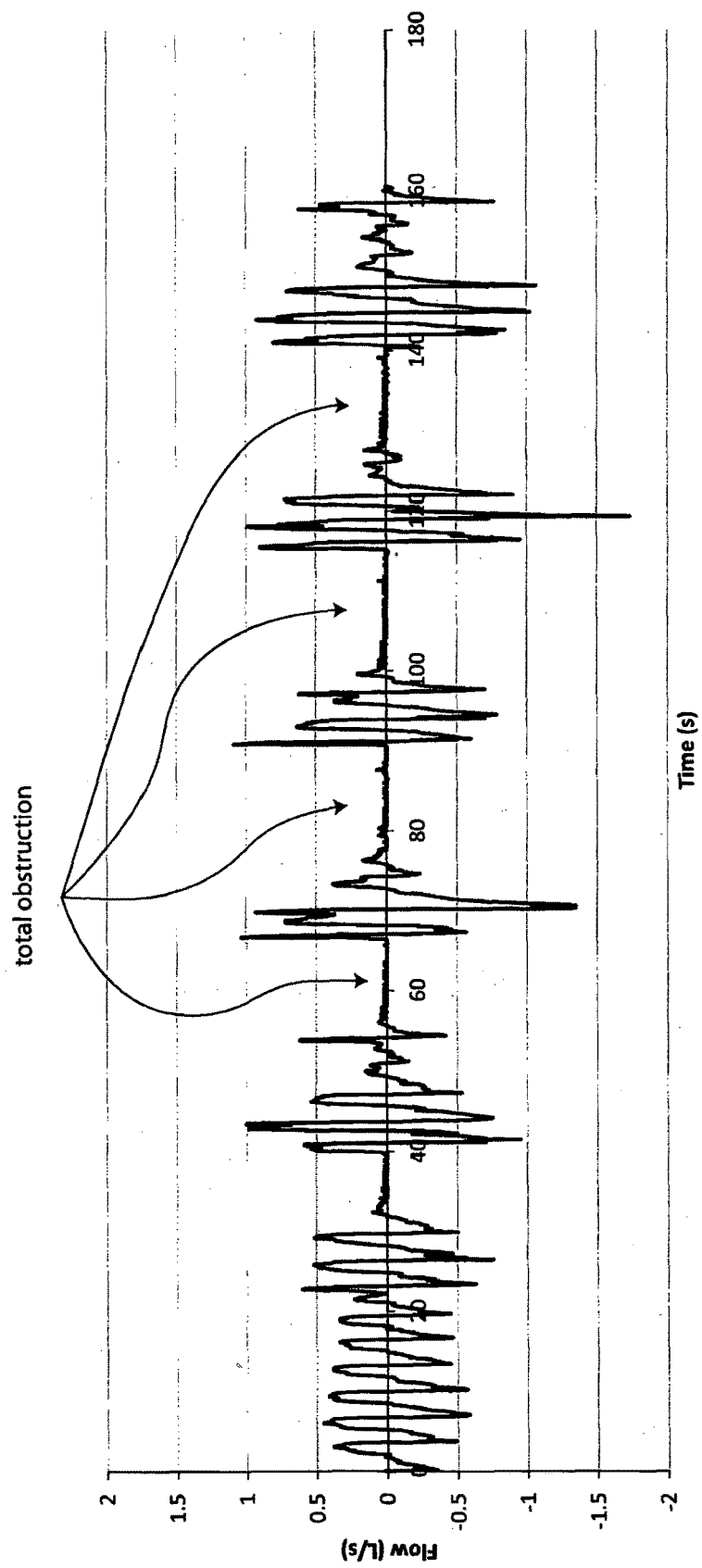

FIG. 6d shows patient flow data where the patient is experiencing a series of total obstructive apneas. The duration of the recording is approximately 160 seconds. Flow ranges from about +1 L/s to about −1.5 L/s. Each apnea lasts approximately 10-15 s.

Figure 6E:
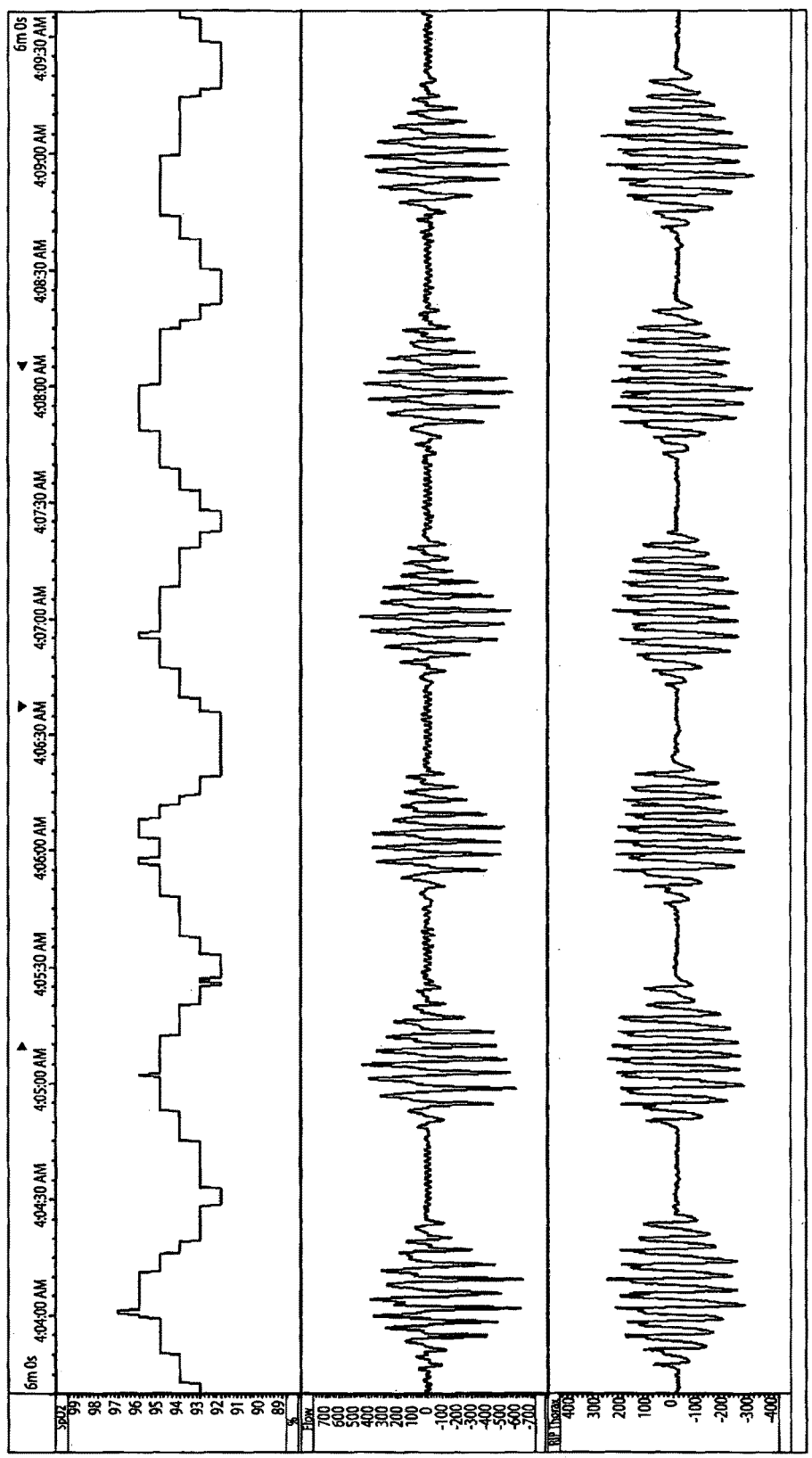

FIG. 6e shows a patient with Cheyne-Stokes respiration. There are three channels—oxygen saturation ($SpO_2$), a signal indicative of flow, and the third, a signal indicative of movement. The data span six minutes. The signal representative of flow was measured using a pressure sensor connected to nasal cannulae. The patient exhibits apneas of about 22 seconds alternating with hyperpneas of about 38 seconds. The higher-frequency, low-amplitude oscillation occurring during each apnea is cardiogenic.

Monitoring Apparatus

Figure 7A:
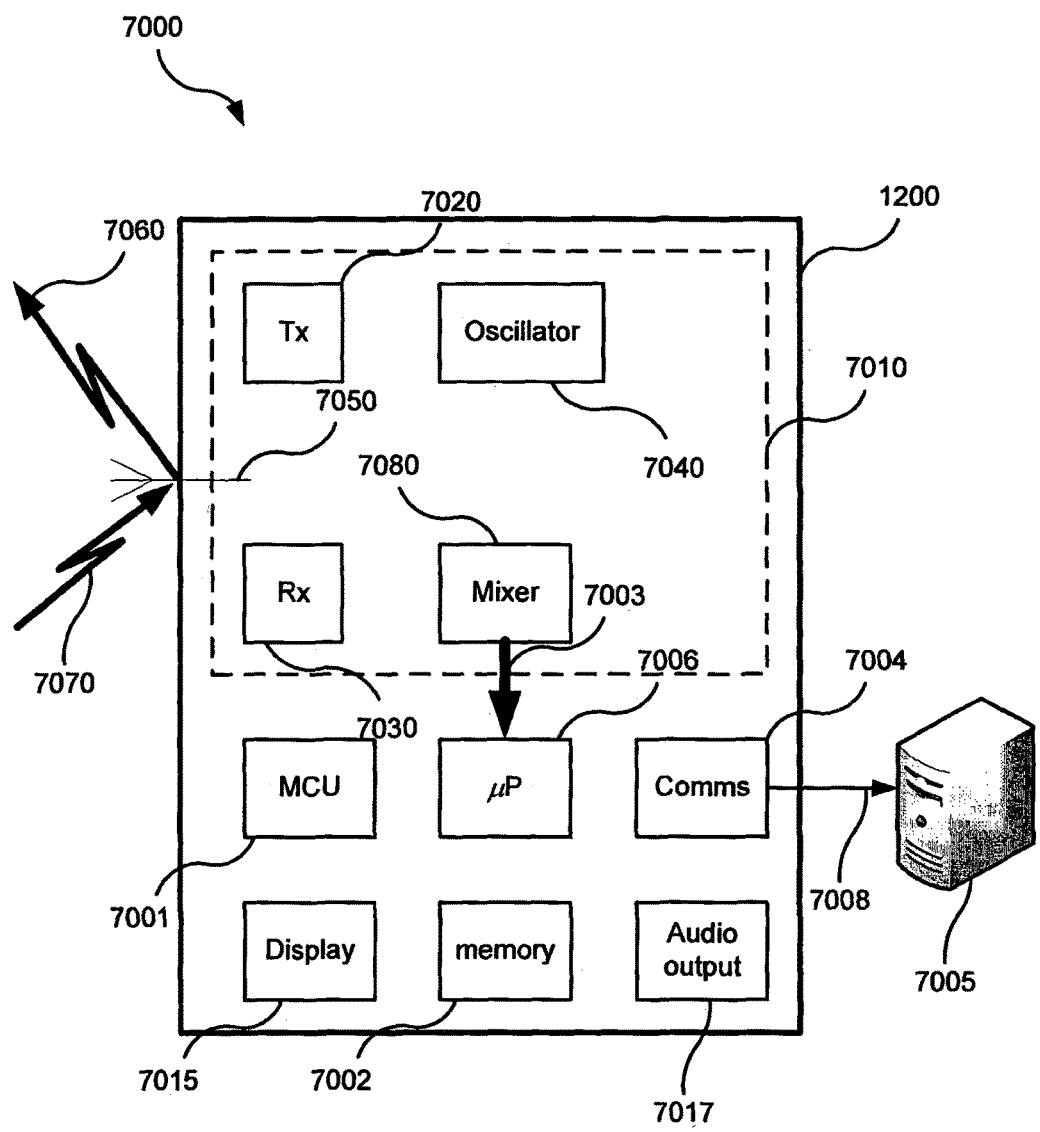

FIG. 7a is a block diagram illustrating an apparatus, including the contactless sensor unit of FIG. 1b, for monitoring the cardio-pulmonary health of a patient.

Figure 7B:
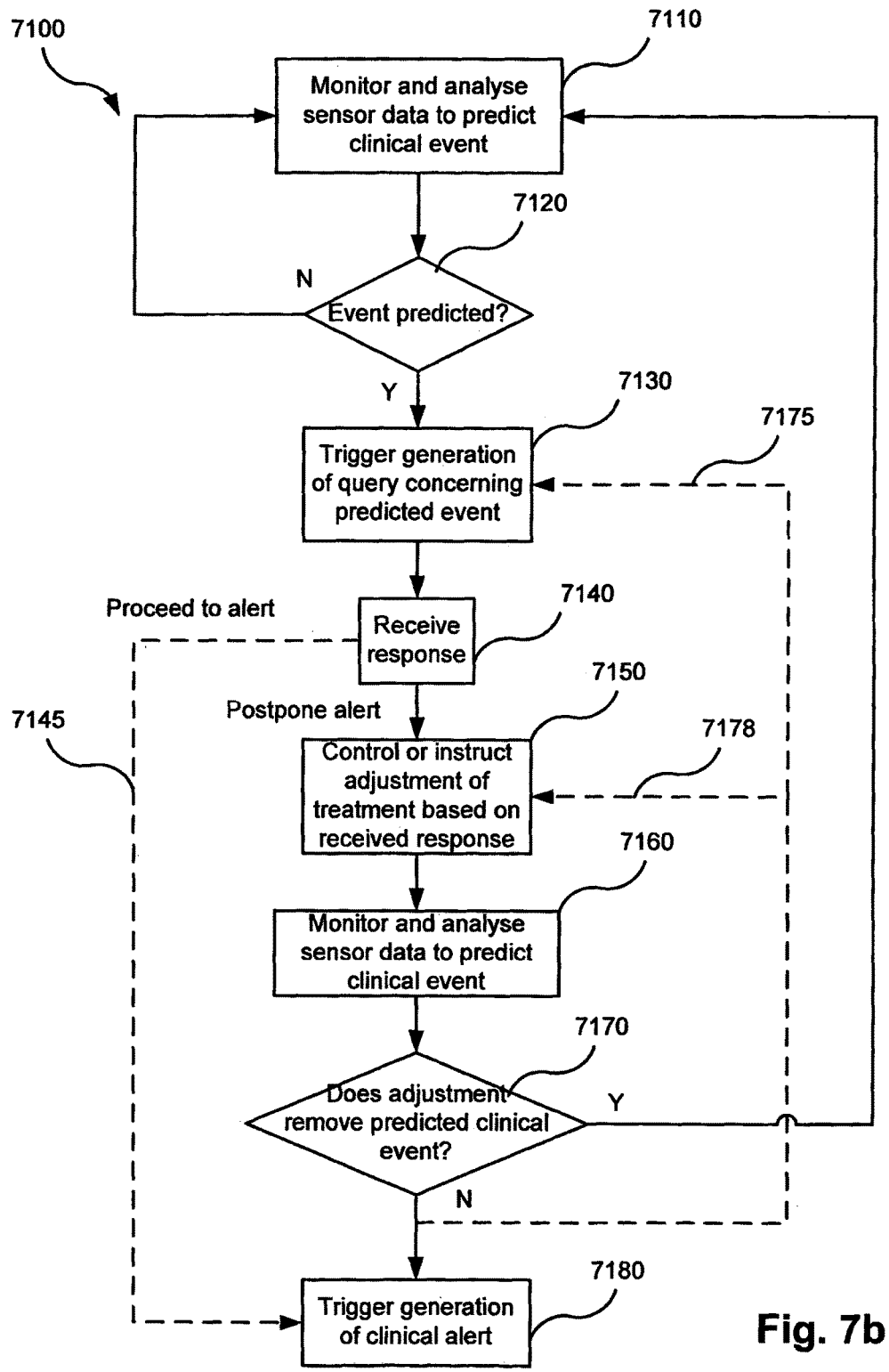

FIG. 7b is a flow chart illustrating a method of monitoring the cardio-pulmonary health of a patient, as carried out by the monitoring apparatus of FIG. 7a.

Figure 7C:
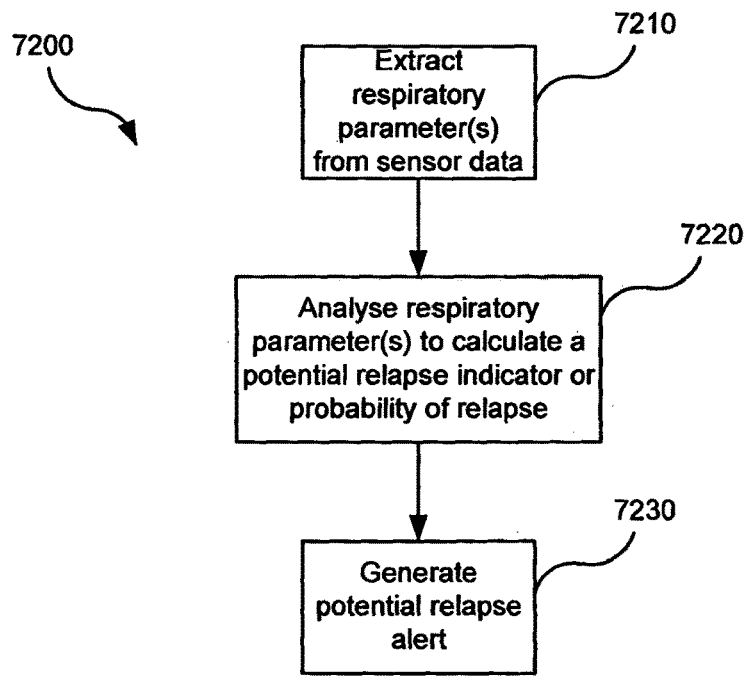

FIG. 7c is a flow chart illustrating a method of monitoring the cardio-pulmonary health of a patient, as implemented within the monitoring apparatus of FIG. 7a.

Figure 7D:
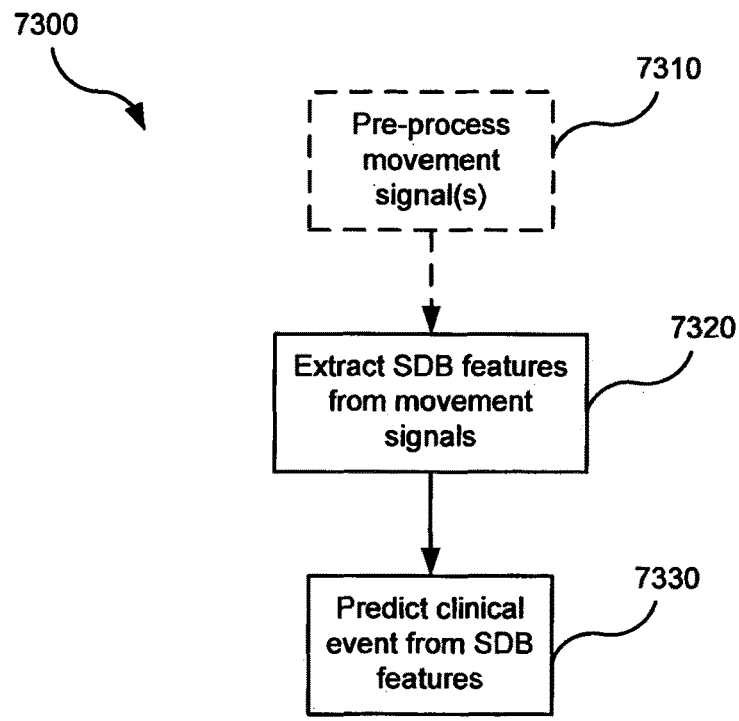

FIG. 7d is a flow chart illustrating the example steps in a method of predicting clinical events from signals representative of patient movement, as may be used in the method of FIG. 7b or FIG. 7c.

Figure 7E:
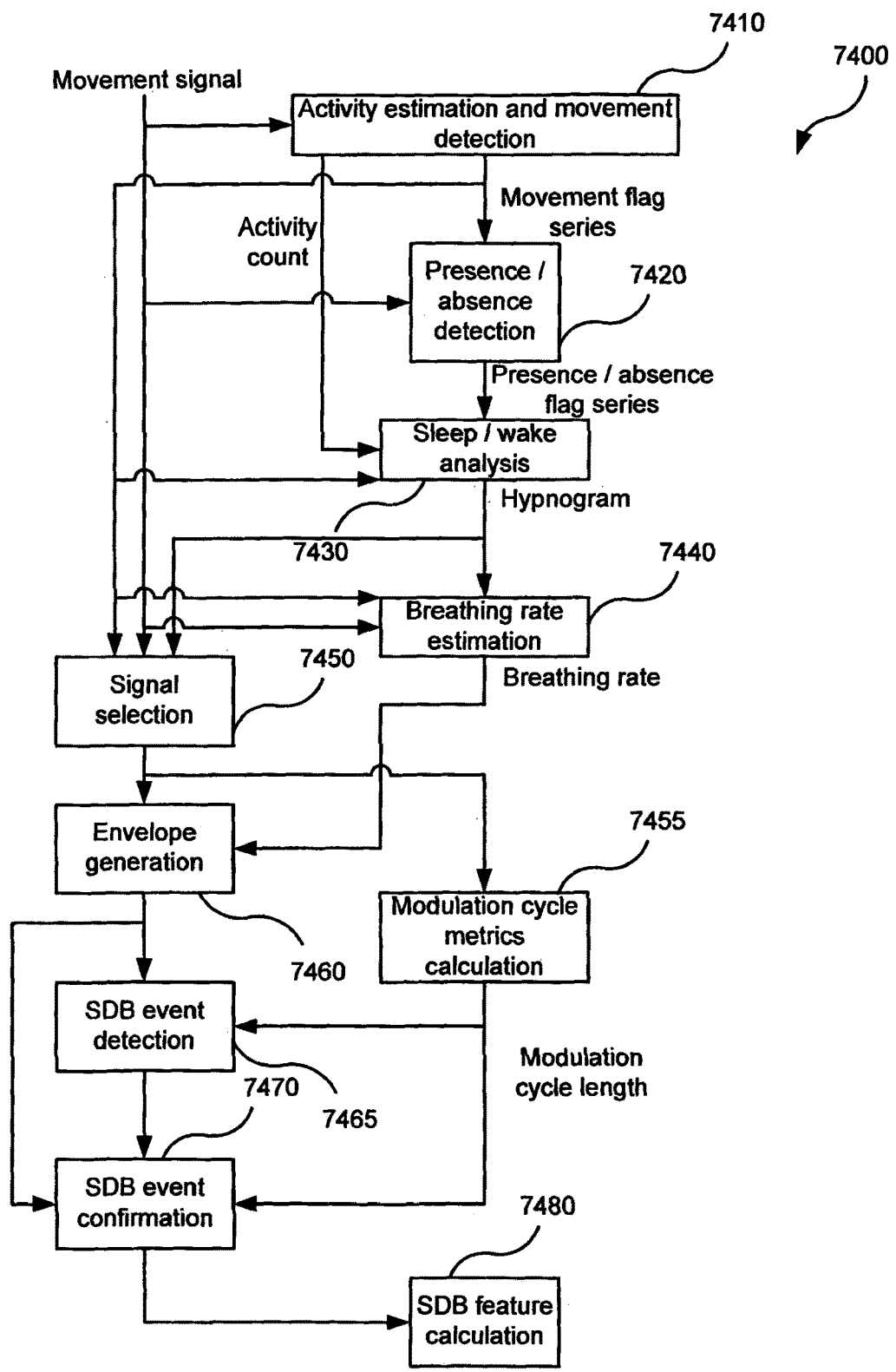

FIG. 7e is a block diagram illustrating the example modules that may serve to implement making up the feature extraction step in the method of FIG. 7d and their relationship under the combined or single-channel approach in one form of the present technology.

Figure 7F:
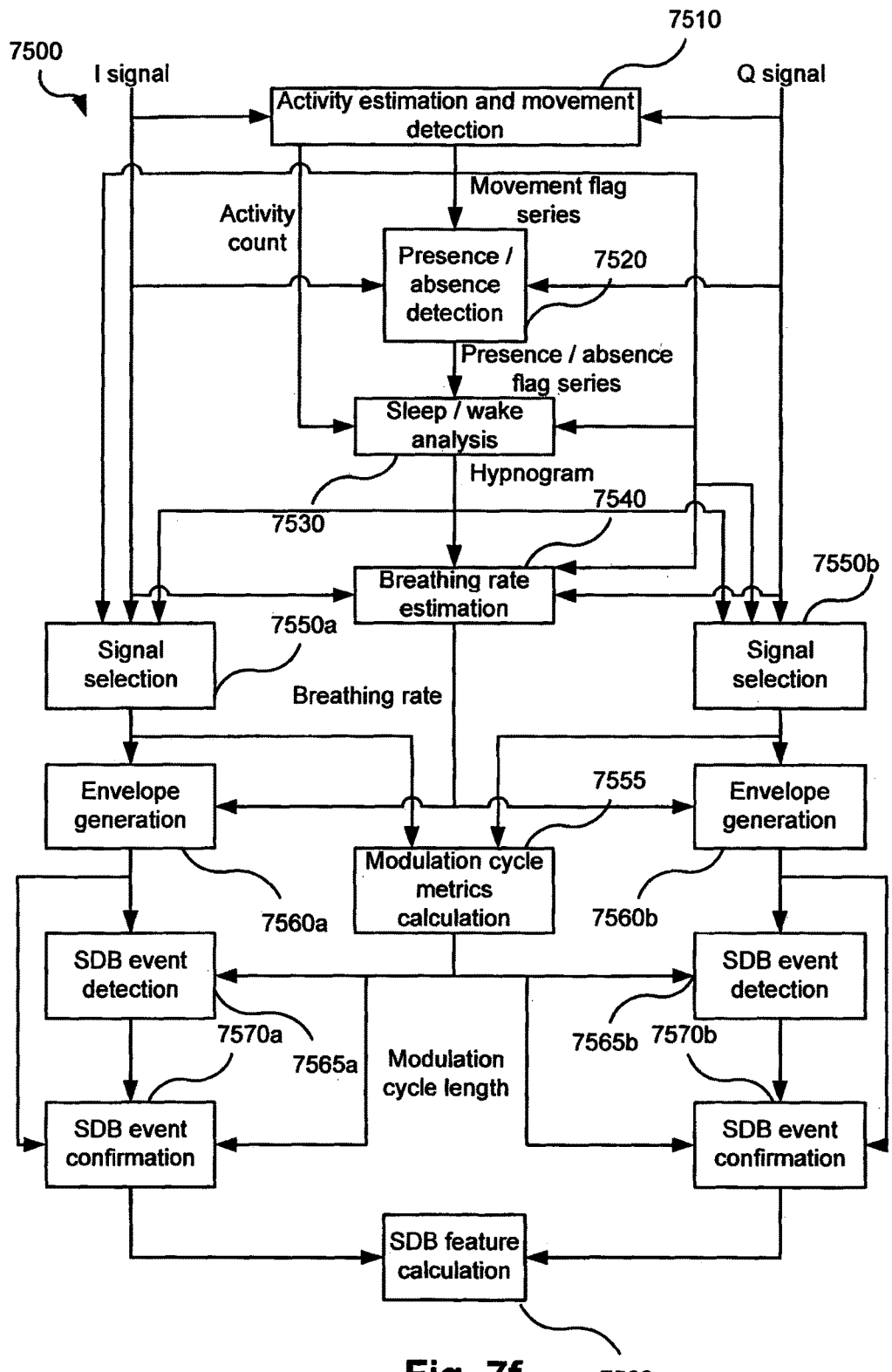

FIG. 7f is a block diagram illustrating the example modules making up that may serve to implement the feature extraction step in the method of FIG. 7d and their relationship under the hybrid approach in one form of the present technology.

FIG. 7g illustrates Lotjonen pattern expansion as applied during one implementation of the sleep/wake analysis module of FIGS. 7e and 7f.

Figure 7H:
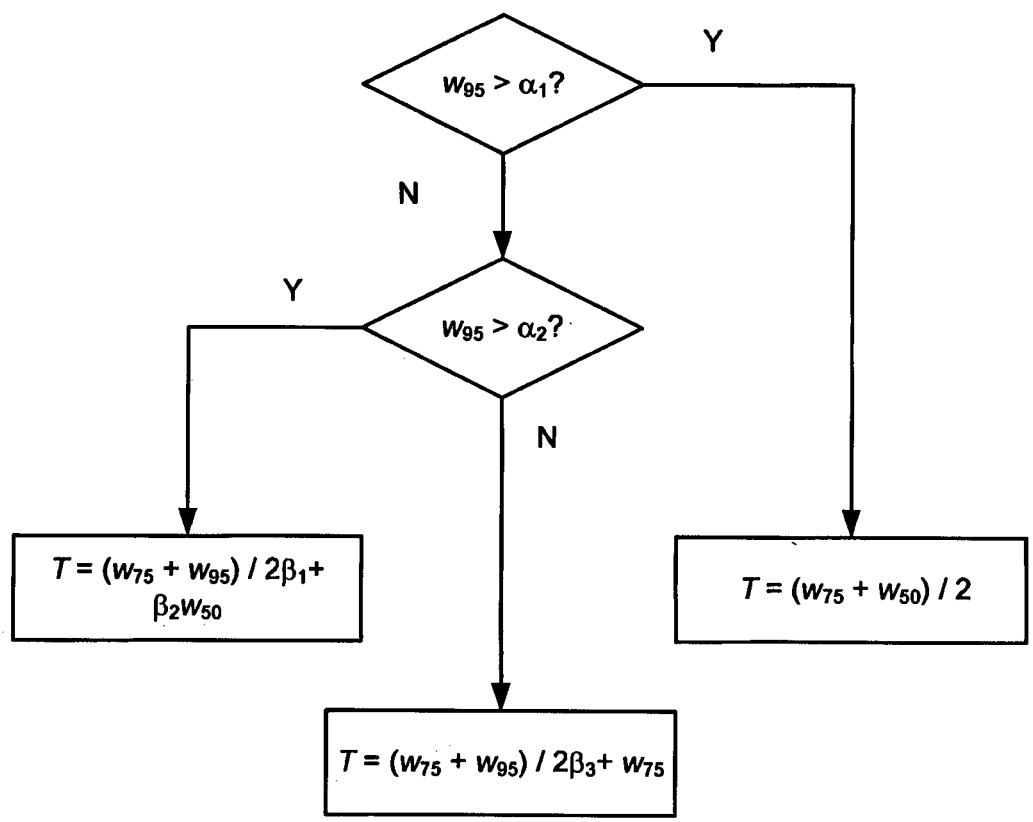

FIG. 7h is a flow chart illustrating a method of setting a waveform length threshold in an alternative implementation of the sleep/wake analysis module of FIGS. 7e and 7f.

Figure 7I:
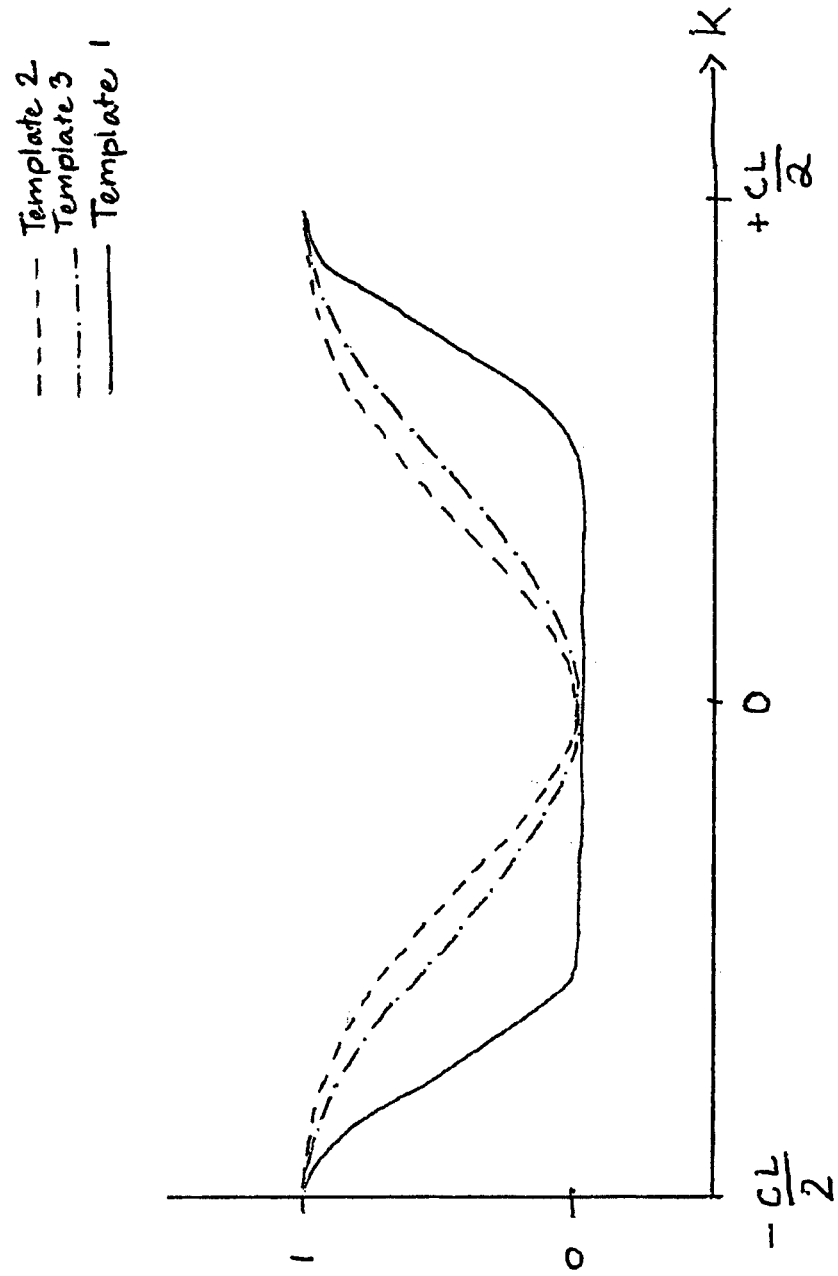

FIG. 7i contains illustrations of examples of three generic SDB respiratory effort reduction templates.

Figure 7J:
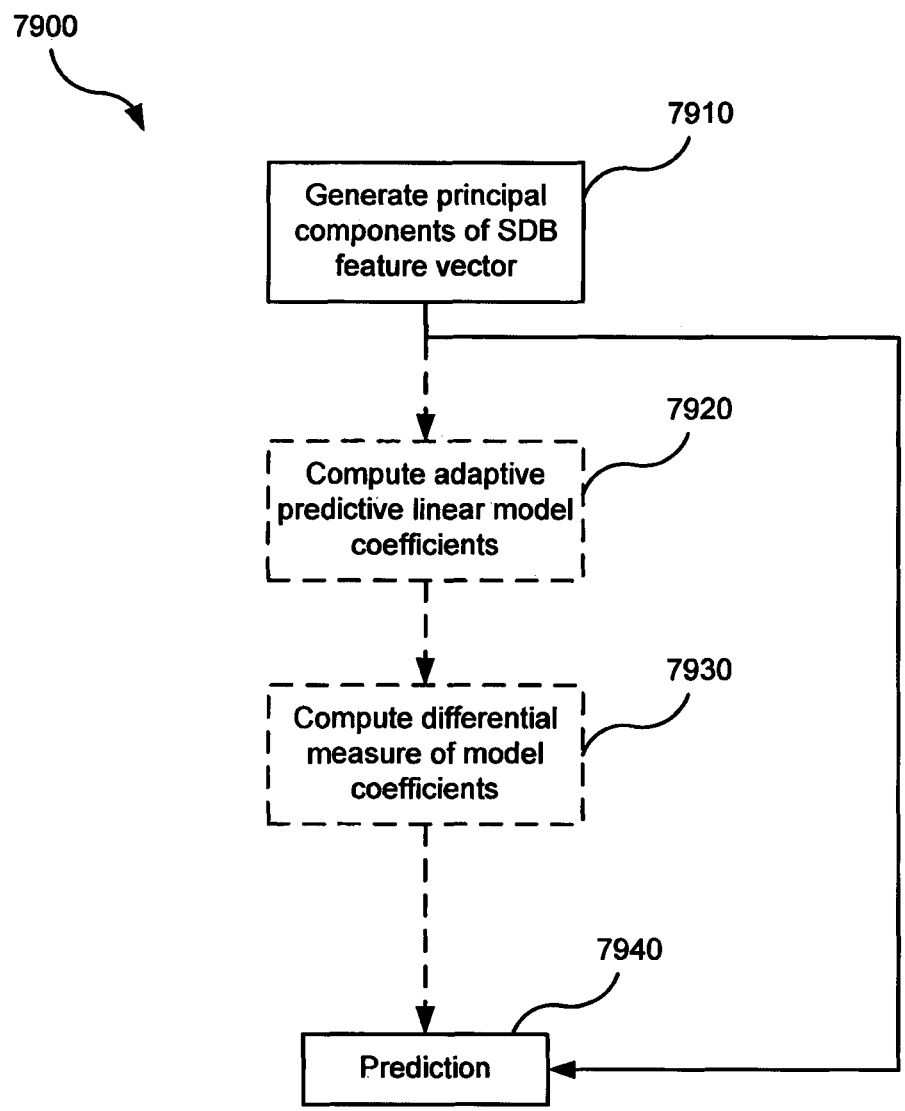

FIG. 7j is a flow chart illustrating a method that may be used to implement of the prediction step of the method of FIG. 7d.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

Treatment Systems

In one form, the present technology comprises apparatus for treating a cardio-pulmonary disorder. The treatment apparatus may comprise a PAP device 4000 for supplying pressurised respiratory gas, such as air, to the patient 1000 via an air delivery tube leading to a patient interface 3000.

Therapy

In one form, the present technology comprises a method for treating a respiratory disorder comprising the step of applying positive pressure to the entrance of the airways of a patient 1000.

PAP Device 4000

A PAP device 4000 in accordance with one aspect of the present technology comprises mechanical and pneumatic components 4100, electrical components 4200 and is programmed to execute one or more processes 4300. The PAP device preferably has an external housing 4010, preferably formed in two parts, an upper portion 4012 of the external housing 4010, and a lower portion 4014 of the external housing 4010. In alternative forms, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

Humidifier 5000

In one form of the present technology there is provided a humidifier 5000 comprising a water reservoir 5110, and a heating plate 5120.

Monitoring Apparatus 7000

In one form, the present technology comprises apparatus 7000 for monitoring the cardio-pulmonary health of a patient. The apparatus 7000 comprises a contactless sensor unit 1200 positioned adjacent and relatively close to a sleeping patient 1000 (e.g. on a bedside table), as illustrated in FIG. 1b.

Heart failure has been shown to be highly correlated with sleep disordered breathing (SDB). In particular, Cheyne-Stokes respiration (CSR), an example of which is illustrated in FIG. 6e, is caused in general by an instability in the body's respiratory control system, one cause of which is heart failure. In addition, features indicative of the severity of OSA such as the Apnea/Hypopnea Index (AHI) have been shown to be independent predictors of death by, and hospitalization for, ADHF events. Therefore, one approach to predicting ADHF events is to use features that indicate the severity of sleep disordered breathing, i.e. SDB features. One example of SDB features may be a set of features that indicate the extent to which respiration during sleep resembles classic CSR, i.e. "Cheyne-Stokes-like" features. The values of and changes in such SDB features may contain useful information about the likelihood of ADHF events. The disclosed monitoring apparatus 7000 is therefore configured to extract and analyse features indicative of the severity of sleep disordered breathing of the patient 1000, i.e. SDB features. In some cases, such features may be determined in accordance with any of the methodologies described in International Publication Number WO 2006/066337 filed on 21 Dec. 2005.

Moreover, Cheyne-Stokes respiration features may also be a short term marker of changes during the acute phase of a decompensation event of a heart failure patient (a decompensation event occurs when the compensatory mechanisms that the heart uses to maintain adequate cardiac output, are no longer sufficient—these decompensations can lead to a rapid worsening of symptoms and often require hospitalization). The medical response to a decompensation is often to temporarily increase diuretic use, and hence remove excess fluid. This can cause consequent changes in the breathing parameters, and hence the "Cheyne-Stokes-like" features described above could be used for assessing short-term effectiveness of treatments. As a specific example, the modulation cycle length of the Cheyne-Stokes respiration can be correlated with the circulation delay of the body (e.g., see Dai Yumino and T. Douglas Bradley "Central Sleep Apnea and Cheyne-Stokes Respiration", Proceedings of the American Thoracic Society, Vol. 5, No. 2 (2008), pp. 226-236.) and hence be used as a prognostic marker.

Components

FIG. 7a is a block diagram illustrating an apparatus 7000, including the contactless sensor unit 1200 of FIG. 1b, for monitoring the cardio-pulmonary health of a patient 1000 in more detail according to one form of the present technology. In the apparatus 7000, the contactless sensor unit 1200 includes a contactless motion sensor 7010 generally directed toward the patient 1000. The motion sensor 7010 is configured to generate one or more signals representing bodily movement of the patient 1000, from which may be obtained one or more signals representing respiratory movement of the patient.

The sensor unit 1200 may also include a microcontroller unit (MCU) 7001, memory 7002 (e.g. a memory card) for logging data. In one implementation, the sensor unit 1200 includes communications circuitry 7004 configured to transfer data to an external computing device 7005, e.g. a local general purpose computer, or a remote server, via a connection 7008. The connection 7008 may be wired or wireless, in which case the communications circuitry 7004 has wireless capability, and may be direct or indirect via a local network or a wide-area network such as the Internet (not shown).

The sensor unit 1200 includes a processor 7006 configured to process the signals generated by the motion sensor 7010 as described in detail below.

The sensor unit 1200 includes a display device 7015 configured to provide visual feedback to a user. In one implementation, the display device 7015 comprises one or more warning lights (e.g., one or more light emitting diodes). The display device 7015 may also be implemented as a display screen such as an LCD or a touch-sensitive display. Operation of the display device 7015 is controlled by the processor 7006 based on an assessment of the patient's cardio-pulmonary health. The display device 7015 may be implemented to visually show information to a user of the monitoring apparatus 7000, such as a patient or a physician or other clinician. The display device 7015 may also display a graphical user interface for operation of the monitoring apparatus 7000.

The sensor unit 1200 includes an audio output 7017 configured to provide acoustic feedback to a user under the control of the processor 7006, e.g., a tone whose frequency varies with breathing, or an alarm which sounds when certain conditions are met.

User control of the operation of the monitoring apparatus 7000 may be based on operation of controls (not shown) that are sensed by the processor 7006 of the monitoring apparatus 7000.

One example of a sensor unit 1200 is the SleepMinder device manufactured by ResMed Sensor Technologies Ltd, which contains a contactless Doppler radio-frequency (RF) motion sensor 7010.

In one form of the present technology, such as when the SleepMinder device is used as the sensor unit 1200, the motion sensor 7010 includes an RF transmitter 7020 configured to transmit an RF signal 7060. The radio-frequency signal 7060 for example has the form $$s(t) = u(t)\cos(2\pi f_c t + \theta) \qquad \text{(Eq. 1)}$$

In Eq. 1, the carrier frequency is $f_c$ (typically in the range 100 MHz to 100 GHz, e.g. 3 GHz to 12 GHz, e.g. 5.8 GHz or 10.5 GHz), t is time, θ is an arbitrary phase angle, and u(t) is a pulse shape. In a continuous wave system, the magnitude of u(t) may be unitary, and can be omitted from Eq. 1. More generally, the pulse u(t) will be defined as in Eq. 2:

$$u(t) = \begin{cases} 1, t \in [kT, kT + T_p], k \in Z \\ 0, \text{otherwise} \end{cases} \qquad \text{(Eq. 2)}$$

where T is the period width, and $T_p$ is the pulse width. Where $T_p \ll T$, this becomes a pulsed continuous wave system. In one case, as $T_p$ becomes very small, the spectrum of the emitted signal becomes very wide, and the system is referred to as an ultra-wideband (UWB) radar or impulse radar. Alternatively, the carrier frequency of the RF transmitted signal 7060 can be varied (chirped) to produce a so-called frequency modulated continuous wave (FMCW) system.

The radio frequency signal 7060 may be generated by the transmitter 7020 using a local oscillator 7040 coupled with circuitry for applying the pulse gating. In the FMCW case, a voltage-controlled oscillator is used together with a voltage-frequency converter to produce the RF signal 7060 for transmission. The coupling of the transmitted RF signal 7060 to the air may be accomplished using an antenna 7050. The antenna 7050 can be omnidirectional (transmitting power more-or-less equally in all directions) or directional (transmitting power preferentially in certain directions). It may be advantageous to use a directional antenna 7050 in the apparatus 7000 so that transmitted and reflected energy are primarily coming from one direction. In one implementation of the apparatus 7000, a single antenna 7050 is used for both the transmitter 7020 and the receiver 7030, with a single carrier frequency. Alternatively, multiple receive and transmit antennas 7050 can be used, with multiple carrier frequencies.

The apparatus 7000 is compatible in various embodiments with various types of antenna 7050 such as simple dipole antennas, patch antennas, and helical antennas, and the choice of antenna can be influenced by factors such as the required directionality, size, shape, or cost. It should be noted that the apparatus 7000 can be operated in a manner which has been shown to be safe for human use. The apparatus 7000 has been demonstrated with a total system emitted average power of 1 mW (0 dBm) and lower. The recommended safety level for RF exposure is 1 mW/cm$^2$. At a distance of 1 meter from a system transmitting at 0 dBm, the equivalent power density will be at least 100 times less than this recommended limit.

In use, the transmitted RF signal 7060 is reflected off objects that reflect radio waves (such as the air-body interface of the patient 1000), and some of the reflected signal 7070 will be received at a receiver 7030, which can be collocated with the transmitter 7020, or which can be separate from the transmitter 7020, in a so-called "bistatic" configuration. The received signal 7070 and the transmitted signal 7060 can be multiplied together in a mixer 7080 (either in an analog or digital fashion). This mixer 7080 can be of the form of a multiplier (as denoted below in (Eq. 3)) or in a circuit which approximates the effect of a multiplier (e.g., an envelope detector circuit which adds sinusoidal waves). For example, in the CW case, the mixed signal will equal $$m(t) = \gamma \cos(2\pi f_c t)\cos(2\pi f_c t + \phi(t)) \quad \text{(Eq. 3)}$$

where $\phi(t)$ is a phase term resulting from the path difference of the transmitted and received signals 7060 and 7070 (in the case where the reflection is dominated by a single reflective object), and y is the attenuation experienced by the reflected signal 7070. If the reflecting object is fixed, then $\phi(t)$ is fixed. In the apparatus 7000, the reflecting object (e.g., the chest of the patient 1000) is in general moving, and $\phi(t)$ will be time-varying. As a simple example, if the chest is undergoing a sinusoidal motion of frequency $f_m$ due to respiration, then the mixed signal m(t) contains a component at $f_m$ (as well as a component centred at $2f_c$ which can be simply removed by low pass filtering). The signal at the output of the low pass filter after mixing is referred to as the raw or demodulated sensor signal 7003, and contains information about gross bodily (non-respiratory) movement, and respiratory movement.

The amplitude of the demodulated sensor signal 7003 is affected by the mean path distance of the reflected signal, leading to detection nulls and peaks in the sensor 7010 (areas where the sensor is less or more sensitive). This effect can be minimised by using quadrature techniques in which the transmitter 7020 simultaneously transmits a signal 90 degrees out of phase (in quadrature) with the signal 7060 of Eq. 1. This results in two reflected signals, both of which can be mixed and lowpass filtered by the mixer 7080, leading to two demodulated sensor signals 7003a (the "I signal") and 7003b (the "Q signal") in respective I- and Q-"channels".

In the UWB implementation, an alternative method of acquiring a demodulated sensor signal 7003 may be used. The path distance to the most significant air-body interface can be determined by measuring the delay between the transmitted pulse and peak reflected signal. For example, if the pulse width is 1 ns, and the distance from the sensor 7010 to the body is 0.5 meters, then the delay before a peak reflection of the pulse arrives at the receiver 7030 will be $1/(3 \times 10^8)$ s=3.33 ns. By transmitting large numbers of pulses (e.g., a 1 ns pulse every 1 μs) and assuming that the path distance is changing slowly over a given period, a demodulated sensor signal 7003 may be computed as the average of the time delays over that period.

In this way, the motion sensor 7010, e.g., a radio-frequency sensor, can estimate the respiratory movement of the chest wall, or more generally the movement of the part of the body of the patient 1000 whom the apparatus 7000 is monitoring.

As mentioned above, the received signal 7070 can include large motion artefacts, e.g. as the result of gross bodily movement. This is due to the fact that the reflected signals from the body can contain more than one reflection path, and lead to complex signals (for example if one hand is moving towards the sensor, and the chest is moving away). The reception of such signals is useful as it can indicate that the upper body is in motion, which is useful in determining sleep state. The sensor can also be used to detect motion of a lower part of the body (such as involuntary leg jerks) of a patient 1000, which are useful in the diagnosis of sleep disorders such as Restless Legs Syndrome or Periodic Limb Movements.

In order to improve the quality of the respiratory movement signal, and more general bodily movement signals, the physical volume from which reflected energy is collected by the sensor unit 1200 can be restricted using various methods. For example, the sensor unit 1200 can be made "directionally selective" (that is, it transmits more energy in certain directions), as can the antenna of the receiver 7030. Directional selectivity can be achieved using directional antennas 7050, or multiple RF transmitters 7020. In alternative forms of the present technology, a continuous wave, an FMCW, or a UWB radar is used to obtain similar signals. A technique called "time-domain gating" can be used to only measure reflected signals 7070 which arise from signals at a certain physical distance from the sensor unit 1200. Frequency domain gating (filtering) can be used to ignore motions of the reflected object above a certain frequency.

In implementations of the apparatus 7000 using multiple frequencies (e.g., at 500 MHz and 5 GHz), the lower frequency can be used to determine large motions accurately without phase ambiguity, which can then be subtracted from the higher-frequency sensor signals (which are more suited to measuring small motions). Using such a sensor unit 1200, the apparatus 7000 collects information from the patient 1000, and uses that information to determine respiratory movement, and more general bodily movement information.

Other contactless motion sensors, e.g. infrared sensors, ultrasound sensors, optical sensors, or contact motion sensors, such as piezoelectric sensors or respiratory inductance plethysmographs, may be used as additional motion sensors to, the contactless motion sensor 7010, either as part of the sensor unit 1200, or as part of a separate sensor unit. Such additional motion sensors need to be positioned relative to the patient 1000 in accordance with the characteristics of the respective motion sensors. For example, if the motion sensor is a respiratory inductance plethysmograph, the sensor may be positioned around the chest or abdomen of the patient 1000. If the motion sensor is a piezoelectric sensor, or a direct air-mat pressure sensor, such a sensor may be positioned under the mattress of the patient 1000.

In certain implementations, one or more contactless non-motion sensors configured to provide data relevant to the cardio-pulmonary health of the patient 1000 may be incorporated into the apparatus 7000 to enhance overall accuracy or provide additional robustness. One example of a contactless non-motion sensors is a sound sensors. The characteristic sound patterns associated with sleep apnea may be analysed and used to enhance the accuracy of the generated summary measures of SDB. The system described by Karunajeewa A. S., Abeyratne U. R., Hukins C. in "Silence-breathing-snore classification from snore-related sounds", Physiol. Meas. 29(2):227-43 (February 2008), is one example of acoustic-based screening for SDB, and such techniques could be readily incorporated into with the apparatus 7000 to provide a useful and robust tool for monitoring cardio-pulmonary health. The advantage of such incorporation is that the respiratory movement signal may be occasionally unusable due to excessive motion artefacts. At such times, the acoustic signal may provide reasonable estimates of respiratory parameters. Conversely, the acoustic signal may sometimes be unusable due to background noise contamination, at which times respiratory movement takes over as the primary sensor modality.

In still other implementations, the apparatus 7000 may incorporate one or more contact non-motion sensors configured to provide data relevant to the cardio-pulmonary health of the patient 1000. Examples of such contact sensors include an oximeter (which measures blood oxygen levels), an oronasal cannula (which directly measures respiratory airflow), and an electrocardiogram (ECG) monitor. An ECG monitor may be configured to detect cardiac-related characteristics such as a heart rate and may also determine respiratory parameters (such as central or obstructive apneas, hypopneas, etc.) Optionally, these parameters may be computed by the processor 7006 based on ECG data transmitted to the processor 7006, or they may be computed by the ECG monitor and be transmitted to the processor 7006. The oximetry sensor highlighted above has the advantage that it can also provide a respiratory effort signal; such a signal can be derived from the underlying photoplethysmogram (PPG) component of the oximeter by tracking the peak and trough values of the PPG.

Further parameters of clinical significance relate to the position and orientation of the patient. It has been shown that rostral fluid shift can affect the incidence of central and obstructive events (see e.g., "Role of nocturnal rostral fluid shift in the pathogenesis of obstructive and central sleep apnoea". White L H, Bradley T D. J Physiol. 2013 Mar. 1; 591). In practice, heart failure patients are also intuitively aware of this phenomenon and often use pillows to prop themselves up at an angle to reduce fluid build-up and hence enhance ease of breathing during sleep. Furthermore, the likelihood of obstructive events is often dictated by position (e.g., many patients experience more obstructive events when on their back than on their sides). Therefore, in one embodiment of the system described herein, one or more three-dimensional accelerometers can be worn by the patient which can provide information about their angle of recline, and their bodily position (supine, on left, on right, or prone). This information can be combined with the measured respiratory parameters to provide further insight into the patient status.

The processor 7006 of the sensor unit 1200, or that of the external computing device 7005, processes the signals 7003 acquired from the sensors, e.g. the motion sensor(s) 7010, as described in detail below. The instructions for the described processing may be stored on a computer-readable storage medium, e.g. the memory 7002 of the sensor unit 1200, and interpreted and executed by a processor, e.g. the processor 7006 of the sensor unit 1200. In some forms of the present technology, the processing may be carried out in "batch mode", i.e. the acquired signals 7003 are stored, either in memory 7002 of the sensor unit 1200 or in that of the external computing device 7005, for one or more complete monitoring sessions, and subsequently processed in a single batch. In one implementation, each monitoring session is one night in duration. In other forms of the present technology, the processing may be carried out in "real time" during the monitoring session.

It should be noted that while the functionality of the monitoring apparatus 7000 is described below as controlled by the sensor unit 1200, in other implementations the external computing device 7005 may implement the described functionality, based on data transmitted to it by the sensor unit 1200 and any other sensors in the apparatus 7000 as described above. In such implementations, the above descriptions of the visual display 7015 and the audio output 7017 apply equally to comparable elements of the external computing device 7005. In one example, the external computing device 7005 is clinician-accessible apparatus such as a multi-patient monitoring system that allows a clinician to review data from remote patient data recording devices such as the monitoring apparatus 7000. In these systems, a database may be provided to record patient monitoring data. Through such an external computing device 7005, clinicians may receive a report or alert that the patient may require closer observation or should be brought to hospital.

Processes

The processor 7006 executes processes 4300 to monitor the patient's cardio-pulmonary health from data received from the sensor unit 1200 and any other sensors described above.

Clinical Alerts

The processes 4300 may be carried out to monitor the patient 1000 before, during, and after hospitalization. For example, heart failure and COPD patients may suffer from exacerbation or decompensation (ADHF) events. These "clinical events" may require modifications to medical treatment. Untreated exacerbation could lead to further exacerbation and potentially require hospitalization for the patient. However, if exacerbation is discovered early enough, such as at the earliest stages of its onset, it may be treated in a manner that may avoid (re-)hospitalization.

In one form of the present technology, the processor 7006 analyses the processed or received sensor data to trigger generation of a clinical alert based on features related to cardio-pulmonary health extracted from the sensor data. Additional examples of such analysis, which may include evaluation of one or more change condition indicators, are described in U.S. patent application Ser. No. 12/751,174, filed on Mar. 31, 2010 and U.S. patent application Ser. No. 12/483,357, filed on Jun. 12, 2009, the entire disclosures of which are incorporated herein by cross reference.

Optionally, the clinical alert may include a warning or alert message taking a number of forms. For example, the processor 7006, to generate a clinical alert, may activate a status light (e.g., an LED or an icon on the display device 7015) of the monitoring apparatus 7000. A more detailed message concerning the assessment of the indicator may also be displayed on the display device 7015. Optionally, the processor 7006 may also, or alternatively, send an alert message to an external computing device 7005 associated with a clinician via the connection 7008. Such a message may take the form of a wired or wireless communication. For example, the processor 7006 may generate an alert message via a paging system such as by automatically dialing a paging system. The processor 7006 may also be configured to generate an automated voice phone call message. The processor 7006 may also send the alert message by a fax transmission. In some embodiments, the processor 7006 may also send an alert message via any internet messaging protocol, such as an email message, or by any other internet data file transport protocol. The alert messages may even be encrypted to keep patient information confidential. A typical alert message may identify the patient. Such a message may also include data recorded by the monitoring apparatus 7000 or any other recorded patient information. Optionally, in some embodiments, the alert message may even express that the patient should be considered for additional treatment, hospitalization, or an evaluation due to the detection of a potential ADHF event or exacerbation of COPD.

While alert messages may be directed by the processor 7006 to the patient via the display device 7015 of the monitoring apparatus 7000 and/or the clinician via the connection 7008, in some embodiments, the alert messages could be directed more selectively. For example, a first alert message may be only transmitted to a clinician by only transmitting the alert message to an external computing device 7005 through the connection 7008 without showing any alert on the display device 7015. However, a second alert message, which may be a more urgent message, could then be actively displayed on the display device 7015 in addition to being transmitted to the external computing device 7005. An audible alarm from an optional speaker controlled by the processor 7006 may also be implemented. Use of an audible alarm may depend on the urgency of the alert message.

Queries

In another form of the present technology, the processor 7006 may condition an alert on input responses to a patient query that may serve to avoid unnecessary alerts. For example, based on an analysis of sensor data by the monitoring apparatus 7000 (e.g., a comparison of one or more respiratory parameters with one or more thresholds) the processor 7006 may trigger a presentation of a patient query to the patient to prompt the patient for input based on the assessment made by the processor. In such a case, the display device 7015 under control of the processor 7006 may present a query to the patient, prompting the patient to input additional information via a user interface. The presented question or questions of the query may be selected from a database, or other data structure of questions, such as a data structure in a memory of the apparatus, such that the selected questions are particularly associated with a pattern detected by the processor in the analysis. The processor 7006 may then further evaluate data of the received responses to the query. Based on this further evaluation, the processor 7006 may trigger an alert message, refrain from triggering an alert message, and/or delay a triggering of an alert message pending responses to one or more additional triggered queries. Such additional queries may be triggered after a certain time, after a further detected pattern or after a further use of the monitoring apparatus 7000.

For example, when monitoring a heart failure patient for imminent acute decompensated heart failure (ADHF) events or a COPD patient for exacerbations, it may be desirable to query the patient to qualify a pattern detection made by the processor 7006. Such queries may serve to reduce false positives (e.g., when the processing flags a need for clinical contact and the clinical contact is later found to have been unnecessary). This type of false positive may be due to changes in patient behavior, which may be corrected without medical intervention. Such behaviors may include missed or incorrect dosage of medication, non-compliance with dietary instructions and/or rest requirements, and the like.

For example, in some embodiments, in an effort to minimize false positives, the processor 7006 may detect a respiratory pattern or potential clinical events that might require a clinical alert (e.g., a certain number of SDB events over a certain period of time that may be indicative of COPD exacerbation and/or ADHF). Based on the detected pattern or events, the processor 7006 may present one or more questions in a query to the patient on a user interface of the apparatus 7000. Such questions may address pharmaceutical and/or lifestyle compliance by the patient (e.g., has the patient been taking prescribed medication and/or following physician's treatment advice, etc.). Optionally, in some cases, one or more questions may address the operational integrity of the monitoring apparatus 7000 to ensure that the collected data is valid. Optionally, the processor 7006 may pursue a series of queries over a predetermined span of time (such as one or more monitoring sessions or nights of sleep) and generate a clinical alert only after the predetermined span of time has elapsed.

For example, if a recurring respiratory pattern (such as one repeatedly detected in several monitoring sessions) indicates a likelihood of a clinical event, the processor 7006 may prompt a series of queries to the patient regarding diet that might have a causal relationship with the recurring pattern. If the patient is not in compliance with the dietary requirements as determined by the patient's responses input to the monitoring apparatus 7000, the processor 7006 may then continue to monitor and query the patient again after a further monitoring time period has elapsed (e.g., query the patient after a number of minutes, hours, or days). If the processor 7006 detects a continuation of the detected respiratory pattern and the patient's responses indicate that diet is not a cause (e.g., the patient responds to a subsequent query that he or she is now in compliance with the dietary requirements), the processor 7006 may then trigger a clinical alert message to a clinician via a notification infrastructure (e.g., tele-monitoring) to notify a clinician directly as described below. In some cases, a certain received response(s) to one or more questions of the query may alternatively rule out the triggering of such an alert message. For example, a query and response may determine that the patient was not wearing his or her mask and as a result, the processor 7006 may refrain from triggering an alert.

The technology described above may be further illustrated with the following example. A heart failure patient does not take the prescribed diuretics for a period of time. Due to noncompliance, the patient experiences dyspnea and breathing irregularities at night. The processor 7006 of the monitoring apparatus 7000 may detect such events, or a pattern of such events, which may be indicative of an imminent decompensation or exacerbation event. Instead of directly issuing a clinical alert to the clinician, the monitoring apparatus 7000 may trigger a query to the patient (e.g., via display device 7015) to determine whether the patient has taken the prescribed diuretics. The evaluation of the response may trigger a message to the patient, rather than an alert to a clinician, to remind the patient to take the medication if the input answer is negative. After a period of time, such as twenty-four hours, the processor 7006 of the monitoring apparatus 7000 may then further evaluate the breathing patterns of the patient to see if the pattern recurs or has been resolved (by taking of the diuretics). An alert message would not be generated if the processor 7006 does not detect the previously detected respiratory pattern that triggered the initial query. Optionally, the processor 7006 may also confirm by a supplemental query that the patient has taken the medication. In such cases, monitoring may resume as usual thereafter. If, however, the recurring pattern is still or again detected by the processor after the initial query, a subsequent query, such as one with different questions, may be presented to the patient on the display device 7015. After the predetermined number and frequency of queries have been performed, and the pattern is still detected by the processor 7006, the monitoring apparatus 7000 may then trigger an alert message to notify the clinician of an imminent clinical event. In this manner, the processor may be configured to dispose of simple cases of non-compliance (such as dietary or exercise) or explain apparatus malfunctions due to, for example, unintentional disconnections or power loss, without the need for a clinical alert message requesting that the patient be contacted.

In one example, the processor 7006 may access the memory 7002 that includes a set of queries. Each question of a query may be associated with one or more detectable respiratory patterns or events. A question may be broad (e.g., "has patient complied with the prescribed diet?") or specific (e.g., "has patient diet been fortified with potassium?"). With the set of questions indexed by such detectable patterns or events, the processor 7006 may then select a subset of questions for a query based on the detected pattern or event.

Questions may be presented in series in response to a particular monitoring session. For example, the processor 7006 may prompt two, three, four, five, six or more questions in a row so as to identify or rule out causes of the detected respiratory abnormality of the monitoring session that would or would not need an alert message. Alternatively, the processor 7006 may access an associated rank or priority for the question that represents an order of likelihood. Thus, the processor 7006 may conditionally present a series of questions according to the rank associated with each question. For example, the controller may present a first query in response to a predicted event. If in answering the first query, the patient response(s) indicates that the predicted event does not (at least yet) require an alert, the response and determination may be logged and the processor 7006 may proceed to a second monitoring session during a predetermined period of time. If the respiratory pattern is again detected, a second query of a different rank from the first query may then be triggered. This detection and querying cycle may be repeated until no further queries remain or a response to a query indicates a need for an alert, after which the processor 7006 may then trigger an alert message.

FIG. 7b is a flow chart illustrating a method 7100 of monitoring cardio-pulmonary health as implemented within the monitoring apparatus 7000 in one form of the present technology. The method 7100 is carried out by the processor 7006 of the monitoring apparatus 7000, configured by instructions stored on computer-readable storage medium such as the memory 7002.

At the first step 7110, the processor 7006 monitors and analyses data received from the sensor unit 1200 and any other sensors described above so as to predict whether a clinical event is likely to occur within a predetermined prediction horizon, as described in detail below. If at step 7120 no event is predicted ("N"), the processor 7006 may continue monitoring/analysis at 7110. If a potential clinical event is predicted at 7120 "Y"), the processor 7006 at 7130 triggers generation of one or more queries to evaluate a potential cause of the clinical event, such as by displaying them on display device 7015, as discussed in more detail herein, and/or on another processing device (e.g., tablet computer, mobile phone or other computing device etc.) in direct or indirect communication with the processor 7006. Depending on the patient input response to the query received at step 7140, the processor 7006 and/or such other processing device may proceed to step 7180 to trigger generation of a clinical alert immediately (shown as a dashed arrow 7145), or postpone the clinical alert generation by proceeding to step 7150.

At step 7150, the processor 7006 may control adjustment of a treatment in response to the received response to the patient queries. For example, the processor 7006 may modify a target ventilation, or other treatment control parameters of a PAP device 4000. Alternatively, the processor 7006 may maintain the same treatment as that provided during the monitoring/analysis step 7110, and instead issue an instructional message to instruct the patient to make an adjustment, such as a change in diet or medication or a resetting or repair of the apparatus 7000 or PAP device 4000. At the next step 7160, after a predetermined delay (e.g. 24 to 48 hours), the apparatus monitors and analyses the sensor data in similar fashion to step 7110 to determine whether the instructed or controlled adjustment of step 7150 resolved the issue previously detected at step 7110 (e.g., by determining if the predicted clinical event is still predicted). If at step 7170 the issue has been resolved (e.g., the clinical event is no longer predicted) ("Y"), the method 7100 returns to step 7110 to continue monitoring and analysing sensor data. If the clinical event is still predicted ("N"), the method 7100 may return to step 7130 or 7150 (via dashed arrows 7175 and 7178 respectively) if further queries or adjustments are available, or if not, generation of a clinical alert is triggered at step 7180 as described in more detail herein.

Relapse Monitoring

In some embodiments, the monitoring apparatus 7000 may be implemented with additional operations. For example, as previously mentioned, the monitoring apparatus 7000 may be useful to determine whether or not a hospitalized patient (e.g., a heart failure or COPD patient) is ready to be released or should not be released from the hospital. Releasing a patient too soon may not be beneficial for the patient, particularly if a relapse occurs shortly thereafter and the patient must be re-admitted. Heart failure and COPD patients suffer from decompensations and/or exacerbations and frequently require re-admission to a hospital due to relapse that might be avoided with a longer initial stay. Similarly, releasing a patient too soon may have consequences for other entities. For example, hospitals may not be reimbursed or may only be partially reimbursed for the costs associated for a re-admission as a result of such a relapse. Thus, it would be useful to provide techniques for predicting a likely relapse of a COPD or HF patient, as a tool for helping to avoid releasing a patient from the hospital too soon. Some forms of the present technology evaluate a patient's condition during a first time period to provide a prediction relating to the potential for relapse in a subsequent time period. For example, for heart failure and/or COPD patients, the potential for post-hospitalization decompensation and/or exacerbation events may be predicted from an analysis of respiratory parameters during hospitalization, such as an analysis of the respiratory movement signals as previously described.

Accordingly, a monitoring apparatus 7000 may be configured to monitor and analyse respiratory parameters during a time period from admittance to discharge that may be indicative of a likelihood of post-discharge relapse. By monitoring and analysing the respiratory parameters within the period from admittance to a point near or prior to discharge, the monitoring apparatus 7000 may determine whether the patient might be at risk for re-admission soon after release. In this regard, the methodology of the monitoring apparatus 7000 can provide a potential relapse alert to a clinician to advise whether release might be premature due to a risk of relapse. For example, the monitoring apparatus 7000 might warn the clinician that once released, the patient might be at a high risk for relapse and/or readmission and may further advise that careful monitoring for relapse should be considered for the particular patient or that the release should be reconsidered or postponed. In some cases, such a potential relapse alert may be presented as a numerical value, such as a Boolean indicator or a probability, which may comprise an estimate within a range so as to yield a scaled indication of greater or lesser risk of future relapse.

FIG. 7c is a flow chart illustrating a method of monitoring the cardio-pulmonary health of a patient as implemented within the monitoring apparatus 7000 in one form of the present technology. The method 7200, which may be used with a patient while the patient is hospitalized, is carried out by the processor 7006 of the monitoring apparatus 7000 and/or a processor in direct or indirect communication with such processor, configured by instructions stored on computer-readable storage medium such as the memory 7002.

The method 7200 at the first step 7210 extracts, monitors, and records respiratory parameters of a patient over the admission period, including one or more of the breathing rate, minute ventilation, tidal volume, sleep-disordered breathing severity indicators (e.g., apnea/hypopnea index), inspiratory waveform shape, expiratory waveform shape and the like, from data obtained with any one or more of the previously mentioned sensors. The method 7200 may perform an analysis of one or more of the extracted respiratory parameters to calculate an indicator of potential relapse or a probability of relapse at step 7220. Step 7220 may involve assessing how the parameters have changed during the course of the hospitalization period. One or more of the parameters or the changes therein may be compared to one or more thresholds in order to compute an indicator of potential relapse. Such thresholds may be empirically determined from historic data of one or more hospitalized patients who have relapsed and/or not relapsed after hospitalization. Optionally, such data may be based on thresholds taken from historic data of the particular patient. Alternatively, or additionally, a probability of relapse may be calculated at step 7220 based on a pattern of a plurality of the parameters or changes in a plurality of parameters. Such comparisons and/or pattern evaluations may be made, for example, by a decision-tree, a classifier or any other method of evaluation. Based on the computed probability of relapse or potential relapse indicator, a potential relapse alert may be generated at step 7230. For example, data indicative of the probability of relapse, such as the potential relapse indicator or the calculated probability of potential relapse, may be displayed on display device 7015 and/or sent as a message to a clinician via the connection 7008 at step 7230.

In some embodiments, the potential relapse indicator or probability of relapse may be continuously updated and displayed or transmitted based on a continuous monitoring and analysis of the extracted respiratory parameters during the monitoring period of hospitalization. However, in some embodiments, the indicator, probability and/or message concerning the potential for relapse may be generated in response to a request made by a user, such as a clinician, either through a user interface of the apparatus 7000 (e.g., one or more buttons or operation of a user interface of the apparatus) or by transmitting an electronic request to initiate the method 7200. In this regard, the monitoring apparatus 7000 may be configured to generate the potential relapse alert based on its previous analysis of the respiratory parameters. However, in some embodiments, the respiratory parameters used in the method 7200 may be extracted by and transmitted from the monitoring apparatus 7000 to the external computing device 7005, which may implement the steps 7220 and 7230 that calculate the probability of potential relapse or relapse indicator from the received respiratory parameters, and generate the potential relapse alert.

Event Prediction

FIG. 7d is a flow chart illustrating the principal steps in a method 7300 of predicting clinical events from signals representing movement (movement signals). The method 7300 may be used to implement step 7110 of the method 7100 in one form of the present technology in which the sensor data are one or more movement signals obtained from the motion sensor 7010, and the features related to cardio-pulmonary health are one or more SDB features. The method 7300 may also be used to implement steps 7210 and 7220 of the method 7200 in one form of the present technology in which the sensor data are one or more movement signals obtained from the motion sensor 7010, and the respiratory parameters are one or more SDB features. In one implementation, the method 7300 is carried out by the processor 7006 of the monitoring apparatus 7000, configured by instructions stored on computer-readable storage medium such as the memory 7002, and the movement signals are obtained from the contactless motion sensor 7010.

The method 7300 starts at step 7310, at which the movement signals are pre-processed to condition them for further processing. The pre-processing step 7310 (shown dashed in FIG. 7d) is optional and may be omitted. At the next step 7320, the pre-processed movement signals are analysed to extract SDB features indicative of the severity of SDB by the patient 1000 during the period represented by the movement signals. Finally at a prediction step 7330, the method 7300 uses the extracted SDB features to predict whether a clinical event is likely to occur within the predetermined prediction horizon.

As described above, in one form of the present technology the contactless motion sensor 7010 is a Doppler RF motion sensor. In such an implementation, the motion sensor 7010 provides two raw movement signals, labelled I and Q signals 7003a and 7003b, each generally indicative of bodily movement, but generally 90 degrees out of phase with each other.

In a first or "parallel" approach, the steps 7310 and 7320 are performed on each of the I and Q signals 7003a and 7003b in parallel, and the separately obtained features are combined during the feature extraction step 7320. In one implementation, under the "parallel" approach, the pre-processing step 7310 may be omitted. In a second or "combined" approach, the I and Q signals 7003a and 7003b are combined as part of the pre-processing step 7310, and the processing steps 7320 to 7330 are carried out on the combined movement signal. The combined approach has the advantage of less computational complexity than the parallel approach, at the potential cost of lower prediction accuracy.

In other forms of the present technology, the contactless motion sensor 7010 provides a single movement signal 7003. This is referred to below as the "single-channel" approach.

In one form of the present technology, step 7330 is omitted, i.e. no prediction of clinical events is made. The SDB features extracted at step 7320 may be used to trigger clinical alerts as described above. Alternatively, the extracted SDB features may be stored in the memory 7002 or transmitted to the external computing device 7005 for later diagnostic review.

The following sections describe implementations of each of the steps 7310 to 7330 of the event prediction method 7300 in more detail.

Pre-Processing 7310

Under the "combined" approach, the pre-processing step 7310 begins by combining the I and Q signals 7003a and 7003b in an adaptive geometrical manner into a combined movement signal c. In one implementation, the combination sub-step comprises three stages, applied to a window that slides along the I and Q signals 7003a and 7003b. In one implementation, the window is of 10 seconds duration with 50% overlap.

a. Check if the signals are 180 degrees out of phase using a cross-correlation, and flip them back to the same quadrant if so.
b. As the vectors (I, Q) form a cloud of points around a quasi-circular arc, subtract the mean of the cloud to centre the arc at (0, 0), locate the minimum $m_{IQ}$ of the centred cloud of points in both directions, and compute the length m of each vector (I, Q) referred to $m_{IQ}$.

$$m_{IQ}=(m_I, m_Q)=(\min[I-\langle I \rangle], \min[Q-\langle Q \rangle]) \quad \text{(Eq. 4)}$$

$$m=\sqrt{(I-m_I)^2+(Q-m_Q)^2} \quad \text{(Eq. 5)}$$

c. Subtract the mean of m to produce the (one dimensional) combined signal c.

$$c=m-\langle m \rangle \quad \text{(Eq. 6)}$$

The combined movement signal c is then (optionally) de-trended to remove baseline wandering. In one implementation, de-trending is implemented using a third-order polynomial:

$$c_1=DT_{poly,3}[c] \quad \text{(Eq. 7)}$$

In another implementation, de-trending is implemented using double-pass median filtering.

The de-trended signal $c_1$ is (optionally) bandpass filtered with a Butterworth bandpass filter with range set to the frequency range of respiratory functioning, this being in one implementation [0.1 Hz, 0.8 Hz] (corresponding to 6 to 48 breaths per minute).

A further (optional) sub-step in the pre-processing step 7310 is noise reduction. In one implementation, particularly suited to signals from Doppler RF motion sensors 7010, which are non-stationary, the noise reduction sub-step is carried out in the wavelet transform domain on the (bandpass filtered) de-trended combined movement signal $c_2$:

$$c_3=W^{-1}MWc_2 \quad \text{(Eq. 8)}$$

where W represents a wavelet transform, for example the 30-coefficient "symmlet" wavelet up to the fifth dyadic level, and M is a masking matrix that passes certain wavelet coefficients and rejects other considered as "perturbative".

The steps to implement the action of M are as follows:
a. Select the dyadic scales for which the "artefactness" (see below) of the wavelet coefficients is above a first threshold $T_A$;
b. From this set of scales, perform a hard thresholding (with threshold $T_C$) of the wavelet coefficients based on the standard deviation.

The "artefactness" at a scale quantifies the degree to which an artefact affects the signal at that scale. Artefactness is a measure of the skewness of the signal which can contain unlikely high amplitude values. The artefactness of a signal x may be computed as:

$$\text{Art}(x) = \frac{2\sigma_x}{\max(|x|) - \min(|x|)} \quad \text{(Eq. 9)}$$

where $\sigma_x$ is the standard deviation of the signal x. The further Art(x) is from 1, the larger the artefact is.

Under the "parallel" approach mentioned above, the combination sub-step is omitted from the pre-processing step 7310, and any or all of the subsequent sub-steps (de-trending, filtering, and noise reduction) are performed in parallel on each of the I and Q signals 7003a and 7003b.

Under the "single-channel" approach, any or all of the de-trending, filtering, and noise reduction sub-steps are performed on the movement signal 7003.

In the description below, the input(s) to the feature extraction step 7320 is/are referred to as (pre-processed) movement signal(s) to reflect the optional nature of the pre-processing step 7310.

Feature Extraction 7320

FIG. 7e is a block diagram 7400 illustrating the modules making up one implementation of the feature extraction step 7320 and their relationship under the combined or single-channel approach In the implementation illustrated in FIG. 7e, an activity estimation and movement detection module 7410 generates an activity count signal and a movement flag series from the (pre-processed) movement signal. A presence/absence detection module 7420 generates a presence/absence flag series from the (pre-processed) movement signal and the movement flag series. A sleep/wake analysis module 7430 calculates a hypnogram from the presence/absence flag series, the movement flag series, and the activity count signal. A breathing rate estimation module 7440 generates a series of estimates of the breathing rate of the patient from the (pre-processed) movement signal and the hypnogram. A signal selection module 7450 selects sections of the (pre-processed) movement signal, using the movement flag series and the hypnogram. A modulation cycle metrics calculation module 7455 generates an estimate of the modulation cycle length of the patient's respiration from the selected sections of the (pre-processed) movement signal. An envelope generation module 7460 generates envelopes of the selected sections of the (pre-processed) movement signal using the estimated breathing rate. An SDB event detection module 7465 generates candidate SDB events from the selected sections of the (pre-processed) movement signal using the estimated modulation cycle length. An SDB event confirmation module 7470 confirms the candidate SDB events generated by the SDB event detection module 7465. Finally, a feature calculation module 7580 calculates SDB feature values from the confirmed SDB events.

Under the parallel approach, the modules 7410 to 7470 of the block diagram 7400 are simply duplicated to process each of the I and Q signals 7003a and 7003b independently. A modified version of the feature calculation module 7480 combines the SDB events from the two parallel processing streams to calculating a single SDB feature set for the two (pre-processed) movement signals.

Under a "hybrid" approach, certain modules of the feature extraction step 7320 are duplicated so as to process the (pre-processed) movement signals independently, and the intermediate results are combined within various modules of the feature extraction step 7320 as described below.

FIG. 7f is a block diagram 7500 illustrating the modules making up one implementation of the feature extraction step 7320 and their relationship under the hybrid approach.

In the implementation illustrated in FIG. 7f, an activity estimation and movement detection module 7510 generates an activity count signal and a movement flag series from the I and Q signals 7003a and 7003b. A presence/absence detection module 7520 generates a presence/absence flag series from the I and Q signals 7003a and 7003b and the movement flag series. A sleep/wake analysis module 7530 calculates a hypnogram from the presence/absence flag series, the movement flag series, and the activity count signal. A breathing rate estimation module 7540 generates a series of estimates of the breathing rate of the patient from the I and Q signals 7003a and 7003b and the hypnogram. Signal selection modules 7550a and 7550b select sections of the I and Q signals 7003a and 7003b respectively, using the movement flag series and the hypnogram. A modulation cycle metrics calculation module 7555 generates an estimate of the modulation cycle length of the patient's respiration from the selected sections of the I and Q signals 7003a and 7003b. Envelope generation modules 7560a and 7560b generate envelopes of the selected sections of the I and Q signals 7003a and 7003b respectively using the estimated breathing rate. SDB event detection modules 7565a and 7565b generate candidate SDB events from the selected sections of the I and Q signals 7003a and 7003b respectively using the estimated modulation cycle length. SDB event confirmation modules 7570a and 7570b confirm the candidate SDB events generated by the SDB event detection modules 7565a and 7565b respectively. Finally, a feature calculation module 7580 calculates SDB feature values from the confirmed SDB events.

Each of the modules making up the feature extraction step 7320 is described in detail in the following sections.

Activity Estimation and Movement Detection 7410

The activity estimation and movement detection module returns a time series of "activity count" values indicating the level of bodily activity and a time series of binary movement flags indicating the presence or absence of gross bodily (non-respiratory) movement. Each time series is sampled at the sampling rate of the (pre-processed) movement signals (the movement signal frequency), equal to 10 Hz in one implementation. The movement flag series is used by the presence/absence detection, sleep/wake analysis, signal selection, and breathing rate estimation modules described below. In particular, the signal selection module selects for analysis those sections of signal that are not dominated by gross bodily movement. The activity count series, as well as the duration of movements and the time elapsed from the previous movement, is used by the sleep/wake analysis module to determine the sleep/wake state of the patient.

In one implementation, the activity estimation and movement detection module is based on movement signal power levels, movement signal morphology, and movement patterns.

In one implementation, five main sub-modules form part of the activity estimation and movement detection module.

An activity mapping sub-module generates a series of activity count values which are generally proportional to the power of the movement signal at corresponding times. The activity count is generated in the following manner:

The signal is bandpass filtered to the range [1.5 Hz, 4.5 Hz].

A maximum filter of duration 4 seconds is run over the signal to obtain an amplitude envelope.

The baseline of the signal (due to residual respiration activity) is extracted by estimating the 5th percentile of the signal on rolling 20-second windows.

The difference between the envelope and the baseline is compared to a threshold (0.0075 V in one implementation) and scaled again by the envelope.

The signal is partitioned into non-overlapping intervals. In one implementation, each interval is of duration two seconds.

The scaled signal is integrated over each interval and up-sampled to the movement signal frequency to produce the activity count series.

In one implementation, a movement detector sub-module proceeds as follows.

The signal is first highpass filtered to remove VLF components and baseline. Three features are then derived from the baseline-removed signal. The first feature is referred to as a noise feature.

A highpass filter with cutoff frequency around 1 Hz is applied to remove respiration components.

The highpass filtered signal is then partitioned into non-overlapping intervals. In one implementation, each interval is of duration two seconds.

The noise feature is calculated as the root mean square (RMS) of the filtered "noise" signal for each interval.

The second and third features are correlation and power features and are computed on a different frequency band to the noise feature.

The mean breathing rate of the overall monitoring session is first estimated by running an unbiased autocorrelation of the baseline-removed signal and finding the first minimum, which defines half the mean breathing rate. The mean breathing rate defines a patient-specific acceptable breathing rate frequency window as a range of frequencies around the mean breathing rate.

A lowpass filter, with cutoff around 2 Hz in one implementation, is applied to the baseline-removed signal. The lowpass filtered signal is then partitioned into overlapping windows, de-trended and de-meaned. In one implementation, the windows are 15 seconds long with 12 seconds of overlap (three seconds of shift).

The correlation feature is calculated by:

Taking the unbiased autocorrelation of the de-trended and de-meaned signal in each window.

Selecting the first peak, provided it is within the patient-specific acceptable breathing rate window defined by the mean breathing rate. (In the negative case, the correlation feature is set to 0.)

The power feature may be calculated by:
Calculating the power spectral density of the lowpass filtered signal for each window.
Identifying the maximum within the patient-specific acceptable breathing rate window as defined from the mean breathing rate.
Selecting a breathing band of +/−0.05 Hz over the maximum frequency and the first two harmonics.
Calculating the ratio between the signal power in the selected breathing band and that in the full band of the signal.

As the window length is greater than the three-second shift between windows, a maximum filter may be run over the correlation and power features so calculated.

All three features may be then interpolated to the movement signal frequency so that a feature value is present for each sample in the (pre-processed) movement signal.

The noise feature may be normalized by the mean power feature calculated for all samples with high correlation feature values (those with values greater than 0.9) and those with high power feature values (those with values greater than 0.8).

The baseline of the noise feature may be calculated by assigning to noise feature values over 0.003 the 95th percentile of all values below 0.003. Then a median filter of width 180 seconds is run and the baseline is defined as the 50th percentile of the filtered series. This baseline is then subtracted from the noise feature.

If the baseline-removed noise feature is above a "high" threshold (equal to 1 in one implementation) and the correlation and power features are below a "low" threshold (equal to 0.7 in one implementation), the corresponding movement flag is set to true. If the baseline removed noise feature is above its mean value, the movement flag is also set to true.

The movement flag series is finally expanded before and after each detected movement section by running the movement flag series through a maximum filter of multi-second duration, equal to 4 seconds in one implementation.

The movement correction sub-module produces a binary "validation" flag for the movements detected in the movement detector sub-module, by analysing trends of movement over several minutes. Movements associated with apneas, in fact, need not to be labelled as such as it would impair the performance of both the sleep/wake analysis and SDB event detection modules.

A repetitive movement mask is obtained by merging all movements within 120 seconds of each other, to identify sections where trains of apneas (generally obstructive) might be falsely labelled as movement sections and subsequently labelled as wake.
Only sections with duration of at least 5 minutes are processed by this sub-module, with ⅔ overlapping (implemented by partitioning into 300-second windows with 100-second shifts between them).
An amplitude envelope may be generated by:
  Performing peak-trough detection in the same manner as in the breathing rate estimation module described below.
  Defining an individual breath's start and end point as the mid-point between one peak and its successive trough.
  Assigning the envelope the peak-to-peak amplitude of the signal during each detected breath
The amplitude envelope may be filtered with a lowpass filter with cutoff 0.5 Hz.
The filtered envelope may be smoothed by performing soft-limiting when it exceeds its $70^{th}$ percentile value or twice its standard deviation and by hard-limiting it once it reaches its $70^{th}$ percentile multiplied by a scaling factor of 1.6.
The autocorrelation of the envelope may be calculated for the interval, and the first two peaks and troughs in the autocorrelation function corresponding to periods between 16 seconds and 90 seconds are identified.
The difference between the value of each peak and its preceding trough may be calculated and, if found to be greater than a set threshold, the whole interval is marked as non-movement, as a repetitive pattern compatible with a train of SDB events is deemed to be likely.

Under the hybrid approach, there follows a combination sub-module, in which:
Activity counts across both (pre-processed) movement signals are averaged.
Movement flags across both (pre-processed) movement signals are combined through an AND operation (that is, movement needs to have been detected on both signals to generate a true movement flag.)

Under the other approaches, the combination sub-module is not needed.

The final sub-module calculates movement state duration. This sub-module identifies all movement/no-movement transitions and generates a vector with the duration of all individual movement/no movement states.

The mean non-zero activity count, together with its standard deviation, skewness, kurtosis, and the $5^{th}$, $25^{th}$, $50^{th}$, $75^{th}$ and $95^{th}$ percentile of the distribution over all intervals with non-zero activity counts, may also calculated and stored. The total duration of intervals with non-zero activity counts may be calculated and stored as the Total Movement Time. The percentage of intervals with non-zero activity counts during the monitoring session may also be calculated and stored. This percentage may also be calculated on those periods that are marked as the first and second halves of the main sleep period (defined below).

Presence/Absence Detection 7420

The presence/absence detection module detects whether the patient is present within the field of the sensor 7010 (i.e. in bed), or is absent (i.e. not in bed). The presence/absence detection module generates a time series of presence/absence flags based on signal power levels, signal morphology, and the movement flag series generated by the activity estimation and movement detection module.

In one implementation, the presence/absence detection module may include sub modules. For example, five main sub-modules may be implemented as follows:
Pre-processing, performed separately on each (pre-processed) movement signal, in which, for example:
  The signal is highpass filtered with cutoff 0.1 Hz to remove baseline wander and low frequency components that might affect the morphological feature.
  The signal is split into non-overlapping epochs for analysis. Epoch length is chosen to be long compared to the duration of a breath. In one implementation, each epoch is 30 seconds in duration.
  The signal is de-meaned over each epoch.
Amplitude Analysis—Morphological Feature Gate, may also be performed separately on each (pre-processed) movement signal after the pre-processing sub-module. This sub-module may, for example, verify that:
  The RMS value of the signal in each epoch is greater than a minimum value associated with certain absence (equal to 0.0015 in one implementation).
  The signal in each epoch does not contain clear outliers. The assumption is that, in the case of low amplitude signal, there will be either quasi-Gaussian noise or small amplitude breathing. Outliers are deemed to be present if the ratio between either the $99.95^{th}$ and the $66.6^{th}$ or the $33.3^{rd}$ and the $0.05^{th}$ percentile exceeds a factor of 6. For a Gaussian distribution this ratio should not exceed 3:a safety factor of 2 is employed.

If both the above conditions are verified, the morphology feature calculated by the next sub-module as described below is kept intact.

If the first condition is not verified (the assumption is absence), the morphology feature is set to the maximum of its calculated value and a value that is large enough to guarantee absence being detected.

If the second condition is not verified, the morphology feature is assigned a NaN (not a number) value, and the epoch will be ignored in the detection of presence and absence (the assumption is burst of noise or twitch).

Calculation of Morphology feature, also may be performed separately on each (pre-processed) movement signal after the pre-processing sub-module and may be implemented as follows:

The morphology feature is calculated as the kurtosis of the autocorrelation of the signal during the epoch. An uncorrelated signal will return a peaky autocorrelation function, whereas a breathing signal will return an autocorrelation function with periodic peaks. Kurtosis is larger for a peaky distribution. A larger value of the morphology feature is associated with absence.

Artefact removal, trending, and combination. This sub-module may be performed on the, or each, morphology feature series calculated by the previous sub-module as follows:

Isolated high values of the morphology feature are assigned the value of the previous epoch.

For each signal, a mean filter, set to nine epochs in length in one implementation, is run over the morphology feature series.

Under the hybrid approach, a temporary combined feature vector is generated as follows. In case the RMS of both signals falls below a maximum threshold associated with expected presence (set to 0.01 in one implementation), the vector is assigned a value equal to the mean of the morphology feature of each input signal, otherwise a value of zero is assigned to skew the presence/absence flag towards presence.

The (combined) morphology feature series is converted to a presence/absence flag series by comparing each value with an absence/presence threshold, set to 20 in one implementation. If a morphology value is less than the threshold, the corresponding flag is set to True (presence); otherwise, the flag is set to False (absence).

Post-processing, performed on the presence/absence flag series, may be implemented making use of the movement flag series generated by the activity estimation and movement detection module as follows:

Transitions upon power up of the monitoring apparatus 7000 are ignored by assigning the flag value of the $5^{th}$ epoch to the initial four.

All the transitions from presence to absence and from absence to presence are examined. If during the section between the last movement (indicated by the movement flag series) prior to the presence/absence transition and the transition itself at least 85% of the morphology feature values are not NaN, the transition is moved back to the epoch following the previous movement. The equivalent is done for transitions between absence and presence. (The rationale for this type of re-labelling is that a presence/absence transition should be associated with a gross bodily movement into/out of bed.)

In an alternative implementation of the presence/absence detection module, suitable for the combined or single-channel approaches, for each epoch, the presence/absence flag is set to False (absence) if the RMS value of the (pre-processed) movement signal within the epoch falls below a "noise-only" threshold, set to 0.015 in one version of the alternative implementation in which the epochs are of 5-second duration. Otherwise, the presence/absence flag for the epoch is set to True (presence). The alternative implementation does not use the movement flag series.

Sleep/Wake Analysis 7430

The sleep/wake analysis module aims to classify each epoch as asleep, awake, absent, or unknown. (The epochs coincide with the epochs of the presence/absence detection module.) The resulting series of epoch classifications is referred to as a hypnogram.

In one implementation, the sleep/wake analysis module uses the activity estimation and movement detection module outputs to generate features which are fed into a classifier for each epoch. Some initial post-processing, integration with the presence/absence flags from the presence/absence detection module, and final post-processing allows the sleep/wake analysis module to refine the hypnogram.

In this implementation, the sleep/wake analysis module may be implemented with a number of sub-modules (e.g., four) as follows.

A feature extraction sub-module extracts some or all of the following features from the activity count signal and movement flag series:

Activity feature, which may be processed as follows:
  The activity count signal is normalised by dividing it by its mean, to reduce the range/sensitivity effect.
  The normalised activity count signal is integrated over each epoch.
  The fourth root of the integral is computed.

Duration of movement feature, which may be processed as follows:
  For each epoch, if one or more portions of movement are present, the square root of their mean duration in samples (including portions outside of the epoch of interest) is computed.

Duration of no movement feature, which may be processed as follows:
  For each epoch, if one or more portions of no movement are present, the square root of their mean duration in samples (including portions outside of the epoch of interest) is computed.

Kushida activity feature, which may be processed as follows:
  The Kushida activity is a weighted summation applied to the integrated activity counts, with weights set in one implementation to {0.04, 0.04, 0.2, 0.2, 2, 0.2, 0.04, 0.04}/2.96. (The Kushida activity feature for the initial four and final four epochs are only based on partial weighted sums.)

A classifier sub-module classifies the extracted features in each epoch to generate provisional sleep/wake labels [Sleep=0, Wake=1]. In one implementation, the classifier is a pre-trained linear discriminant analysis (LDA) classifier.

A post-processing sub-module may process the provisional sleep/wake label series in the following fashion:

The provisional sleep/wake labels are post-processed in accordance with Lotjonen pattern expansion, where short burst of Wake or Sleep within a larger Sleep or Wake section are relabelled as Sleep and Wake respectively. Lotjonen pattern expansion is illustrated in FIG. 7g.

Presence/absence flags from the presence/absence detector module are overlaid on the post-processed sleep/wake label series. A first temporary hypnogram is generated from the post-processed sleep/wake label series by assigning a NaN value to each epoch labelled as Sleep that coincides with an epoch flagged as Absent.

Meanwhile, the raw (un-post-processed) provisional sleep/wake labels are overwritten with Wake labels where NaN values are present in the first temporary hypnogram, and post-processed using the Lotjonen pattern expansion method to generate a second temporary hypnogram.

The second temporary hypnogram is combined with the first temporary hypnogram as follows: at each epoch where the first temporary hypnogram value is Sleep and the second temporary hypnogram value is Wake, the first temporary hypnogram value is set to Unknown.

The first temporary hypnogram becomes the final hypnogram after the following final post-processing steps:

Where an Unknown label is between two Wake labels, it is set to Wake.

Where at least 15 minutes of consecutive Unknown labels are present, those labels are set to Absent.

Sections of non-absence of duration less than or equal to 5 minutes are relabelled as Absent.

Finally, any Wake present at the beginning and/or end of the raw (un-post-processed) hypnogram is maintained in the final hypnogram.

In an alternative implementation, suitable for the combined or single-channel approaches, the sleep/wake analysis module uses the presence/absence flag series from the presence/absence detection module and the combined (pre-processed) movement signal to generate the hypnogram labelling each epoch as Sleep, Wake, or Absent. In the alternative implementation, the sleep/wake analysis module does not use the movement flag series generated by the activity estimation and movement detection module, but rather generates its own movement flag series (one flag for each epoch, indicating gross bodily movement within the epoch) by comparing the variance of the movement signal within the epoch with an adaptive threshold for the monitoring session. The adaptive threshold may, for example, be set in one version of the alternative implementation to the $95^{th}$ percentile of the variance over the monitoring session minus twice the $75^{th}$ percentile of the variance over the same monitoring session (when the $75^{th}$ percentile is bigger than 0.5), or to the $95^{th}$ percentile of the variance over the monitoring session minus 1.5 times the $75^{th}$ percentile of the variance over the monitoring session (when the $75^{th}$ percentile is less or equal to 0.5). If the variance exceeds the adaptive threshold, the movement flag for the epoch is set to True.

In the alternative implementation, the epochs labelled as Absent in the presence/absence flag series are first labelled as Absent in the hypnogram. A "waveform length" feature is extracted from the (pre-processed) movement signal $c_3$ within each epoch labelled as Present in the presence/absence flag series. Waveform length is calculated by measuring the cumulative changes in amplitude from sample to sample over the epoch. Metaphorically, it is the equivalent of treating the movement signal waveform like a jumbled string, and measuring the straightened-out length of the string. The waveform length feature effectively encapsulates the amplitude, frequency, and duration of the movement signal over the epoch. The waveform length feature value $w_i$ for epoch i is calculated as $$w_i = \sum_{n=2}^{N} |c_3(n) - c_3(n-1)| \quad \text{(Eq. 10)}$$

where N is the number of samples in the epoch.

The waveform length feature value $w_i$ for each Present epoch i is compared with an adaptive threshold T. If the value $w_i$ is less than the threshold T, the Present epoch is labelled as Sleep in the hypnogram; otherwise, the Present epoch is labelled as Wake. In order to compute the threshold value T for the monitoring session, the inter-quartile range features are calculated for the waveform length feature $w_i$ over the monitoring session (with each point in this feature vector representing the waveform length of an epoch, in similar fashion to the well-known R&K sleep scoring criteria). The threshold T is computed from the $50^{th}$, $75^{th}$, and $95^{th}$ percentiles $W_{50}$, $W_{75}$, and $W_{95}$ of the waveform length feature $w_i$ using the method illustrated in the flow chart of FIG. 7h. The parameters $\alpha_1$, $\alpha_2$, $\beta_1$, $\beta_2$, and $\beta_3$ are set to 4, 2.78, 10, 0.95, and 4 in one version of the alternative implementation.

A summary sub-module may calculate any of the following summary metrics from the final hypnogram:

total sleep time (TST) (the sum of the durations of all epochs labelled as Sleep).

the total time in bed (the sum of the durations of all epochs not labelled as Absent).

sleep efficiency (the ratio of total sleep time to total time in bed between the first and last epochs labelled as Asleep).

the sum of the durations of epochs labelled as Unknown (if any).

The hypnogram might indicate multiple separate contiguous sections where the patient is present (i.e. marked as Sleep or Wake). This is especially true for patients who are spending part of the daytime in bed because of their condition. The summary sub-module therefore generates "temporary sleep periods" by locating contiguous sections marked as Sleep or Wake, ignoring Absent-marked sections that are shorter than a threshold, set in one implementation to 30 minutes. For example, from five sections with the patient present during the monitoring session, two "temporary sleep periods" might be generated, because three of the four Absent-marked gaps between the presence sections are shorter than the threshold. The summary sub-module then defines a "main sleep period" as the longest of the "temporary sleep periods" so generated, and marks the start and end of the first and second halves of the main sleep period.

Breathing Rate Estimation 7440

The breathing rate estimation module makes an offline non-causal estimation of the breathing rate for each epoch of the monitoring session, using a breath detector based on peak-trough detection of the (pre-processed) movement signals. (The epochs coincide with the epochs of the presence/absence detection module and the sleep/wake analysis module.) The output of the breathing rate estimation module is referred to as a respirogram.

In one implementation, four main sub-modules may serve as a breathing rate estimation module:
- A pre-processing sub-module may implement any of the following steps:
  - Blanking out the sections of the movement signal that coincide with movement flags.
  - The signal may be filtered with a lowpass filter to remove any residual undetected movement. In one implementation, the lowpass filter is a Butterworth filter of order 10, with a cutoff frequency of 0.8 Hz.
- A peak-trough detection sub-module may implement any of the following steps:
  - The signal is passed through a highpass filter to remove the VLF components. In one implementation, the cutoff frequency is 0.15 Hz.
  - The average breathing rate across the monitoring session is estimated by performing autocorrelation over the whole filtered signal and selecting the first peak after 0.5 Hz. This average breathing rate is scaled up by a factor of 1/0.8 for further processing, to ensure all breaths will be captured.
  - A Rayleigh distribution is built with its peak at half of the average breathing duration. This distribution will be used as a likelihood factor for identifying turning points (hence only half of the breathing duration is used).
  - All turning points on the filtered signal are identified. For each turning point:
  - Select all turning points over the next 10 seconds as candidate turning points.
  - Define a figure of merit as the distance from the current turning point to the candidate turning point, multiplied by its own Rayleigh probability (the Rayleigh distribution value at the distance from the current turning point).
  - The turning point with the highest figure of merit is chosen and the process is repeated going forward.
  - Remove all turning points associated with previously detected movement sections.
- A breathing rate estimation sub-module proceeds as may implement any of the following:
  - From the turning points identified by the peak-trough detection sub-module, troughs are discarded, so that only peaks are considered.
  - Respiration intervals are defined as the distance between successive peaks. Respiration intervals greater than or equal to a duration that is long compared to a typical breath interval, set in one implementation to 7 seconds, are removed, as these are likely to be associated with interruptions in breathing or with movements.
  - The breathing rate for a window surrounding each epoch is computed as the median breathing rate (reciprocal of respiration interval) over all breaths in the window. In one implementation, the window is 3.5 minutes long.
- Under the hybrid approach, there follows a combination sub-module, in which breathing rates from both (pre-processed) movement signals are averaged at each epoch. Under the other approaches, the combination sub-module is not needed.

Given the length of the window used for breathing rate estimation, the breathing rate estimation module includes a fair amount of averaging and is therefore fairly robust against artefacts. However, for the same reasons, it is not very sensitive to local breathing rate variations.

For all epochs labelled in the hypnogram as Absent or Unknown, the breathing rate is assigned a NaN value.

In an alternative implementation, the breathing rate estimate is simply the value Freq computed using (Eq. 19) by the activity estimation and movement detection sub-module.

The mean breathing rate over the monitoring session, together with its standard deviation and the 5th, 25th, 50th, 75th and 95th percentile of the distribution, are may also be calculated and stored by the breathing rate estimation module.

Signal Selection 7450

The signal selection module aims at selecting suitable sections of the (pre-processed) movement signals for subsequent SDB event detection. One idea underlying signal selection is that SDB event detection may be performed only on sections of the movement signals where the patient is asleep. The hypnogram output of the Sleep/Wake analysis module can therefore serve to gate the SDB event detection through the signal selection module. In addition, as any signal generated by gross bodily movement will overshadow the respiratory movement signal potentially associated with a SDB event, movement sections are also removed by the signal selection module, leaving only sleep-and-breathing sections for SDB event detection. Finally, given that the methods employed in the SDB event detection module are time-domain amplitude-dependent methods, it is helpful to ensure that a sufficient signal to noise ratio is present, in order to guarantee a sufficient margin to detect the drop in respiratory effort that characterises an SDB event.

The signal selection module works as an interface between the Sleep/Wake analysis module and the SDB event detection module. Its main function is to feed the subsequent signal processing modules only with sections of sleep and breathing and sufficient signal quality.

The signal selection module proceeds as follows.

The hypnogram (upsampled to the sampling rate of the movement flag series) and the movement flag series are initially combined to obtain a mask of sleep and breathing. The mask has the value 1 at samples where the hypnogram indicates sleep and the movement flag is false.

The mask of sleep and breathing is then applied to each (pre-processed) movement signal, resulting in one or more sections of variable duration. For each of these sections, a figure of merit is calculated, and a decision on whether that section should be selected is taken based on the comparison of a figure of merit with a threshold.

For SDB event detection, it is estimated that it should be possible to observe at least a 50% drop in a validated measure of respiratory effort. The respiratory effort measure should therefore be rarely pulled below the 50% threshold by noise. Assuming a quasi-Gaussian additive noise distribution, 97.5% of the noise samples will have peak to peak amplitude within four times the RMS noise value of a given section. For a sinusoid the ratio of peak-to-peak amplitude to RMS value is $2\sqrt{2}$. Therefore, to be of sufficient quality for reliable SDB event detection, a sleep-and-breathing signal section should have an RMS value that is at least given by $$\text{rms} \geq 2 \times \frac{4}{2\sqrt{2}} \times \text{rms}_{max\ noise} \qquad (\text{Eq. 11})$$

where $\text{rms}_{maxnoise}$ is a maximum RMS value for noise.

The signal selection module may therefore apply a running standard deviation (RMS) filter, of duration equal to 150 seconds in one implementation, to each section of sleep-and-breathing (pre-processed) movement signal. The section is deemed to be of good quality, and is therefore selected by the signal selection module, when a high percentile, set in one implementation to the $75^{th}$ percentile, of the distribution of the RMS values for the section exceeds a noise threshold. The noise threshold is calculated as the smaller of a maximum RMS noise value for the motion sensor 7010 (equal to 0.005 for the SleepMinder sensor unit) and the $5^{th}$ percentile of the distribution of the RMS values of the pre-processed movement signal calculated for the section.

Under the hybrid or parallel approach, each (pre-processed) movement signal is processed independently so certain sections might be selected for one channel only. The total analysis time (TAT) is calculated as the total duration of signal that has been selected for SDB event detection in at least one channel. The TAT is used as the denominator of the AHI calculated by the feature calculation module described below.

The total duration of sleep-and-breathing signal sections for each channel is computed and stored. The total duration of good-quality sleep-and-breathing signal for each channel is computed and stored. The total duration of poor-quality sleep-and-breathing signal for each channel is also computed and stored.

To ensure that the AHI returned by the feature calculation module is reliable and representative, at least one of the following conditions may be imposed before continuing with the SDB event detection in each channel:

The total duration of "patient-presence" is greater than a minimum duration. In one implementation, this minimum duration is three hours, in line with standard practice in a PSG lab.

The total duration of good-quality sleep-and-breathing signal is greater than a minimum duration. In one implementation, this minimum duration is two hours, in line with standard practice in a PSG lab.

The ratio of good-quality to poor-quality sleep-and-breathing signal duration is at least 1:R. In one implementation, R was set to 2, to ensure that at least 33% of the sleep-and-breathing signal can be used for SDB event detection.

Otherwise, the prediction method 7300 is aborted for that channel

Envelope Generation 7460

The envelope generation module aims at generating a measure of the respiratory effort, in the form of an envelope that retains not only the frequency but also the amplitude content of breathing modulation.

In one implementation, the envelope generation module relies on a few signal processing steps. For each section of good quality sleep-and-breathing signal selected by the signal selection module any of the following may be implemented:

the section may be processed for outlier removal by assigning $$x(x>\text{prctile}(x,95))\text{prctile}(x,95) \qquad (\text{Eq. 12})$$

and $$x(x<\text{prctile}(x,5))\text{prctile}(x,5) \qquad (\text{Eq. 13})$$

Given that the spectrum of an amplitude-modulated a respiratory movement signal (see Eq. 16) would have two small peaks at either side of the breathing rate fundamental, the section may be filtered with a bandpass filter to remove very low and high frequency components. In one version of this implementation, the bandpass filter is a second-order Butterworth filter with range [0.1 Hz, 0.8 Hz].

In order to maintain the amplitude information, the section may be filtered with a double max & hold filter, one for positive samples and the other for negative samples, to give a positive envelope and a negative envelope.

The duration of the double max & hold filter can be important: too long a filter will generate a smoother envelope but will reduce the duration of dips, for averaging reasons. At the same time, too short a filter will give rise to ringing due to the nature of the respiration signal.

The ideal max & hold filter duration is slightly larger than a single breath duration. For this reason, the breathing rates estimated by the breathing rate estimation module are scaled down by a factor that is slightly greater than one, to give a margin to avoid a ringing effect whilst maintaining a reasonably short (<<2 breaths) filter duration. In one implementation, the factor is 1.25.

For each section, the mean value of the scaled down respirogram over the section is used as the max & hold filter duration.

The final envelope may be generated as the difference between the positive and negative envelopes.

In an alternative implementation, the envelope of each selected section $c_3$ of the (pre-processed) movement signal may be generated by:

Taking the Hilbert transform $H\{c_3\}$ of $c_3$;

Using the Empirical Mode Decomposition (EMD) to generate the envelope $Ec_3$ from the Hilbert transform $H\{c_3\}$ as follows:

$$Ec_3=\text{EMD}\{|H\{c_3\}|\} \qquad (\text{Eq. 14})$$

In a variation of the alternative implementation, the envelope may be generated by lowpass filtering the modulus of $c_3+jH\{c_3\}$, where j is the square root of $-1$. In one version of the variation of the alternative implementation, the lowpass filter has a cutoff frequency of 0.15 Hz.

Modulation Cycle Metrics Calculation 7455

The modulation cycle metrics calculation module estimates the mean modulation cycle length of the patient's modulated breathing cycles to better tailor the SDB event detection module to that patient. The main challenges are the selection of correct samples to base the estimation upon and the extraction of the modulation frequency in the VLF band of the spectrum using the selected samples.

In one implementation, the modulation cycle metrics calculation module begins by pre-processing each selected section of the (pre-processed) movement signal in an identical manner to that of the envelope generation module described above (outlier removal and bandpass filtering).

Next, each pre-processed section may be normalised to zero mean and unity standard deviation, and an envelope may be generated for each normalised section using any of the methods described above in the envelope generation module.

For each selected section, overlapping macro-epochs may be generated. The choice of the duration of the macro-epochs is influenced by the fact that modulated breathing cycles might last up to two minutes each for some patients and that three wavelengths are desirable for estimating the modulation cycle length. In one implementation, the macro-epochs have a duration of six minutes with an overlapping of four minutes Each macro-epoch may be processed with any of the following steps:

The envelope may be de-meaned.

The envelope may be multiplied by a Chebichev window to avoid edge effects on the VLF section of the spectrum.

The fast Fourier Transform (FFT) and from it the power spectral density (PSD) may be calculated for the envelope.

The PSD may be interpolated to increase its resolution.

Peaks of the PSD may be located. Each peak corresponds to a potential modulated breathing cycle. The peak height represents the modulation power, and the peak frequency is the reciprocal of the modulation cycle length.

Invalid peaks may be discarded. Valid modulated breathing cycles may be defined as having:

A cycle length compatible with physiological range (between 30 seconds and 100 seconds, i.e. from 0.01 Hz to 0.033 Hz).

A peak power greater than a minimum power, set in one implementation to $10^4$.

A clear peak, which is defined as a peak with an occupied bandwidth (OBW) at 50% of the maximum height of less than 0.01 Hz, and a height greater than 200% of the adjacent minima An extra condition may be imposed on the DC power of the PSD, namely that it does not exceed 150% of the value of the maximum peak height, in order to avoid DC related effects being marked as due to breathing modulation.

Based on the conditions detailed in the last point, for each macro-epoch, none, one, or more valid peaks might remain.

All macro-epochs for the monitoring session may then be processed with any of the following:

Macro-epochs with no valid peaks are discarded.

Macro-epochs with only one remaining valid peak are processed first (as their estimate should be more accurate—i.e. not affected by misdetection of harmonics). The mean of the modulation cycle length (the reciprocal of the peak frequency), weighted by the logarithm of the modulation power (the peak height), is computed over all such macro-epochs.

For all other macro-epochs, which contain more than one valid peak, the closest peak to the mean modulation cycle length computed for all macro-epochs with a single peak is chosen.

Any valid peak with modulation cycle length falling outside the $5^{th}$ or $95^{th}$ percentile of the overall modulation cycle length distribution is discarded.

The mean of all remaining modulation cycle lengths (weighted by their modulation power) over the monitoring session may then be computed, together with its standard deviation and $5^{th}$, $25^{th}$, $50^{th}$, $75^{th}$ and $95^{th}$ percentiles.

One mechanism by which congestive heart failure and CSR are connected is the buildup of fluid in the pulmonary cavity, which affects the "loop gain" of the body's respiratory control system. The extent of CSR depends not only upon the raw amount of fluid in the pulmonary cavity, but also upon its distribution. This distribution changes over the monitoring session, since the person's body position has changed at the start of the session from generally vertical to generally horizontal. Therefore, the values of the extracted features may be expected to vary over of the monitoring session. The later values of those features during a monitoring session may provide a truer indication of the severity of congestive heart failure and therefore the likelihood of ADHF events that the earlier values, since by that time the fluid should have assumed a new equilibrium distribution.

The mean of all remaining modulation cycle lengths (weighted by their modulation power), together with its standard deviation and $5^{th}$, $25^{th}$, $50^{th}$, $75^{th}$ and $95^{th}$ percentiles, may also therefore be computed for those periods marked as first and second halves of the main sleep period by the sleep/wake analysis module.

In similar fashion, values of modulation power and OBW for each macro-epoch with at least one valid peak may be calculated and stored, together with their means, standard deviations, and their $5^{th}$, $25^{th}$, $50^{th}$, $75^{th}$ and $95^{th}$ percentiles for the overall monitoring session and each half of the main sleep period.

Under the hybrid approach, the statistics from both channels may be combined by averaging the statistics from both channels, weighted by the number of valid macro-epochs for each channel. Under the other approaches, such combination is not needed.

SDB Event Detection 7465

The SDB event detection module aims to detect portions of the movement signal where SDB events, including both OSA and CSR episodes, are likely to have occurred. Such portions are referred to as candidate SDB events.

In one implementation, the SDB event detection module uses the modulation cycle length estimated by the modulation cycle length estimation module to make a set of one or more generic SDB respiratory effort templates specific to the patient 1000. The generic templates may be designed to detect a reduction in respiratory effort associated with an SDB event. By cross-correlating the patient-specific templates against the envelope (measure of respiratory effort) generated by the envelope generation module, and comparing with a threshold, candidate SDB events may be detected.

In one version of this implementation, three generic SDB respiratory effort reduction templates are defined using sine and cosine functions and a Gaussian distribution. FIG. 7i contains illustrations of three example generic SDB respiratory effort reduction templates in one version of this implementation. Appendix A contains specifications for each of the three generic templates, parameterised by the modulation cycle length CL.

The generic templates are instantiated by filling in the modulation cycle length value estimated by the modulation cycle length estimation module as the parameter CL.

A correlation feature is generated by cross-correlating the envelope with each of the patient-specific templates and accepting the maximum value of the correlation values for each sample. In one implementation, this operation is performed at a small fraction, e.g. one tenth, of the sampling rate of the movement signals, to reduce the computational burden. Whenever the correlation feature exceeds a threshold, set to 0.5 in one implementation, for a time that is greater than another threshold (set in one implementation to ⅙ of the modulation cycle length or 10 seconds, whichever is smaller), a candidate SDB event is detected. Candidate SDB events too close to each other, i.e. such that their mid-points are within half of the mean modulation cycle length, are discarded. The result is a vector of locations of candidate SDB events within the monitoring session.

An alternative implementation of the SDB event detection module is suitable for the combined or single-channel approach. The alternative implementation detects candidate SDB events by comparing the drop in the respiratory effort envelope with a baseline according to the AASM scoring rules:

Hypopnea: A reduction in the airflow of ≥50% of baseline with 3% desaturation OR a reduction in airflow of ≥30% with a 4% desaturation, lasting for at least 10 seconds.

Apnea: A reduction in airflow of ≥90% of baseline lasting for at least 10 seconds.

In some versions of the apparatus 7000 there might be no access to the oxygen desaturation levels. Instead, three sliding windows may be utilized. The main window is the one in which the mean envelope value is computed as a proxy for the airflow. In one example, the main window is a sliding window of 10 seconds with 75% overlap. The other two windows, which surround the main window as it slides, are utilized to determine the baseline. In one example, these two baseline windows comprise the previous 35 seconds and the next 35 seconds before and after the main window. If the mean envelope value in the main window satisfies either of the above criteria (without the oxygen desaturation) with respect to the baseline defined by the mean envelope value in the two baseline windows, a candidate SDB event is detected.

The alternative implementation of the SDB event detection module then discards candidate SDB events of duration less than 10 seconds, in accordance with the AASM scoring rules described above.

A further alternative implementation of the SDB event detection module is also suitable for the combined or single-channel approach.

One version of the further alternative implementation operates on the un-pre-processed and pre-processed movement signals c and $c_3$ and the envelope $Ec_3$, and therefore does not use the modules 7410 to 7450.

The instantaneous power of the (un-pre-processed) movement signal c is first computed as the variance Var of c over a sliding window of length N samples:

$$\text{Var}(n) = \frac{1}{N} \sum_{n-\frac{N}{2}}^{n+\frac{N}{2}-1} c^2(j) \quad \text{(Eq. 15)}$$

In one version of the further alternative implementation, Var is computed on a 30-second sliding window with 75% overlap.

Next, the modulation depth MD of the (pre-processed) movement signal $c_3$ may be estimated. A noiseless regularly amplitude-modulated signal has the form:

$$AM_{Mod}(t) = K(1 + MD \cos(\omega_{AM}t + \phi_{AM}))\cos(\omega_{FM}t + \phi_{FM}) \quad \text{(Eq. 16)}$$

where MD is the modulation depth, varying between 0 and 1. The modulation depth of a respiratory movement signal is an indication of the severity of CSR. The modulation depth MD may be estimated as follows:

$$MD = Sat_{Lin}\left(\frac{\sigma_{Ec_3}}{\sigma_{c_3}}, a\right) \quad \text{(Eq. 17)}$$

where $\sigma_{c_3}$ and $\sigma_{Ec_3}$ are the standard deviations of the signal and its envelope, and $Sat_{Lin}$ is a saturation mapping to limit MD to the range [0, 1], given by $$Sat_{Lin}(x,a) = \Theta(x)x(1-\Theta(x-a)) + \Theta(x-a) \quad \text{(Eq. 18)}$$

where a is set to 1, and $\Theta(\;)$ is the Heaviside step function.

Spectral analysis provides a straightforward and robust way to extract the main harmonic of the signal $c_3$, which is the respiratory movement when such a movement is present. In one version of the further alternative implementation, an Auto-Regressive Yule Walker method (of order 9) may be used to estimate the Power Spectral Density (PSD) of $c_3$ and its envelope $Ec_3$, thus producing two PSDs: $P_{c_3}(\omega)$ and $P_{Ec_3}(\omega)$ The location of the highest peak of the magnitude of the PSD $P_{c_3}(\omega)$ is used as an estimate Freq of the breathing rate:

$$\text{Freq} = \arg\max_\omega |P_{c_3}(\omega)| \quad \text{(Eq. 19)}$$

The bandwidth of a signal may be a measure of its "irregularity". The bandwidth BW of the signal $c_3$ may be computed as $$BW = \frac{\sqrt{\int_\Omega P_{c_3}^\%(\omega)(\omega - \omega_{c_3})^2 d\omega}}{\int_\Omega d\omega} \quad \text{(Eq. 20)}$$

where $\omega_{c_3}$ is the location of the highest peak of the magnitude of the PSD $P_{c_3}(\omega)$, $\Omega$ is the frequency range of interest, and $P_{c_3}^\%(\omega)$ is the normalised PSD of $c_3$ computed as:

$$P_{c_3}^\%(\omega) = \frac{P_{c_3}(\omega)}{\int_\Omega P_{c_3}(\omega)d\omega} \quad \text{(Eq. 21)}$$

The spectral entropy takes full advantage of the previously estimated PSDs. The Normalized Spectral Entropy $H_x$ of a signal x is computed from the normalised PSD of x as follows:

$$H_x = \frac{-\int_\Omega P_x^\%(\omega)\log(P_x^\%(\omega))d\omega}{\int_\Omega d\omega} \quad \text{(Eq. 22)}$$

The spectral entropy $Hc_3$ of the signal $c_3$ and the spectral entropy $HEc_3$ of the envelope $Ec_3$ are both computed using (Eq. 22).

Three categories of breathing may be identified:

Regular breathing (RB), characterized by an almost constant amplitude signal in the breathing frequency band. The frequency can be time varying.

Irregular breathing (IB), characterized by an irregular amplitude signal in the breathing frequency band. This irregularity can be due to chest or abdomen movement irregularity, airways closures, swallowing/coughing and like behaviours.

Cheyne-Stokes respiration (CSR), characterized by a regularly amplitude modulated signal in the breathing frequency band.

The entropies $Hc_3$ and $HEc_3$ have characteristic behaviours depending on the breathing category. In one version of the further alternative implementation, a clustering algorithm based on Gaussian Mixture Models is applied to the entropies and $Hc_3$ and $HEc_3$ to find an approximation of the set of three probability densities that best correspond to the three categories. In another version of the further alternative implementation, a Landmark-based Spectral Clustering is applied first followed by a Gaussian fit of the probability densities of the clusters.

The centres (means) of the three Gaussians identified by the clustering, by either version, are expressed as 3-vectors $G_{c3}$ and $G_{Ec3}$.

The median $Hhc_3$ of $G_{c3}$ is found and clipped above, as follows:

$$Hhc_3 = \min\{Med[G_{c3}], 0.8\} \quad \text{(Eq. 23)}$$

The entropy $Hc_3$ referred to this median $Hhc_3$ is then inverted and saturated, such that a high value of "inverted entropy" $H^i$ corresponds to a more regular signal:

$$H^i = Sat_{NL}[\exp(-\lambda(H_{c3}-Hhc_3)), T_{c3}, S_{c3}] \quad \text{(Eq. 24)}$$

where the sigmoidal saturation function $Sat_{NL}$ is defined as $$Sat_{NL}[x, T, S] = \frac{T}{\exp(-4Sx)+1} \quad \text{(Eq. 25)}$$

and $\lambda$, $T_{c3}$, and $S_{c3}$ are parameters. In one version of the further alternative implementation, $\lambda=5$, $T_{c3}=1$, and $S_{c3}=20$.

The Cheyne-Stokes index CS of the movement signal is then computed as follows:

$$CS = Sat_{NL}[CS_{c2} - CS_{CS}, T_{CS}, S_{CS}] \quad \text{(Eq. 26)}$$

where $$CS_{c3} = MD(1-H_{Ec3})(1-H_{c3}) \quad \text{(Eq. 27)}$$

and $T_{CS}$, $CS_{CS}$, and $S_{CS}$ are parameters. In one version of the further alternative implementation, $T_{CS}=1$, $CS_{CS}=0.3$, $S_{CS}=20$.

The following four classes of movement signals are defined:
1. Cheyne-Stokes respiration (CSR) (class CS);
2. Movement that is not CSR (class M);
3. No movement (class NM);
4. Apneas and Hypopneas (class AH)

Four Boolean-valued indicator or "truth" variables $CS_T$, $M_T$, $NM_T$, and $AH_T$, may be computed as time series, indicating that the movement signal belongs to (true) or does not belong to (false) the respective classes at a given time instant. The first three truth variables $CS_T$, $M_T$, $NM_T$, which are mutually exclusive in the sense that only one of the three can be true at any time, are computed by applying a set of logical rules. In one version of the further alternative implementation, the logical rules are:

The signal belongs to the movement class if the instantaneous power is greater than a movement threshold, the entropy is less than an entropy threshold, and the Cheyne-Stokes index is below a Cheyne-Stokes threshold:

$$M_T = (Var \geq T_m) \& (H^i \leq T_{Hi}) \& (CS \leq T_{CS}) \quad \text{(Eq. 28)}$$

The signal belongs to the no-movement class if the instantaneous power is less than a no-movement threshold and the signal and does not belong to the movement class:

$$NM_T = (Var \leq T_{NM}) \& :M_T \quad \text{(Eq. 29)}$$

The signal belongs to the CS class if the Cheyne-Stokes index is greater than the Cheyne-Stokes threshold and the signal and does not belong to the movement class or the no-movement class:

$$CS_T = (CS > T_{CS}) \& :M_T \& :NM_T \quad \text{(Eq. 30)}$$

The movement threshold, entropy threshold, Cheyne-Stokes threshold, and the no-movement threshold values $T_M$, $T_{HS}$, $T_{CS}$, and $T_{NM}$ are set in one version of the further alternative implementation as follows: $T_M=2$, $T_{Hi}=0.95$, $T_{CS}=0.1$ and $T_{NM}=0.0001\ T_M$.

The fourth truth variable $AH_T$ is computed using adaptive thresholding on a sliding window of length $W_{AH}$. In one version of the further alternative implementation, $W_{AH}$ is set to 30 seconds. The value of $W_{AH}$ may be increased to account for longer duration apneas or hypopneas.

An adaptive threshold $T_{AHt}$ is computed as half the mean of the instantaneous power Var over the window, and the truth variable $AH_T$ is true if the instantaneous power is less than the adaptive threshold $T_{AHt}$, and either the Cheyne-Stokes index is less than an apnea/hypopnea Cheyne-Stokes threshold or the entropy is greater than an apnea/hypopnea entropy threshold:

$$AH_T = (Var < T_{AHt}) \& ((CS < T_{CSAH}) | (H_i > T_{HiAH})) \quad \text{(Eq. 31)}$$

The apnea/hypopnea Cheyne-Stokes threshold and the apnea/hypopnea entropy threshold $T_{CSAH}$ and $T_{HiAH}$ take the following values in one version of the further alternative implementation: $T_{CSAH}=0.1\ T_{CS}$ and $T_{HiAH}=0.095$.

The candidate SDB events are the intervals in which either $AH_T$ or $CS_T$ are true.

SDB Event Confirmation 7470

The event confirmation module confirms or discards each candidate SDB event based on analysis of the (pre-processed) movement signal $c_3$ corresponding with the candidate CSR event, or its envelope representing respiratory effort.

One implementation of the event confirmation module compares the duration and the amount of reduction in respiratory effort associated with each candidate SDB event against patient specific threshold time-domain and amplitude-domain criteria defining SDB events. This implementation of the event confirmation module also extracts features of the hyperpnea sections adjacent to the candidate SDB events to exclude misdetections due to "twitches" or other non-SDB physiological events.

In this implementation, the event confirmation module comprises two main stages. First, the extreme points of each candidate SDB event are located by:

Locating the minimum respiratory effort during the candidate SDB event.

Identifying all local peaks surrounding the location of minimum effort within 85% of the modulation cycle length (about a 70% margin over mean modulation cycle length value).

Calculating a probability p as a predefined function of the distance k between the location of minimum respiratory effort and each location of maximum respiratory effort on either side of it. In one implementation, the function p[k] is defined as $$p[k] = \frac{Env[k]}{Env[0]} \min\left(\min\left(\frac{|k|}{CL/6}, 1\right), \min\left(\frac{\frac{2}{3}CL}{|k|}, 1\right)\right) \quad \text{(Eq. 32)}$$

where CL is the estimated modulation cycle length.

Choosing the most likely maximum based on the difference in respiratory effort multiplied by the probability p.

Verifying that the minimum distance between maxima is greater than a minimum duration, set in one implementation to 10 seconds.

Each candidate SDB event may then be confirmed by:

Calculating the minimum ratio between either maximum of respiratory effort and the minimum respiratory effort.

Normalizing the envelope for the candidate SDB event according to this ratio.

Verifying that adjacent hyperpnea sections, where the respiratory effort envelope has a magnitude greater than twice that of the minimum value, have a duration greater than a minimum value (set to 9 seconds in one version of this implementation).

Verifying that the respiratory effort envelope dips below the hypopnea threshold (defined as 60% of original respiratory effort) for a time greater than one fifth of the modulation cycle length. A detected SDB event can be shorter than 10 seconds, as the max & hold filtering applied to detect the envelope has duration larger than 2 seconds.

An alternative implementation of the SDB event confirmation module computes certain features from the (pre-processed) movement signal $c_3$ corresponding to each candidate SDB event, or its envelope, and applies a rule-based inference engine to the computed features to determine whether to confirm or discard each candidate SDB event. The (pre-processed) movement signal $c_3$ corresponding with each candidate SDB event is first partitioned into two periods: the apnea/hypopnea period, and the ventilatory or hyperpnea period.

The computed features may be some or all of the following:

The kurtosis K of the autocorrelation R(i) of the movement signal $c_3$. The kurtosis is a measure of the "peakiness" of a probability distribution. A higher kurtosis indicates the candidate SDB event is less likely to be a true SDB event, whose autocorrelations tend to decay more gradually away from their peaks. The kurtosis K is computed as $$K = \frac{\sum_{i=1}^{P}(R(i)-\overline{R})^4}{(P-1)\sigma_R^4} - 3 \quad \text{(Eq. 33)}$$

where P is the number of samples of the autocorrelation, $\overline{R}$ is its mean value, and $\sigma_R$ its standard deviation.

The waveform length $H_{wl}$ of the hyperpnea period of the candidate SDB event, a feature that, as described above in relation to (Eq. 10), encapsulates the amplitude, frequency, and duration of the hyperpnea sections. A higher waveform length indicates the candidate SDB event is less likely to be a true SDB event. The waveform length is computed as in (Eq. 10).

Degree of Freedom (DOF): An indication of the complexity of the breathing pattern represented by $c_3$. The DOF value is computed from $c_3$ as $$DOF = \frac{\left[\sum_{n=1}^{N} c_3(n)\right]^2}{\sum_{n=1}^{N}[c_3(n)]^2} \quad \text{(Eq. 34)}$$

A movement signal with only one sharp peak would have a DOF value of nearly 1, while a sinusoidal signal would have 0 degrees of freedom. Some of the candidate SDB events might be actually related to noise-like portions in the movement signal. However, such noise-like portions are not related to normal breathing patterns, and may be discriminated by the DOF feature value, as genuine SDB events tend to exhibit lower values of DOF.

Mean Envelope (ME), a feature that indicates the respiratory effort during the candidate SDB event. If the patient is breathing normally, a sudden movement or a transient arousal could trigger a false positive SDB event detection. In order to account for such cases, the value of the $50^{th}$, $75^{th}$, and $95^{th}$ percentiles of the mean envelope value of the candidate SDB events for several patients are computed to infer what the normal values should be on average and identify the extreme values. Candidate SDB events that have higher mean envelope value than the $95^{th}$ percentile of the mean envelope values of all the candidate SDB events during a monitoring session are unlikely to be true SDB events. If the $95^{th}$ percentile of the mean envelope value is too large in comparison with other patients' mean envelope values, with a big value for the 95% percentile of the waveform length feature, the candidate SDB event is less likely to be a true SDB event.

Irregularity factor IR, a feature that quantifies the breath-to-breath variability in the hyperpnea section of the candidate SDB event that requires low computational resources. The irregularity factor is indicative of the nature of the underlying process, i.e., narrow-band or broadband. A narrow-band process is a stationary random process whose spectral density has significant values only in a band of frequencies whose width is small compared to the magnitude of the centre frequency of the band. A wide-band process has significant power terms over a wide range of frequencies. An SDB event is expected to be a narrow-band process with a low irregularity factor. In one version of the alternative implementation, the irregularity factor IR is computed for the hyperpnea sections as the ratio of the number ZC of upward zero crossings, computed as described below, to the number NP of peaks:

$$IR = \frac{ZC}{NP} \quad \text{(Eq. 35)}$$

where NP is computed as the square root of the ratio of the fourth moment of the hyperpnea sections to the second moment. The moments may be computed in the frequency domain, or in the time domain.

The rule-based inference engine applies a set of rules to the computed feature values to confirm each candidate SDB event. The candidate SDB event is confirmed or discarded depending on whether the feature values satisfy the specified rules. In one version of the alternative implementation, the inference engine applies the rules set out in Appendix B. The alternative implementation of the SDB event confirmation module also analyses the candidate SDB events to see if they correspond to CSR events or not. As with SDB event confirmation under the alternative implementation, certain features are computed from the (pre-processed) movement signal $c_3$ corresponding with each candidate SDB event, and a rule-based inference engine is applied to the computed features to determine whether to mark each candidate SDB event as a CSR event or not.

The computed features are as follows:

Modulation cycle length (CL), defined as the time from the beginning of the apnea/hypopnea period of the SDB event to the end of the following hyperpnea period, i.e., apnea/hypopnea period length plus ventilation period length (VentlLength). A typical range for CL in CSR events is from 30 seconds to 90 seconds. The waveform length of each modulation cycle, denoted as CWL, is also computed using (Eq. 10) over the modulation cycle Number of zero crossings (ZC): This feature represents the number of times the movement signal $c_3$ crosses the x-axis. This is an indicator of how fast the movement signal $c_3$ oscillates within the modulation cycle, which in turn is an indicator of the breathing rate during the SDB event. SDB events with ZC values indicating a breathing rate outside the physiological breathing range are less likely to be CSR events. For a movement signal section with N samples, the number of zero crossings feature value ZC is computed as:

$$ZC = \frac{1}{2}\sum_{n=1}^{N-1} |\text{sgn}(c_3(n)-t) - \text{sgn}(c_3(n-1)-t)| \quad \text{(Eq. 36)}$$

where sgn( ) is the signum function, and t is a predetermined threshold value, set in one version to 0.

Phase locking value (PLV): A statistical descriptor that looks at the instantaneous phase difference between the two halves of the movement signal $c_3$ to indicate how much the two halves resemble each other. A typical CSR event exhibits high phase similarity between the two halves due to the waxing and waning effect, and therefore a high value of PLV, while one that is corrupted exhibits low similarity. The PLV feature value may be computed as follows:

Take the angle of the Hilbert transform of the absolute value of $c_3$;

Divide the resulting phase waveform into two halves and time-reverse the second half to obtain $\phi_1$ and $\phi_2$;

Apply the following equation:

$$PLV = \frac{1}{N}\left|\sum_{n=0}^{N-1} \exp(j(\phi_1(n)-\phi_2(n)))\right| \quad \text{(Eq. 37)}$$

where N is the number of samples in each half.

Signal Artefactness (SA): A binary indicator of the existence of artefacts in the movement signal $c_3$, such as very sharp sudden peaks that do not resemble the waxing and waning shape of CSR. The SA value is computed from $c_3$ as follows:

$$w(k)=\Theta(z(k)-5\sigma_z) \quad \text{(Eq. 38)}$$

where $z(k)$ is the k-th sample of absolute value of $c_3$ and $\sigma_z$ is the standard deviation of $z(k)$. SA is assigned the value of 1 if $w(k)$ is non-zero for any value of k; and 0 otherwise.

Modulation depth (MD): This feature may be computed as the ratio of two quantities. The first quantity (cycle percentage CP) is the duty ratio of the SDB event, i.e. the ratio of the duration of the ventilatory period of the SDB event to the duration of the apnea/hypopnea period. The second quantity (the amplitude variation AV) is the percentage change in amplitude in the ventilatory period to the amplitude in the apnea/hypopnea period, computed as $$AV = \frac{\sum_{n=1}^{t} |c_3(n)|}{\sum_{n=t}^{N} |c_3(n)|} \quad \text{(Eq. 39)}$$

where t is the location of transition between the ventilatory period and the apnea/hypopnea period. If the duration of the ventilatory period is greater (or less) than the apnea/hypopnea duration then CP will be greater (or less) than 1. The same behaviour will be observed in AV, i.e. greater than 1 if the integral of the ventilation amplitude is greater than the corresponding apnea/hypopnea amplitude, and less than 1 otherwise. MD is then greater than 1 if the SDB event has large amplitude variation and small cycle percentage indicating a large modulation, and less than 1 when the SDB event has a low amplitude variation and a large cycle percentage. A higher value of MD indicates a greater likelihood that an SDB event is a CSR event.

Rise Time (RT): Rise time may be computed as the time required for the movement signal amplitude envelope to rise from x % to y % of its final value, expressed as a percentage of the hyperpnea duration, where x and y are set in one version to 0 and 95. A sudden jump to the maximum amplitude indicates that the SDB event lacks the waxing and waxing effect of a CSR event, so smaller values of rise time indicate the SDB event is less likely to be a CSR event.

Standard Deviation of Power Spectrum AutoCorrelation (STDPSD): Each candidate SDB event is analysed with the fast Fourier transform (FFT) to obtain its corresponding power spectrum. The standard deviation of the autocorrelation of the power spectrum is then computed as another feature to distinguish CSR events from other SDB events.

Maximum Power Frequency (Fmax): The frequency with the maximum power value in the power spectrum of each candidate SDB event is also computed, as a CSR event tends to have Fmax values bigger than 0.15.

The rule-based inference engine applies a set of rules to the computed feature values to mark each candidate SDB event as CSR event, or not a CSR event. In one version of the alternative implementation, the inference engine applies the rules set out in Appendix C.

The alternative implementation of the SDB event confirmation module then partitions the (pre-processed) movement signal into consecutive non-overlapping segments, set in one version of the alternative implementation to 10 minutes in length. The alternative implementation of the event confirmation module then calculates how many CSR events occur in each of the segments. Each segment is marked as a CSR segment if it contains at least 3 consecutive CSR events.

Finally, the alternative implementation of the SDB event confirmation module calculates the ratio of the total duration of CSR segments to the total sleep time (TST), and the ratio of the total duration of CSR segments to the length of the monitoring session (total recording time or TRT).

All implementations of the SDB event confirmation module conclude by storing the event duration and minimum (residual) respiratory effort for each confirmed SDB event.

Feature Calculation 7480

Under the parallel or the hybrid approach, the feature calculation module first combines the confirmed SDB events in each channel by a logical OR operation. Under the combined or single-channel approach, no combination is needed.

In one implementation, the feature calculation module calculates the apnea/hypopnea index (AHI) as the total number of confirmed SDB events divided by the total analysis time (TAT), in hours, computed by the signal selection module.

From the set of confirmed SDB events, the feature calculation module also computes and stores the mean and standard deviation values for duration and residual effort of the confirmed SDB events, both for the overall monitoring session and for the first and second halves of the main sleep period.

A basic calculated feature set may include some or all of the features summarised in Table 1.

TABLE 1

Basic calculated feature set

| Feature group | Description | Number of features |
|---|---|---|
| Breathing Rate | Mean, Std, $5^{th}$, $25^{th}$, $50^{th}$, $75^{th}$, $95^{th}$ percentiles of breathing rate estimates over all epochs | 7 |
| Sleep/Wake | Total Sleep Time, Total Time in Bed, Sleep Efficiency, un-labelled section duration | 4 |
| Activity | Total Movement Time and percentage of intervals with non-zero activity counts | 2 |
| | Mean, Std, skewness, kurtosis, and $5^{th}$, $25^{th}$, $50^{th}$, $75^{th}$, $95^{th}$ percentile of activity count over all intervalswith non-zero activity counts | 9 |
| Signal quality | Total sleep-and-breathing time with good quality and poor quality | 2 |
| ConfirmedSDB events | AHI | 1 |
| | For full monitoring session: | |
| | number of SDB events | 1 |
| | mean, std, skewness, and kurtosis of SDB event duration | 4 |
| | mean, std, skewness, and kurtosis of residual respiratory effort | 4 |
| | For $1^{st}$ and $2^{nd}$ halves of main sleep period: | |
| | number of SDB events | 2 |
| | meanand std of SDB event duration | 4 |
| | mean and std of residual respiratory effort | 4 |
| Modulated breathing cycle length | For full night, $1^{st}$ and $2^{nd}$ halves of main sleep period: | |
| | Number of modulated breathing cycles | 3 |
| | Mean and std of modulation cycle length | 6 |
| | For full monitoring session: | |
| | $5^{th}$, $25^{th}$, $50^{th}$, $75^{th}$, $95^{th}$ percentile of modulation cycle length | 5 |
| Modulated breathing cycleOBW | Mean, std, $5^{th}$, $25^{th}$, $50^{th}$, $75^{th}$, $95^{th}$ percentile of all modulated breathing cycle OBW values | 7 |

The feature calculation module optionally extends the basic feature set by combining the basic features in certain ways and deriving new features from the basic features over a single monitoring session. Table 2 summarises the single-session combined and derived features in one implementation of the feature calculation module:

TABLE 2

Single-session combined and derived features

| Feature group | Description | Number of features |
|---|---|---|
| Combination of Previous features | Total time with SDB | 5 |
| | Ratio of total time with SDB to TST (mins per hour) | |
| | Average SDB per minute of sleep | |
| | Modulation cycle length/SDB event duration | |
| | AHI * Modulation cycle length | |
| Combined breathing rate | Difference between the $95^{th}$ percentile and the $5^{th}$, $25^{th}$, $50^{th}$, $75^{th}$ percentile of all valid breathing rate estimates | 4 |
| Combined Modulation Cycle Length | Difference between the $95^{th}$ percentile and the $5^{th}$, $25^{th}$, $50^{th}$, $75^{th}$ percentile of all valid modulation cycle length estimates | 4 |
| Difference $2^{nd}$ to $1^{st}$ half | Difference between mean modulation cycle length, SDB event duration and residual effort values between the first and the second halves of the main sleep period | 3 |
| Mean over std | Ratio between mean and std values for modulation cycle length, SDB event duration, and residual effort for the monitoring session | 3 |

The feature calculation module optionally further derives features from the basic feature set over multiple monitoring sessions. Table 3 summarises the multi-session derived features in one implementation of the feature calculation module. (The current monitoring session is numbered i.)

TABLE 3

Multi-session derived features

| Feature group | Description | Number of features |
|---|---|---|
| AHI slope 5 sessions | Slope of linear interpolation of AHI over last 5 monitoring sessions i-4 to i | 1 |
| Breathing rate vs. baseline | Difference between the $5^{th}$, $25^{th}$, $50^{th}$, $75^{th}$ and $95^{th}$ percentiles of all valid breathing rate estimates and. a baseline for each statistic defined as the mean of each statistic over monitoring sessionsi-7 and i-2. | 5 |
| Range features | Range of AHI, mean breathing rate, modulation cycle length, SDB event duration, and residual effort between monitoring sessions i-4 and i (more than two valid values are required). Modulation cycle length is normalized over mean. | 5 |

In an alternative implementation of feature derivation over multiple sessions, differential filtering is applied to the basic feature set. In one implementation, differential filtering comprises subtraction of each basic feature value at monitoring session i-N from its value at the current monitoring session i.

The calculated features may be normalised before passing to the prediction step 7330. Normalisation prevents a feature from dominating the prediction merely by virtue of having large absolute values. Conventional normalisation involves dividing the difference between each feature value and its mean value by the standard deviation of that feature value, resulting in a normalised feature with zero mean and unity standard deviation.

However, the calculation of mean and standard deviation of a feature value requires the whole data set to be available beforehand, which is unrealistic for real-time applications such as that of the present technology, where the sensor data is recorded and processed after each session.

In one form of the present technology, normalisation calculates the mean and standard deviation of each feature over a sliding window comprising the n most recent feature values. When the available data comprises fewer than n monitoring sessions, the mean and standard deviation are calculated over all the available data. For each feature value x, normalisation calculates:

$$\bar{x} = \begin{cases} \dfrac{x - \text{mean}(x(1):x(i))}{std(x(1):x(i))}, & i < n \\ \dfrac{x - \text{mean}(x(i-n):x(i))}{std(x(i-n):x(i))}, & i \geq n \end{cases} \quad \text{(Eq. 40)}$$

In one implementation, n is set to 35.

In one implementation, the complete set of basic, combined, single-session-derived, and multi-session-derived features calculated by the feature calculation module are passed to the prediction step 7330.

In alternative implementations, only a subset of the complete set is passed to the prediction step 7330. Such implementations reduce the amount of computation required by the prediction step 7330, at the possible cost of reduced accuracy of event prediction.

In one implementation, the list of some or all of the features passed to the prediction step 7330 is given in Table 4, which also indicates whether each feature is normalised or un-normalised:

TABLE 4

List of features passed to the predictionstep 7330 in one implementation.

| Feature name | Feature type | Normalised |
|---|---|---|
| Total sleep time | Basic | No |
| Activity 75$^{th}$ percentile | Basic | |
| Modulation cycle length 50$^{th}$ percentile | Basic | |
| Residual effort (2$^{nd}$ half − 1$^{st}$ half) | Combined | |
| Apnea duration (mean/std) | Single-session derived | |
| Modulation Cycle Length Range | Multi-session derived | |
| Activity 5$^{th}$ percentile | Basic | Yes |
| Number of SDB events | Basic | |
| Breathing rate95$^{th}$ − 50$^{th}$ | Combined | |
| Residual effort range | Multi-session derived | |

In another implementation, the feature calculation module derives eight statistics from the four truth variables $CS_T$, $M_T$, $NM_T$, and $AH_T$ computed by the alternative implementation of the SDB event detection module:

$CS_{Cum}$ and $CS_{Tot}$ % are the total time and percentage of time the signal belonged to the Cheyne-Stokes class during the monitoring session.

$M_{Cum}$ and $M_{Tot}$ % are the total time and percentage of time the signal belonged to the movement class during the monitoring session.

$NM_{Cum}$ and $NM_{Tot}$ % are the total time and percentage of time the signal belonged to the no-movement class during the monitoring session.

$AH_{Cum}$ and $AH_{Tot}$ % are the total time and percentage of time the signal belonged to the apnea/hypopnea class during the monitoring session.

The percentage values are the total time values normalised by the duration D of the monitoring session.

The feature calculation module partitions the monitoring session into N sub-sessions Q(n) of equal length. The bandwidth, modulation depth and Cheyne-Stokes index values BW, MD and CS computed by the alternative implementation of the SDB event detection module are summed over the CS-class periods within each sub-session, and normalised by D:

$$BW_{CS}Q(n) = \frac{1}{D} \sum_{j \in Q(n), CS_T(j)=true} BW(j) \quad \text{(Eq. 41)}$$

$$MD_{CS}Q(n) = \frac{1}{D} \sum_{j \in Q(n), CS_T(j)=true} MD(j) \quad \text{(Eq. 42)}$$

$$CS_{CS}Q(n) = \frac{1}{D} \sum_{j \in Q(n), CS_T(j)=true} CS(j) \quad \text{(Eq. 43)}$$

The inverted entropy values $H^i$ computed by the alternative implementation of the SDB event detection module are summed over each sub-session, and normalised by D:

$$H^i Q(n) = \frac{1}{D} \sum_{j \in Q(n)} H^i(j) \quad \text{(Eq. 44)}$$

In one implementation, N=4, so the sub-sessions are quartiles.

In one implementation, a subset of the features calculated by the alternative implementation of the feature calculation module are passed to the prediction step 7330. One such subset comprises some or all of the six features listed in Table 5.

TABLE 5

List of features passed to predictionstep 7330 in one implementation of the alternative implementation of the feature calculation module

| Feature name | Feature type |
|---|---|
| $CS_{Cum}$ | Whole-session |
| $AH_{Cum}$ | Whole-session |
| $MD_{CS}Q(3)$ | Sub-session |
| $MD_{CS}Q(4)$ | Sub-session |
| $CS_{CS}Q(3)$ | Sub-session |
| $CS_{CS}Q(4)$ | Sub-session |

In yet another implementation, a subset of the features calculated by both implementations of the feature calculation module with N=4 sub-sessions are normalised and passed to the prediction step 7330. One such subset is may include some or all features listed in Table 6:

TABLE 6

List of features passed to the prediction step 7330 using both implementations of the feature calculation module

| Feature Name | Feature Type |
|---|---|
| $CS_{Tot}$ % | Whole session |
| $CS_{CS}Q(2)$ | Sub-session |
| $BW_{CS}Q(1)$ | Sub-session |
| $MD_{CS}Q(3)$ | Sub-session |
| $H^1Q(3)$ | Sub-session |
| Breathing Rate25$^{th}$ percentile | Basic |
| Number of SDB events | Basic |

TABLE 6-continued

List of features passed to the prediction step 7330 using both implementations of the feature calculation module

| Feature Name | Feature Type |
|---|---|
| SDB Event Duration Mean | Basic |
| SDB Event DurationStd | Basic |
| Residual Effort Std | Basic |
| Residual Effort Std$2^{nd}$ Half | Basic |
| SDB Event Duration Mean $1^{st}$ half | Basic |
| Modulation cyclelength $25^{th}$ percentile | Basic |
| Modulation cycle length $50^{th}$ percentile | Basic |
| Modulation cycle length $75^{th}$ percentile | Basic |
| Modulation cycle length Mean $2^{nd}$ half | Basic |
| Modulation cycle length Std $2^{nd}$ half | Basic |
| AHI * Modulation cycle length | Combined |
| Breathing rate $95^{th}$ – $50^{th}$ percentile | Combined |
| Modulation Cycle Length $95^{th}$ – $75^{th}$ percentile | Combined |
| Residual effort $2^{nd}$ half – $1^{st}$ half | Combined |
| SDB event duration $2^{nd}$ half – $1^{st}$ half | Combined |
| Modulation Cycle Length$2^{nd}$ half – $1^{st}$ half | Combined |
| Breathing Rate$50^{th}$ percentile vsbaseline | Multi-session derived |
| Breathing Rate$75^{th}$ percentile vsbaseline | Multi-session derived |

In one implementation of a form of the present technology in which the prediction step 7330 is omitted, the SDB features returned by the feature extraction step 7320 are the AHI, the total sleep time (TST), the ratio of the total duration of CSR events to the total sleep time (TST), and the ratio of the total duration of CSR events to the length of the monitoring session (total recording time or TRT).

Feature Selection

Subsets of features such as those listed above in Table 4, Table 5, and Table 6 may be obtained by feature selection. Feature selection aims to identify a subset of the complete feature set that allows the prediction step 7330 to efficiently predict clinical events from unseen data with reasonable accuracy.

One scheme for feature selection is termed differential evaluation feature selection (DEFS). DEFS uses a pre-specified number of features to be selected, population size, and number of iterations. DEFS first generates from the complete feature set a population of subsets equal to the pre-specified population size. Each subset comprises a number of randomly selected features equal to the pre-specified number of features. DEFS then applies a perturbation to each of the generated subsets and determines whether each perturbed subset should replace the corresponding generated subset in the population. The perturbation and replacement steps are repeated for the pre-specified number of iterations. For all iterations, the determination of replacement is made using a predetermined figure of merit, by determining whether the perturbed subset yields a better figure of merit than its counterpart. After all iterations are complete, the subset in the population with the best figure of merit is returned as the selected subset.

The predetermined figure of merit is based on the performance of the prediction step 7330 on training data. The training data set comprises multiple monitoring sessions of data obtained from multiple patients. At least some of the sessions in the training data set are associated with a clinical event that has been identified by a clinical expert in the corresponding patient in the period immediately following the associated session. Features are shifted by one monitoring session to ensure the monitoring apparatus 7000 is genuinely predictive (i.e. features at session n cannot be used to predict a clinical event at session n).

To compute the figure of merit for a given subset, for each patient in the training set, the prediction step 7330 (if training is needed) is trained using the sessions from all but that patient, and the trained prediction is carried out on the sessions from that patient to obtain the true positive (TP), false positive (FP), false negative (FN) and true negative (TN) performance ratios for the subset.

In one implementation of DEFS, the figure of merit is the maximum specificity allowing at least 75% of sensitivity, to ensure a steep rise in the receiver operating curve (ROC). A higher figure of merit indicates better performance In an alternative implementation of DEFS, the figure of merit is the ratio of the false positive coverage (FPCoverage), which is the area covered by false positives and is inversely related to specificity, to the sensitivity (TP/(TP+FN)). The FPCoverage and sensitivity are set to have upper and lower bounds of 40% and 75% respectively. A lower figure of merit indicates better performance.

In an optional extension of the above DEFS implementation, the number of features selected is reduced from the pre-specified number by identifying all sub-subsets of the subset selected by DEFS, evaluating the performance of each sub-subset against that of the full subset, and choosing a sub-subset whose performance does not decrease significantly against that of the full subset, as judged by the figure of merit. This extension typically reduces the number of selected features by two.

Another optional extension is a voting system, in which multiple rounds of DEFS are performed, each one specifying a larger number of features than the originally pre-specified number. The number of features is then reduced using a voting scheme on all the selected subsets, whereby a feature is discarded unless least a certain percentage (e.g. 80%) of the selected subsets included the feature.

Prediction 7330

The prediction step 7330 generates a Boolean indication of whether a clinical event is likely to occur within the predetermined prediction horizon, from the vector x of SDB features passed by the feature extraction step 7320.

FIG. 7j is a flow chart illustrating a method 7900 that may be used to implement the prediction step 7330 in one form of the present technology. The method 7900 starts at step 7910, which applies State-Space Principal Component Analysis (SSPCA) to generate the principal components $S_1$, $S_2$, . . . of the feature vector x. SSPCA is equivalent to a self-tuning linear filter bank with orthogonalising properties that is applied to reduce the dimensionality of the feature space.

In one implementation of step 7910, SSPCA starts by embedding the SDB feature vector x, and its predecessors from the preceding monitoring sessions, in a higher-dimensional space to generate a trajectory matrix Z. The embedding requires two parameters: the embedding lag L, and the embedding dimension N:

$$Z = \begin{bmatrix} x_1(0) & L & x_1(L-1) \\ M & O & M \\ x_1(NL) & L & x_1((N+1)L-1) \\ x_2(0) & L & x_2(L-1) \\ M & O & M \\ x_2(NL) & L & x_2((N+1)L-1) \\ & M & \end{bmatrix} \quad \text{(Eq. 45)}$$

where $x_i(j)$ is the value of the i-th component of the feature vector x at the monitoring session indexed by j. The dimensions of Z are M(N+1) rows by L columns, where M is the number of selected features. In one implementation, L=1 and N=30.

SSPCA then performs a singular value decomposition of the trajectory matrix Z:

$$Z = P_S D P_E^T \quad (Eq. 46)$$

where D has the L singular values $d_i$ of Z in descending order on its diagonal with zeros elsewhere, and $P_S$ and $P_E$ are square unitary matrices whose columns are the left and right singular vectors $s_i$ and $e_i$ respectively of Z, satisfying $$Z e_i = d_i s_i \quad (Eq. 47)$$

The state space principal component matrix SSPC is then computed from the largest $n_0$ singular values $d_i$ by projecting the trajectory matrix Z onto the corresponding $n_0$ left singular vectors $s_i$:

$$SSPC = P_{S_{n0}}^T Z \quad (Eq. 48)$$

The matrix SSPC has $n_0$ rows and L columns. The rows of the matrix SSPC are the $n_0$ principal components $S_1$, $S_2$, ..., $S_{n0}$ of the feature vector x. In one implementation, $n_o$ is set to 4.

In an optional final step of SSPCA, the $n_0$ principal components $S_1, S_2, \ldots, S_{n0}$ (the rows of the matrix SSPC) are each bandpass filtered to the frequency band [0.001 Hz, 0.05 Hz] using a second order Butterworth filter.

Returning to the method 7900, an optional step 7920 (shown dashed in FIG. 7j) estimates the coefficients H of an adaptive predictive linear (APL) model for the principal component $S_1$ over the predetermined prediction horizon. In one implementation, the APL model is an Auto-Regressive Moving-Average model with exogenous input (ARMAX) model of order 12, and the prediction horizon is seven sessions. A least mean square (LMS) algorithm may be used to estimate the coefficients H of the APL model for the principal component $S_1$.

A further optional step 7930 (also shown dashed in FIG. 7j) then computes a differential measure W of the APL model coefficients H computed by the step 7920. The reason for using the differential operator to obtain the differential measure W is that the rate of change of the APL model coefficients H, rather than their absolute value, is of interest for prediction purposes. In one implementation, the differential measure W is computed as follows:

$$W(n) = \left| \nabla_n \sum_i H_i^2(n) \right| \quad (Eq. 49)$$

Finally, step 7940 takes one or more of the principal components $S_1, S_2, \ldots$, and the differential measure W if the optional steps 7920 and 7930 if were performed, and generates a Boolean indication of whether a clinical event is likely to occur within the prediction horizon, as described in more detail below. The method 7900 then concludes.

In one implementation of the prediction step 7940, suitable for the case where steps 7920 and 7930 were used to compute the differential measure W, a heuristic rule is used to generate the Boolean indication. In this implementation, the Boolean indication P is a binary-valued (1==True, 0==False) function of the principal component $S_1$, the differential measure W, and three thresholds $T_a$, $T_w$, and $T_n$:

$$P = \Theta(|S_1| - T_a)(1 - \Theta(W - T_w)) + (1 - \Theta(S_0 - T_n)) \quad (Eq. 50)$$

where $\Theta$ is the Heaviside step function. The thresholds $T_a$, $T_w$, and $T_n$ are chosen in the following ranges dependent on the extreme values of $S_1$ and W:

$$T_a \in [0, 0.1] \max(S_1)$$

$$T_w \in [0, 0.1] \max(W)$$

$$T_n \in [0, 0.3] \min(S_1) \quad (Eq. 51)$$

In another implementation of the prediction step 7940, suitable for the case where steps 7920 and 7930 have been omitted, a different heuristic rule is applied to generate the Boolean indication P from the first two principal components $S_1$ and $S_2$. Under this heuristic rule, P is true if both $S_1$ and $S_2$ lie within predetermined ranges $(T_{1I}, T_{1S})$ and $(T_{2I}, T_{2S})$ respectively:

$$P = (S_1 > T_{1I}) \& (S_1 < T_{1S}) \& (S_2 > T_{2I}) \& (S_2 < T_{2S}) \quad (Eq. 52)$$

where $T_{1I}$, $T_{1S}$, $T_{2I}$ and $T_{2S}$ are predetermined endpoints. In one implementation, the following endpoints are used: $T_{1I} = T_{2I} = 0.35$; $T_{1S} = T_{2S} = 20$.

In other implementations of the prediction step 7940, a classifier is applied to estimate the posterior probability of its input vector y belonging to each of c output classes, one of which is a "no-event-occurring" class and the remainder being associated with various types of clinical event occurring during the predetermined prediction horizon. Each estimated posterior probability is compared with a posterior probability threshold. If the posterior probability of any class associated with a clinical event occurring is greater than the posterior probability threshold, the Boolean indication is set to True; otherwise, the Boolean indication is set to False.

In some classifier-based implementations of the prediction step 7940, the input vector y to the classifier is one or more of the principal components $S_1, S_2, \ldots, S_{n0}$ and the differential measure W (if computed).

In one such implementation of the prediction step 7940, the classifier is a Quantum Neural Network (QNN) applied to the principal component $S_i$ and the differential measure W. The QNN is first trained on training data comprising multiple input vectors with respective associated class labels. A QNN works as a fuzzy nonlinear inference system and can approximate complex functions with very few hidden neurons.

In further such implementation of the prediction step 7940, the classifier is a naive Bayesian classifier applied to the principal component $S_1$ and the differential measure W. The Bayesian classifier is naive in that it assumes the independence of the classes.

In other such implementations of the prediction step 7940, a QNN or a Bayesian classifier as described above is applied to the first k principal components $S_1, \ldots, S_k$, omitting the differential measure W.

In an alternative implementation of the prediction step 7330, the steps 7910, 7920, and 7930 are omitted, and the input vector y to the classifier used at step 7940 is simply the SDB feature vector x. Such "direct" implementations of step 7330 are less computationally intensive than those using the complete method 7900, provided the feature vector x is not too long.

In one such implementation, the classifier used at step 7940 is a linear discriminant analysis (LDA) classifier. The basic idea of LDA classification is to find a linear combination of features which characterize or separate different classes. LDA does not require multiple passes over the data for parameter optimization and naturally handles problems with more than two classes.

An LDA classifier estimates the posterior probability $P_k$ of a given input vector y belonging to each of c classes indexed by k=1, ..., c as $$P_k = \frac{\exp(z_k)}{\sum_{i=1}^{c} \exp(z_i)} \quad \text{(Eq. 53)}$$

where $$z = W_0 + W_1 y \quad \text{(Eq. 54)}$$

is a linear transformation of the vector y to a c-vector z.

The parameters $W_0$ (a c-vector) and $W_1$ (a c-by $N_f$ matrix, where $N_f$ is the length of the input vector y) of the linear transformation are obtained by training the LDA classifier on training data comprising multiple vectors with respective associated class labels. The class means $\Sigma_k$ and covariances $\Sigma_k$ of the training vectors in each class k are first obtained. The common covariance $\Sigma$ is then computed as the weighted sum of the class covariances $\Sigma_k$. The weights of all classes are set to 1/c in one implementation. In an alternative implementation, the weight of each class is the fraction of training vectors labelled with that class.

The k-th row of the linear transformation parameters $W_0$ and $W_1$ are then computed for each class k as $$W_{0,k} = -\left(\frac{1}{2}\right) \mu_k^T \Sigma^{-1} \mu_k \log(\pi_k) \quad \text{(Eq. 55)}$$

$$W_{1,k} = \mu_k^T \Sigma^{-1} \quad \text{(Eq. 56)}$$

where the $\pi_k$ are the prior class probabilities, set to 1/k in one implementation.

If the input vector y contains one or more missing features (i.e. components set to NaN), as is not uncommon for movement data obtained from contactless motion sensors, the linear transformation parameters defined by (Eq. 55) and (Eq. 56) cannot be applied to the incomplete feature vector y as in (Eq. 54). For such incomplete feature vectors y, "reduced" class means $\mu_k'$ and covariances $\Sigma_k'$ are computed for each class k based only on the available features in the incomplete input feature vector y. A reduced common covariance matrix $\Sigma'$ is then computed as the weighted sum of the reduced class covariances $\Sigma_k'$ as above. "Reduced" linear transformation parameters $W_0'$ and $W_1'$ are then computed from the reduced class means and the reduced common covariance matrix $\Sigma'$ using (Eq. 55) and (Eq. 56). Finally, the linear transformation (Eq. 54) using the "Reduced" linear transformation parameters $W_0'$ and $W_1'$ is applied to the incomplete feature vector y to obtain the posterior probabilities $P_k$.

In classifier-based implementations of the prediction step 7940, the number c of classes is usually two, since the training data vectors have only two labels: event predicted, or event not predicted. However, in some implementations, the event-predicted class may be subdivided into sub-classes associated with different predicted events by first clustering the associated vectors into sub-classes, e.g. by k-means clustering.

In classifier-based implementations of the prediction step 7940, the value of the posterior probability threshold needs to be set. In some versions of these implementations, the training data set is used to set the posterior probability threshold to the value that minimises the false positive coverage in the ROC for a sensitivity value greater or equal than a threshold, set in one implementation to 75%.

In other versions of these implementations, the setting of the posterior probability threshold is combined with feature selection, by making the posterior probability threshold an extra parameter to be optimised by the DEFS method described above, constrained to lie within the range [0, 1].

In accordance with one application of the monitoring apparatus 7000, where an alert is to be provided between session n-7 and session n-1 for a clinical event predicted at session n, i.e. a seven-session prediction horizon, each positive prediction is expanded by seven sessions into the future. This modification was included in the calculation of sensitivity and false positive coverage used in classifier training and feature selection.

Also, for training purposes, the reverse of this operation was performed on the clinical expert evaluations, with smearing between session n-7 and session n-1 for a clinical event deemed to occur at session n. This was only applied on training data as it was found to be the most effective range for enhancing classifier performance.

Glossary

For the purposes of the present technology disclosure, in certain forms of the present technology, one or more of the following definitions may apply. In other forms of the present technology, alternative definitions may apply.

General

Air: In certain forms of the present technology, air supplied to a patient may be atmospheric air, and in other forms of the present technology atmospheric air may be supplemented with oxygen.

Continuous Positive Airway Pressure (CPAP): The application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation (SaO2), partial pressure of carbon dioxide (PCO2), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

Aspects of the Respiratory Cycle

Apnea: Apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in respiratory effort, or the absence of respiratory effort.

Breathing rate: The rate of spontaneous respiration of a patient, usually measured in breaths per minute.

Duty cycle: The ratio of inhalation time, Ti to total breath time, Ttot.

Effort (respiratory): The work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal flow.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in liters per minute.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$. For nasal CPAP treatment of OSA, a reference to treatment pressure is a reference to a pressure in the range of about 4-20 $cmH_2O$, or about 4-30 $cmH_2O$. The pressure in the patient interface is given the symbol Pm.

Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

REFERENCE LABELS LIST

| | |
|---|---|
| patient | 1000 |
| sensor unit | 1200 |
| patient interface | 3000 |
| pap device | 4000 |
| external housing | 4010 |
| upper portion | 4012 |
| portion | 4014 |
| panel | 4015 |
| chassis | 4016 |
| handle | 4018 |
| pneumatic block | 4020 |
| pneumatic component | 4100 |
| air circuit | 4170 |
| electrical component | 4200 |
| processes | 4300 |
| humidifier | 5000 |
| water reservoir | 5110 |
| heating plate | 5120 |
| apparatus | 7000 |
| microcontroller unit MCU | 7001 |
| memory | 7002 |
| movement signal | 7003 |
| I signal | 7003a |
| Q signal | 7003b |
| communications circuitry | 7004 |
| external computing device | 7005 |
| processor | 7006 |
| connection | 7008 |
| contactless motion sensor | 7010 |
| display device | 7015 |
| audio output | 7017 |
| transmitter | 7020 |
| receiver | 7030 |
| local oscillator | 7040 |
| antenna | 7050 |

-continued

| | |
|---|---|
| signal | 7060 |
| signal | 7070 |
| mixer | 7080 |
| method | 7100 |
| first step | 7110 |
| step | 7120 |
| step | 7130 |
| step | 7140 |
| arrow | 7145 |
| step | 7150 |
| step | 7160 |
| step | 7170 |
| arrow | 7175 |
| arrow | 7178 |
| step | 7180 |
| method | 7200 |
| step | 7210 |
| step | 7220 |
| step | 7230 |
| prediction method | 7300 |
| step | 7310 |
| step | 7320 |
| step | 7330 |
| block diagram | 7400 |
| module | 7410 |
| presence/Absence detection module | 7420 |
| sleep/wake analysis module | 7430 |
| breathing rate estimation module | 7440 |
| signal selection module | 7450 |
| modulation cycle metrics calculation module | 7455 |
| envelope generation module | 7460 |
| sdb event detection module | 7465 |
| sdb event confirmation module | 7470 |
| feature calculation module | 7480 |
| block diagram | 7500 |
| movement detection module | 7510 |
| presence/absence detection module | 7520 |
| sleep/wake analysis module | 7530 |
| breathing rate estimation module | 7540 |
| signal selection module | 7550a |
| signal selection module | 7550b |
| modulation cycle metrics calculation module | 7555 |
| envelope generation module | 7560a |

-continued

| | |
|---|---|
| envelope generation module | 7560b |
| sdb event detection module | 7565a |
| sdb event detection module | 7565b |
| sdb event confirmation module | 7570a |
| sdb event confirmation module | 7570b |
| feature calculation module | 7580 |
| method | 7900 |
| step | 7910 |
| step | 7920 |
| step | 7930 |
| step | 7940 |

APPENDIX A $k$ ranges from $-CL/2$ to $CL/2$.
Template 1:

$$t1[k] = -\left(\frac{1}{2\pi\sqrt{\beta}} \exp\left(-\frac{k^2}{2\beta}\right)\right)$$

where $\beta = 6000$.
Template 2:

$$t2[k] = \begin{cases} \cos\left(\frac{k\pi}{CL/4}\right) + 1, & -\frac{CL}{2} \leq k < -\frac{CL}{4} \\ 0, & -\frac{CL}{4} \leq k < 0 \\ -\sin\left(\frac{(k - CL/4)\pi}{CL/4}\right) + 1, & 0 \leq k < \frac{CL}{2} \end{cases}$$

Template 3:

$$t3[k] = t2[-k]$$

APPENDIX B

```
// Extract the inter-quartile range statistics for each feature over the session
[y05K y25K y50K y75K y95K] = IqRange(K)
[y50HWL y25HWL y50HWL y75HWL y95HWL] = IqRange(H_w1)
[y50ME y25ME y50ME y75ME y95ME] = IqRange(ME)
[IR05 IR25 IR50 IR75 IR95] = IqRange(IR)
// Batch process the statistics for each feature for each candidate SDB event
// Create a logical index vector for the detected events (1 means that this SDB event is
confirmed, 0 otherwise)
Index = ones(NumberCandidateEvents ,1);
// keep events whose DOF value is less than 0.9, i.e., non-noise or non-spike like
events
Index = Index .* (DOF<.9);
// Rule 1: Patients with very high AHI values tend to have y05K of non-zero value,
for others it is always zero
if y05K ~= 0
   if y95HWL>8.5 OR y95HWL<4.5
      Index = Index .* (K<23 .* K >5);
   else
      //keep most of the events
      Index = Index .* (K<33 .* K>3.5);
   end
end
// Rule-2: Patients with very low AHI values tend to have y05K y25K and y50K all of
zero values, for others these values are not all-zeros
If sum([y05K y25K y50K])==0
   // Attempt to confirm the SDB events with K<24 but non-zero
   Index = (Index .* (K <24)) .* K >0;
end
// The rest of the rules focus on patients with intermediate AHI values
// Rule-3: mainly focusing on those with AHI <10: Remove events with K>=12 as the
range should be small here
```

APPENDIX B-continued

```
If sum([y05K y25K])==0 AND y75K*3>50
    Index = (Index .* (K <12)) .* K >0;
end
// Rule-4: mainly focus on those with AHI<20
If sum([y05K y25K])==0 AND y75K*3>30 AND y95K>30
   if y95K>45
      Index = (Index .* (K <12)) .* K >4;
   else
      Index = (Index .* (K <22)) .* K >0;
   end
end
// Rule-5: mainly focus on those with AHI<30
If (y25HWL<.2 AND y25HWL>.075 AND y25K<2)
   Index = (Index .* (K <12)) .* K >3;
end
// Rule-6: mainly focus on those with AHI<50, wide range expected here varying
from AHI>=5 to AHI<=50
If y05K==0 AND y75K*3>30 AND y75K*3<60 AND y95K>30 AND y95HWL>5
AND y25HWL<.646%.45
   if y95K>38.55 AND y95K<44 AND y95ME>0.1 AND y95ME<0.13
      Index = (Index .* (K <12)) .* K >5;
   elseif y95K>38.55 AND y95ME>0.1
      Index = (Index .* (K <40)) .* K >2;
   else
      Index = (Index .* (K <16)) .* K >4;
      Index = (Index .* (ME<0.08));
   end
end
// Rule-7: mainly for those patients with AHI>30 and AHI<60
If y05K==0 AND (y75K*2 > y95K)
   Index = Index .* (K <38-round(y05K));
end
// Rule-8: cover any other situation not covered above
if sum([y05HWL y25HWL])~=0 AND y95ME>=0.11
   Index = (Index .* (K <20)) .* K >4;
end
if sum([y05HWL y25HWL])==0 AND y95ME<0.04
   Index = (Index .* (K <15)) .* K >4;
end
//Rule-9: covers the range of the irregularity factor
Index = Index .* (IR< max(IR95/2,.8));
```

APPENDIX C

```
// Extract the inter-quartile-range descriptors for each feature
[STDP05 STDP25 STDP50 STDP75 STDP95] = IqRangePlus(STDPSD);
[PLV05 PLV25 PLV50 PLV75 PLV95] = IqRangePlus(PLV);
[Fmax05 Fmax25 Fmax50 Fmax75 Fmax95] = IqRangePlus(Fmax);
[CP05 CP25 CP50 CP75 CP95] = IqRangePlus(CP);
[CWL05 CWL25 CWL50 CWL75 CWL95] = IqRangePlus(CWL);
// Create a logical index vector for the confirmed SDB events (1 means
that this event should be marked as a CSR event, 0 otherwise)
IndexCS   = (CL<= 90) & (CL>= 30);
IndexCS   = IndexCS .* (ZC>=6 & ZC<=40);
IndexCS   = IndexCS .* (MD<=1.3 & MD>=.1);
IndexCS   = IndexCS .* (K <=30);
IndexCS   = IndexCS .* (DOF>=0.35 & DOF<.9);
IndexCS   = IndexCS .* (STDPSD<=( min(100, STDP75*(( STDP75-
STDP50)<500))));
IndexCS   = IndexCS .* (Fmax>=max(Fmax50-Fmax25,0.15));
IndexCS   = IndexCS .* (PLV>=PLV50+0.05);
IndexCS   = IndexCS .* (RT>=0.22 &VentlLength>15);
IndexCS   = IndexCS .* (CP<=0.95*mean([CP75 CP95]));
IndexCS   =AND(IndexCS,CWL<10&CWL>(max(1,CWL25/1.2 *
(CWL25>1) + CWL50/2.2*(CWL25<1))));
```

The invention claimed is:

1. A cardio-pulmonary health monitoring apparatus comprising:
   a contactless motion sensor configured to generate one or more movement signals representing bodily movement of a patient during a monitoring session;
   a processor; and
   a memory storing program instructions configured to cause the processor to carry out a method of processing the one or more movement signals, the method comprising:
   selecting one or more sections of the one or more movement signals, being sections during which the patient was asleep and not performing gross bodily movements,
   extracting one or more sleep disordered breathing (SDB) features from said sections of the one or more movement signals, and
   predicting whether a clinical event is likely to occur during a predetermined prediction horizon based on the one or more SDB features,
   wherein the selecting comprises selecting one or more sections of good quality, and
   wherein sections of good quality comprise sections in which a figure of merit for the movement signal over the section exceeds a noise threshold for the section, and
   wherein the noise threshold for the section is the smaller of a maximum noise value for the motion sensor and a percentile of a distribution of root mean square (RMS) values of the movement signal over the section.

2. A cardio-pulmonary health monitoring apparatus according to claim 1, wherein the contactless motion sensor, the processor, and the memory form part of a contactless sensor unit.

3. A cardio-pulmonary health monitoring apparatus according to claim 2, wherein the method further comprises sending an alert message to an external computing device dependent on the prediction.

4. A cardio-pulmonary health monitoring apparatus according to claim 1, wherein the processor and the memory form part of a computing device that is external to the contactless motion sensor.

5. A cardio-pulmonary health monitoring apparatus according to claim 1, further comprising a display, wherein the method further comprises displaying an alert message on the display dependent on the prediction.

6. A cardio-pulmonary health monitoring apparatus according to claim 1, further comprising an audio output, wherein the method further comprises generating an alarm by the audio output dependent on the prediction.

7. A cardio-pulmonary health monitoring apparatus according to claim 1, wherein the contactless motion sensor is a radio-frequency motion sensor.

8. A cardio-pulmonary health monitoring apparatus according to claim 7, wherein the radio-frequency motion sensor is configured to generate two movement signals based on respective transmitted radio-frequency signals that are in quadrature with each other.

9. A cardio-pulmonary health monitoring apparatus according to claim 8, wherein the method comprises combining the two movement signals into a combined movement signal before the extracting.

10. A cardio-pulmonary health monitoring apparatus according to claim 8, wherein the method comprises combining the SDB features extracted from each movement signal before the predicting.

11. A cardio-pulmonary health monitoring apparatus according to claim 1, wherein the processor is further configured to extract the SDB features from one or more movement signals obtained from a contact motion sensor.

12. A cardio-pulmonary health monitoring apparatus according to claim 1, wherein the processor is further configured to extract the SDB features from data relevant to the cardio-pulmonary health of the patient obtained from a non-motion sensor.

13. A cardio-pulmonary health monitoring apparatus comprising:
- a contactless sensor unit comprising a contactless motion sensor configured to generate one or more movement signals representing bodily movement of a patient during a monitoring session,
- a processor, and
- a memory storing program instructions configured to cause the processor to carry out a method of processing the one or more movement signals, the method comprising:
  - selecting one or more sections of the one or more movement signals, being sections during which the patient was asleep and not performing gross bodily movements,
  - computing a correlation feature by correlating a respiratory effort envelope of each selected section of the movement signals with one or more respiratory effort templates,
  - detecting a sleep disordered breathing (SDB) event whenever the correlation feature exceeds a first threshold for a duration that is greater than a second threshold, and
  - calculating one or more SDB features from the detected SDB events, the SDB features being indicative of severity of sleep-disordered breathing by the patient during the monitoring session.

14. A cardio-pulmonary health monitoring apparatus according to claim 13, wherein the method further comprises sending an alert message to an external computing device dependent on the calculated SDB features.

15. A cardio-pulmonary health monitoring apparatus according to claim 13, wherein the method further comprises displaying an alert message on a display dependent on the calculated SDB features.

16. A cardio-pulmonary health monitoring apparatus according to claim 13, further comprising an audio output, wherein the method further comprises generating an alarm by the audio output dependent on the calculated SDB features.

17. A cardio-pulmonary health monitoring apparatus according to claim 13, wherein the one or more calculated SDB features comprises a plurality of features from the group consisting of:
- apnea/hypopnea index;
- total sleep time;
- ratio of the total duration of Cheyne-Stokes respiration events to the total sleep time; and
- ratio of the total duration of Cheyne-Stokes respiration events to the duration of the monitoring session.

18. A cardio-pulmonary health monitoring apparatus according to claim 13, wherein the contactless motion sensor is a radio-frequency motion sensor.

19. A cardio-pulmonary health monitoring apparatus according to claim 18, wherein the radio-frequency motion sensor is configured to generate two movement signals based on respective transmitted radio-frequency signals that are in quadrature with each other.

20. A cardio-pulmonary health monitoring apparatus according to claim 19, wherein the method comprises combining the two movement signals into a combined movement signal before the extracting.

21. A cardio-pulmonary health monitoring apparatus according to claim 19, wherein the method comprises combining the SDB features extracted from each movement signal before the predicting.

22. A cardio-pulmonary health monitoring apparatus according to claim 13, wherein the processor is further configured to extract the SDB features from one or more movement signals obtained from a contact motion sensor.

23. A method of monitoring cardio-pulmonary health of a patient, the method comprising:
- selecting one or more sections of one or more movement signals representing bodily movement of the patient, the movement signals being generated by a contactless motion sensor directed at the patient during a monitoring session, the selected sections being sections during which the patient was asleep and not performing gross bodily movements,
- extracting one or more sleep disordered breathing (SDB) features from said sections of the one or more movement signals, and
- predicting whether a clinical event is likely to occur during a predetermined prediction horizon based on the one or more SDB features,
- wherein the selecting comprises selecting one or more sections of good quality, and
- wherein sections of good quality comprise sections in which a figure of merit for the movement signal over the section exceeds a noise threshold for the section, and
- wherein the noise threshold for the section is the smaller of a maximum noise value for the motion sensor and a percentile of a distribution of root mean square (RMS) values of the movement signal over the section.

24. A method according to claim 23, wherein the extracting comprises:
  detecting SDB events in said sections, and
  calculating SDB features from the detected SDB events.

25. A method according to claim 24, wherein detecting SDB events comprises:
  computing a correlation feature by correlating a respiratory effort envelope of each said section of the movement signal with one or more respiratory effort templates, and
  detecting an SDB event whenever the correlation feature exceeds a first threshold for a duration that is greater than a second threshold.

26. A method according to claim 24, wherein detecting SDB events comprises
  computing a mean value of a respiratory effort envelope of each said section over a main window,
  calculating a baseline as the mean respiratory effort envelope value over two windows surrounding the main window, and
  detecting an SDB event if the mean respiratory effort envelope value over a main window satisfies an apnea criterion or a hypopnea criterion with respect to the calculated baseline.

27. A method according to claim 24, wherein the extracting comprises first pre-processing the movement signals.

28. A method according to claim 27, wherein the pre-processing comprises de-trending each movement signal.

29. A method according to claim 27, wherein the number of movement signals is two, and the pre-processing comprises first combining the two movement signals.

30. A method according to claim 29, wherein the combining comprises:
  removing the mean of each movement signal,
  computing the minimum value of each movement signal,
  computing the length of a sample vector whose components at each sample are the distances of the respective movement signals from their respective minimum values, and
  removing the mean of the length at each sample.

31. A method according to claim 23, wherein the figure of merit is a root mean square (RMS) value of the movement signal over the section.

32. A method according to claim 23, wherein the figure of merit is the $75^{th}$ percentile of the distribution of RMS values of the movement signal over the section.

33. A method according to claim 23, wherein said sections comprise epochs in which the patient is present and a waveform length value of the movement signal in the epoch is less than a threshold.

34. A method according to claim 33, wherein epochs in which the patient is present are epochs in which a root mean square (RMS) value of the movement signal within the epoch exceeds a noise-only threshold.

35. A method according to claim 23, wherein said sections in which the patient was asleep and not performing gross bodily movements comprise epochs in which the patient was asleep and a variance of the movement signal within the epoch exceeds a threshold for the monitoring session.

36. A method according to claim 23, wherein the predicting comprises applying a classifier to classify the SDB features into a "no-event-occurring" class or an "event-occurring" class.

37. A method according to claim 36, wherein the classifier is a linear discriminant analysis classifier.

38. A method according to claim 36, wherein the classifier is applied to one or more principal components of the SDB features.

39. A method according to claim 23, wherein the predicting comprises applying a heuristic rule to one or more principal components of the SDB features.

40. A method according to claim 23, further comprising:
  triggering generation on a display of at least one query based on the prediction, the query being configured to prompt the patient for a response; and
  triggering generation of a clinical alert based on a patient response to the query.

41. A method according to claim 23, further comprising generating a potential relapse alert based on the prediction.

42. A method of monitoring cardio-pulmonary health of a patient, the method comprising:
  selecting one or more sections of one or more movement signals representing bodily movement of the patient, the movement signals being generated by a contactless motion sensor directed at the patient during a monitoring session, the selected sections being sections during which the patient was asleep and not performing gross bodily movements,
  extracting one or more sleep disordered breathing (SDB) features from said sections of the one or more movement signals, and
  predicting whether a clinical event is likely to occur during a predetermined prediction horizon based on the one or more SDB features,
  wherein said sections in which the patient was asleep comprise epochs labelled by a linear discriminant analysis (LDA) classifier as asleep, wherein the LDA classifier is configured to label each epoch based on an activity count series and a movement flag series for the epoch, and
  wherein the movement flag series is obtained by:
    computing a noise feature, a correlation feature, and a power feature for each sample of the movement signal; and
    setting a movement flag for each sample to true if a noise feature for the sample is above a high threshold and the corresponding correlation and power features are below a low threshold, otherwise setting the movement flag to false.

43. A method according to claim 42, wherein the activity count series is obtained by integrating an envelope of the movement signal over one or more intervals within the epoch.

44. A method according to claim 42, wherein said sections in which the patient was asleep and not performing gross bodily movements comprise sections in which the patient was asleep and a movement flag series indicating gross bodily movement is false.

45. A method of monitoring cardio-pulmonary health of a patient, the method comprising:
  selecting one or more sections of one or more movement signals representing bodily movement of the patient, the movement signals being generated by a contactless motion sensor directed at the patient during a monitoring session, the selected sections being sections during which the patient was asleep and not performing gross bodily movements, and
  computing a correlation feature by correlating a respiratory effort envelope of each said selected section of the movement signals with one or more respiratory effort templates, detecting a sleep disordered breathing (SDB) event whenever the correlation feature exceeds a first threshold for a duration that is greater than a second threshold, and calculating one or more SDB features from the detected SDB events, the SDB features being indicative of severity of sleep-disordered breathing by the patient during the monitoring session.

46. A method according to claim 45, wherein the correlation feature is the maximum of the correlation values over the respiratory effort templates.

47. A method according to claim 45, wherein the respiratory effort templates are respective generic templates whose duration has been scaled by a mean breathing modulation cycle length estimated for the patient over the monitoring session.

48. A method according to claim 47, wherein the breathing modulation cycle length is estimated as a weighted average of the reciprocal of the peak frequencies of the power spectral density of the respiratory effort envelope computed over one or more macro-epochs within the section.

49. A method according to claim 48, wherein the weighting is dependent on the heights of the respective peaks.

50. A method according to claim 45, further comprising confirming each detected SDB event as a valid SDB event.

51. A method according to claim 50, wherein the confirming comprises verifying that hyperpnea sections adjacent the minimum of a respiratory effort envelope corresponding to each detected event have a duration greater than a minimum value.

52. A method according to claim 51, wherein the confirming further comprises verifying that the respiratory effort envelope dips below a hypopnea threshold for a time greater than one fifth of a modulation cycle length for the patient.

53. A method according to claim 50, wherein the confirming comprises:
computing one or more features from the movement signal corresponding to each candidate SDB event, and
applying a rule-based inference engine to the one or more computed features to determine whether to confirm each detected SDB event.

54. A method according to claim 45, wherein the respiratory effort envelope is calculated for the section by low-pass filtering the modulus of a complex-valued signal whose real part is the movement signal of the section and whose imaginary part is the Hilbert transform of the movement signal of the section.

55. A method according to claim 45, wherein the respiratory effort envelope is calculated for the section as the empirical mode decomposition of the Hilbert transform of the movement signal of the section.

56. A method according to claim 45, wherein the respiratory effort envelope is calculated for the section by applying a double max and hold filter to the movement signal of the section to compute a positive envelope and a negative envelope, and subtracting the negative envelope from the positive envelope.

57. A method according to claim 45, wherein the calculating comprises computing statistics of the detected SDB events for the monitoring session.

58. A method according to claim 57, wherein the calculating further comprises calculating the statistics of the detected SDB events for each of multiple sub-sessions of the monitoring session.

59. A method according to claim 58, wherein the sub-sessions are halves of a main sleep period of the monitoring session.

60. A method according to claim 58, wherein the sub-sessions are quartiles of the monitoring session.

61. A method according to claim 57, wherein the calculating comprises computing statistics of the detected SDB events for multiple monitoring sessions.

62. A method according to claim 57, wherein the calculating further comprises normalising the calculated SDB features to zero mean and unity standard deviation over a sliding window comprising multiple monitoring sessions preceding and including the monitoring session.

63. A method according to claim 62, wherein the sliding window comprises all monitoring sessions preceding and including the monitoring session.

64. A computer-readable medium storing program instructions configured to cause a processor to carry out a method of monitoring cardio-pulmonary health of a patient, the method comprising:
selecting one or more sections of one or more movement signals representing bodily movement of the patient, the movement signals being generated by a contactless motion sensor directed at the patient during a monitoring session, the selected sections being sections during which the patient was asleep and not performing gross bodily movements, and
computing a correlation feature by correlating a respiratory effort envelope of each said selected section of the movement signals with one or more respiratory effort templates,
detecting a sleep disordered breathing (SDB) event whenever the correlation feature exceeds a first threshold for a duration that is greater than a second threshold, and
calculating one or more sleep disordered breathing features from the detected SDB events, the SDB features being indicative of severity of sleep-disordered breathing by the patient during the monitoring session.

* * * * *